US010814013B2

(12) United States Patent
Yang et al.

(10) Patent No.: US 10,814,013 B2
(45) Date of Patent: Oct. 27, 2020

(54) EFFICIENT SYNTHESIS OF CHELATORS FOR NUCLEAR IMAGING AND RADIOTHERAPY: COMPOSITIONS AND APPLICATIONS

(75) Inventors: David J. Yang, Sugar Land, TX (US); Dongfang Yu, Pearland, TX (US); Andrew S. Thompson, Mountainside, NJ (US); F. David Rollo, Saratoga, CA (US)

(73) Assignees: The Board of Regents of the University of Texas System, Austin, TX (US); Cell>Point, LLC, Spring, TX (US)

( * ) Notice: Subject to any disclaimer, the term of this patent is extended or adjusted under 35 U.S.C. 154(b) by 125 days.

(21) Appl. No.: 13/562,879

(22) Filed: Jul. 31, 2012

(65) Prior Publication Data
US 2013/0039853 A1 Feb. 14, 2013

Related U.S. Application Data

(62) Division of application No. 11/770,395, filed on Jun. 28, 2007.

(60) Provisional application No. 60/828,347, filed on Oct. 5, 2006.

(51) Int. Cl.
*A61K 49/00* (2006.01)
*A61K 51/04* (2006.01)
*A61K 49/06* (2006.01)

(52) U.S. Cl.
CPC .......... *A61K 49/0002* (2013.01); *A61K 49/06* (2013.01); *A61K 51/0491* (2013.01)

(58) Field of Classification Search
CPC .. A61P 29/00; A61P 9/00; A61P 35/02; A61P 35/00; A61P 9/10; A61P 31/00; A61P 9/06; A61K 49/0002; A61K 51/0491; A61K 49/103; A61K 49/06
USPC ...................... 600/436; 424/1.11, 1.65, 1.73
See application file for complete search history.

(56) References Cited

U.S. PATENT DOCUMENTS

| | | | |
|---|---|---|---|
| 4,141,654 A | 2/1979 | Wardlaw et al. | 356/243.1 |
| 4,181,654 A | 1/1980 | Weitl et al. | 260/239 |
| 4,279,992 A | 7/1981 | Boguslaski et al. | 435/7 |
| 4,418,068 A | 11/1983 | Jones | 514/337 |
| 4,507,466 A | 3/1985 | Tomalia et al. | 528/332 |
| 4,558,120 A | 12/1985 | Tomalia et al. | 528/363 |
| 4,568,737 A | 2/1986 | Tomalia et al. | 528/332 |
| 4,587,329 A | 5/1986 | Tomalia et al. | 528/363 |
| 4,631,337 A | 12/1986 | Tomalia et al. | 528/391 |
| 4,694,064 A | 9/1987 | Tomalia et al. | 528/332 |
| 4,713,975 A | 12/1987 | Tomalia et al. | 73/865.8 |
| 4,730,968 A | 3/1988 | Diperstein et al. | 411/178 |
| 4,732,863 A | 3/1988 | Tomasi et al. | 424/1.53 |
| 4,737,550 A | 4/1988 | Tomalia | 525/418 |
| 4,789,542 A | 12/1988 | Goodman et al. | 424/1.73 |
| 4,824,659 A | 4/1989 | Hawthorne | 424/1.53 |
| 4,832,940 A | 5/1989 | Ege | 424/1.41 |
| 4,857,599 A | 8/1989 | Tomalia et al. | 525/259 |
| 4,861,869 A | 8/1989 | Nicolotti et al. | 424/1.53 |
| 4,871,779 A | 10/1989 | Killat et al. | 521/28 |
| 4,925,650 A | 5/1990 | Nosco et al. | 424/1.65 |
| 4,965,392 A | 10/1990 | Fritzberg et al. | 558/254 |
| 4,988,496 A | 1/1991 | Srinivasan et al. | 424/1.53 |
| 5,013,556 A | 5/1991 | Woodle et al. | 424/450 |
| 5,071,965 A | 12/1991 | Dunn et al. | 24/89 |
| 5,087,616 A | 2/1992 | Myers et al. | 514/21 |
| 5,108,921 A | 4/1992 | Low et al. | 435/375 |
| 5,164,294 A | 11/1992 | Skold et al. | 435/7.5 |
| 5,242,679 A | 9/1993 | Fritzberg et al. | 424/1.53 |
| 5,268,163 A | 12/1993 | Verbruggen | 534/14 |
| 5,279,811 A | 1/1994 | Bergstein et al. | 424/1.65 |
| 5,310,536 A | 5/1994 | Srinivasan | 424/1.65 |
| 5,356,793 A | 10/1994 | Koezuka et al. | 435/32 |
| 5,364,613 A | 11/1994 | Sieving et al. | 424/9.3 |
| 5,412,072 A | 5/1995 | Sakurai et al. | 530/322 |
| 5,416,016 A | 5/1995 | Low et al. | 435/375 |
| 5,474,756 A | 12/1995 | Tweedle et al. | 424/9.363 |
| 5,496,533 A | 3/1996 | Jackson et al. | 424/1.65 |
| 5,517,993 A | 5/1996 | Unger et al. | 600/410 |

(Continued)

FOREIGN PATENT DOCUMENTS

| | | |
|---|---|---|
| EP | 1156091 | 11/2001 |
| JP | 05-508162 | 11/1993 |

(Continued)

OTHER PUBLICATIONS

Abrams et al., "Technetium-99m-human polyclonal IgG radiolabeled via the hydrazino nicotinamide derivative for imaging focal sites of infection in rats," *J. Nucl. Med.*, 31:2022-2028, 1990.

Aime et al., "Ternary Gd(III)L-HAS adducts: evidence for the replacement of inner-sphere water molecules by coordinating groups of the protein. implications for the design of contrast agents for MRI," *J. of Biol. Inorg. Chem.*, 5:488-497, 2000.

Alauddin and Conti, "Synthesis and preliminary evaluationo f 9-(4-{18F}-Fluoro-3-Hydroxymethylbutyl)guanine ([18F]FHBG): a new potential imaging agent for viral infection and gene therapy," *Nucl. Med. Biol.*, 25:175-180, 1998.

(Continued)

*Primary Examiner* — Michael G. Hartley
*Assistant Examiner* — Leah H Schlientz
(74) *Attorney, Agent, or Firm* — Parker Highlander PLLC

(57) ABSTRACT

Novel methods of synthesis of chelator-targeting ligand conjugates, compositions comprising such conjugates, and therapeutic and diagnostic applications of such conjugates are disclosed. The compositions include chelator-targeting ligand conjugates optionally chelated to one or more metal ions. Methods of synthesizing these compositions in high purity are also presented. Also disclosed are methods of imaging, treating and diagnosing disease in a subject using these novel compositions, such as methods of imaging a tumor within a subject and methods of diagnosing myocardial ischemia.

12 Claims, 14 Drawing Sheets

(56) References Cited

U.S. PATENT DOCUMENTS

| | | | |
|---|---|---|---|
| 5,534,241 A | 7/1996 | Torchilin et al. | 424/9.321 |
| 5,541,287 A | 7/1996 | Yau et al. | 530/317 |
| 5,569,471 A | 10/1996 | Oguro | 424/649 |
| 5,601,800 A | 2/1997 | Katti et al. | 424/1.77 |
| 5,605,671 A | 2/1997 | Lyle et al. | 424/1.41 |
| 5,605,672 A | 2/1997 | Bogdanov et al. | 424/1.65 |
| 5,608,060 A | 3/1997 | Axworthy et al. | 540/474 |
| 5,609,847 A | 3/1997 | Belinka et al. | 424/1.69 |
| 5,620,675 A | 4/1997 | McBride et al. | 424/1.69 |
| 5,635,382 A | 6/1997 | Low et al. | 435/458 |
| 5,635,603 A | 6/1997 | Hansen et al. | 530/391.5 |
| 5,643,883 A | 7/1997 | Marchase et al. | 514/23 |
| 5,648,063 A | 7/1997 | Gries et al. | 424/9.363 |
| 5,670,132 A | 9/1997 | Griffiths et al. | 424/1.11 |
| 5,674,470 A | 10/1997 | Tweedle et al. | 424/9.363 |
| 5,684,149 A | 11/1997 | Morrow | 540/474 |
| 5,688,487 A | 11/1997 | Linder et al. | 424/1.65 |
| 5,688,488 A | 11/1997 | Low et al. | 424/1.69 |
| 5,716,596 A | 2/1998 | Dean et al. | 424/1.69 |
| 5,730,968 A | 3/1998 | Butterfield et al. | 424/78.37 |
| 5,820,847 A | 10/1998 | Low et al. | 424/9.1 |
| 5,830,431 A | 11/1998 | Srinivasan et al. | 424/1.69 |
| 5,834,266 A | 11/1998 | Crabtree et al. | 435/456 |
| 5,846,519 A | 12/1998 | Tweedle et al. | 424/9.363 |
| 5,847,121 A | 12/1998 | Yau et al. | 540/474 |
| 5,877,289 A | 3/1999 | Thorpe et al. | 530/387.1 |
| 5,880,281 A | 3/1999 | Argese et al. | 540/474 |
| 5,891,468 A | 4/1999 | Martin et al. | 424/450 |
| 5,904,915 A | 5/1999 | Fujibayashi et al. | 424/1.73 |
| 5,908,777 A | 6/1999 | Lee et al. | 435/320.1 |
| 5,951,964 A | 9/1999 | Dean et al. | 424/1.69 |
| 5,955,053 A | 9/1999 | Marzilli et al. | 424/1.11 |
| 5,955,605 A | 9/1999 | Axworthy et al. | 540/474 |
| 5,958,374 A | 9/1999 | Meares et al. | 424/1.65 |
| 5,977,163 A | 11/1999 | Li et al. | 514/449 |
| 5,986,074 A | 11/1999 | Marzilli et al. | 534/14 |
| 6,033,884 A | 3/2000 | Woo et al. | 435/455 |
| 6,054,436 A | 4/2000 | Crabtree et al. | 514/31 |
| 6,071,490 A | 6/2000 | Griffiths et al. | 424/1.49 |
| 6,071,533 A | 6/2000 | Papahadjopoulos et al. | 424/450 |
| 6,083,741 A | 7/2000 | Hart et al. | 435/320.1 |
| 6,096,874 A | 8/2000 | Wallace et al. | 534/10 |
| 6,113,946 A | 9/2000 | Szoka et al. | 424/486 |
| 6,143,274 A | 11/2000 | Tweedle et al. | 424/1.65 |
| 6,177,551 B1 | 1/2001 | Kasina | 534/10 |
| 6,187,286 B1 | 2/2001 | Elmaleh et al. | 424/1.73 |
| 6,197,278 B1 | 3/2001 | Blankenberg et al. | 424/1.69 |
| 6,232,295 B1 | 5/2001 | Kayyem et al. | 514/44 |
| 6,251,866 B1 | 6/2001 | Prakash et al. | 514/17 |
| 6,262,107 B1 | 7/2001 | Li et al. | 514/449 |
| 6,440,389 B1 | 8/2002 | Rabito | 424/9.6 |
| 6,521,209 B1 | 2/2003 | Meade et al. | 424/9.3 |
| 6,610,269 B1 | 8/2003 | Klaveness et al. | 424/9.1 |
| 6,613,305 B1 | 9/2003 | Collins et al. | 424/1.73 |
| 6,656,450 B2 | 12/2003 | Hubin et al. | 424/9.363 |
| 6,673,333 B1 | 1/2004 | Meade et al. | 424/9.35 |
| 6,692,724 B1 | 2/2004 | Yang et al. | 424/1.49 |
| 6,713,046 B1 | 3/2004 | Meade | 424/9.363 |
| 6,737,247 B2 | 5/2004 | Bogdanov et al. | 435/25 |
| 7,067,111 B1 | 6/2006 | Yang et al. | 424/9.1 |
| 7,121,926 B2 | 10/2006 | Sabde | 451/41 |
| 7,223,380 B2 | 5/2007 | Yang et al. | 424/9.4 |
| 7,229,604 B2 | 6/2007 | Yang et al. | 424/9.1 |
| 7,261,875 B2 | 8/2007 | Li et al. | 424/1.69 |
| 7,582,281 B2 | 9/2009 | Yang et al. | 424/9.1 |
| 7,615,208 B2 | 11/2009 | Yang et al. | 424/9.1 |
| 7,632,484 B2 | 12/2009 | Yang et al. | 424/1.65 |
| 2001/0034363 A1 | 10/2001 | Li et al. | 514/449 |
| 2001/0041189 A1 | 11/2001 | Xu | 424/488 |
| 2003/0013772 A1 | 1/2003 | Murphy et al. | 514/674 |
| 2003/0053954 A1 | 5/2003 | Meade et al. | 424/9.363 |
| 2003/0143235 A1 | 7/2003 | Cheesman et al. | 424/178.1 |
| 2003/0152512 A1 | 8/2003 | Rajopadhye et al. | 424/1.49 |
| 2003/0198597 A1 | 10/2003 | Meade et al. | 424/9.34 |
| 2003/0206865 A1 | 11/2003 | Platzek et al. | 424/9.363 |
| 2004/0029815 A1* | 2/2004 | Tidmarsh | A61K 31/70 514/23 |
| 2004/0166058 A1 | 8/2004 | Yang et al. | 424/9.3 |
| 2005/0024380 A1 | 2/2005 | Lin | 345/603 |
| 2005/0079133 A1* | 4/2005 | Yang et al. | 424/1.49 |
| 2005/0129619 A1 | 6/2005 | Yang et al. | 424/1.11 |
| 2006/0182687 A1 | 8/2006 | Yang et al. | 424/9.364 |
| 2006/0241018 A1 | 10/2006 | De Haen et al. | 530/328 |
| 2007/0009428 A1 | 1/2007 | Syud et al. | 424/1.11 |
| 2007/0248537 A1 | 10/2007 | Yang | 424/9.363 |

FOREIGN PATENT DOCUMENTS

| | | |
|---|---|---|
| JP | 10-307138 | 11/1998 |
| JP | 2002-516823 | 6/2002 |
| JP | 2002-522382 | 7/2002 |
| JP | 2002-241307 | 8/2002 |
| WO | WO 1991/016076 | 10/1991 |
| WO | WO 1999/056792 | 10/1991 |
| WO | WO 1995/028966 | 11/1995 |
| WO | WO 1997/033552 | 9/1997 |
| WO | WO 1998/008859 | 3/1998 |
| WO | WO 1998/048848 | 11/1998 |
| WO | WO 1999/027100 | 6/1999 |
| WO | WO 1999/039748 | 8/1999 |
| WO | WO 1999/049901 | 10/1999 |
| WO | WO 1999/061512 | 12/1999 |
| WO | WO 2000/045857 | 8/2000 |
| WO | WO 2000/053233 | 9/2000 |
| WO | WO 2000/061788 | 10/2000 |
| WO | WO 2001/049324 | 7/2001 |
| WO | WO 2001/072279 | 10/2001 |
| WO | WO 2001/079258 | 10/2001 |
| WO | WO 2001/080906 | 11/2001 |
| WO | WO 2001/088106 | 11/2001 |
| WO | WO 2001/091807 | 12/2001 |
| WO | WO 2001/097843 | 12/2001 |
| WO | WO 2002/006209 | 1/2002 |
| WO | WO 2002/011677 | 2/2002 |
| WO | WO 2002/024235 | 3/2002 |
| WO | WO 2002/039995 | 5/2002 |
| WO | WO 2002/043775 | 6/2002 |
| WO | WO 2002/056692 | 7/2002 |
| WO | WO 2003/009874 | 2/2003 |
| WO | WO 2003/051403 | 6/2003 |
| WO | WO 2003/086475 | 11/2003 |
| WO | WO 2004-044227 | 5/2004 |
| WO | WO 2004/062574 | 7/2004 |
| WO | WO 2006/016784 | 5/2006 |
| WO | WO 2006/074272 | 7/2006 |

OTHER PUBLICATIONS

Alauddin et al., "Evaluation of 9-[(3-18F]-fluoro-1-hydroxy-2-propoxy)methyl]guanine ([18F]-FHPG) in vitro and in vivo as probe for PET imaging of gene incorporation and expression in tumors," *Nucl. Med. Biol.*, 26:371-376, 1999.

Alauddin et al., "Receptor mediated uptake of a radiolabeled contrast agent sensitive to β-galactosidase activity," *Nucl. Med. Biol.*, 30:261-265, 2003.

Alauddin et al., "Synthesis of 9-[(3-18F]-fluoro-1-hydroxy-2-propoxy)methyl]guanine ([18F]-FHPG): a potential imaging agent of viral infection and gene therapy using PET," *Nucl. Med. Biol.*, 23:787-792, 1996.

Al-Kouraishi et al., "Labelling and quality control of gentamycin with 99m Technetium and biodistribution," *Journal of Radioanalytical and Nuclear Chemistry*, 125(1):203-211, 1988.

Alper et al., "Assessment of renal functional changes following transurethral prostatectomy suing tc-99m ethylenedicysteine," *J. Nuclear Med.*, 37:289P, Abstract No. 1292, 1996.

Anderson and Welch, "Radiometal-labeled agents (non-technetium) for diagnostic imaging," *Chem. Rev.*, 99:2219-2234, 1999.

Anderson et al., "Copper-64-labeled antibodies for PET imaging," *J. Nucl. Med.*, 33:1685-1691, 1992.

Anderson et al., "N,N'-ethylene-di-l-cysteine (ec) complexes of ga(III) and in (III): molecular modeling, thermodynamic stability and in vivo studies," *Nucl. Med. Biol.*, 22:165-173, 1995.

(56) References Cited

OTHER PUBLICATIONS

Anderson et al., "Preparation, biodistribution and dosimetry of copper-64-labeled anti-colorectal carcinoma monoclonal antibody fragments 1A3-F(ab')2," *J. Nucl. Med.*, 36:850-858, 1995.
Angello et al., "Effect of eating on thallium-201 myocardial redistribution after myocardial ischemia," *Am. J. Cardiol.*, 60:528-533, 1987.
Antony, "Folate receptors," *Ann. Rev.*, 16:501-521, 1996.
Aoi et al., "Globular carbohydrate macromolecule 'sugar balls' 3. 'radical-growth polymerization' of sugar-substituted α-amino acid N-carboxyanhydrides (glycoNCAs) with a dendritic initiator," *Tetrahedron, Elsevier Science Publishers*, 53(45):15415-15427, 1997.
Appelbaum et al., "The use of radiolabeled anti-CD33 antibody to augment marrow irridation prior to marrow transplantation for acute myelogenous leukemia," *Transplantation*, 54(5):829-833, 1992.
Auzeloux et al., "Technetium-99m radiolabelling of an N-aminoalkyl-benzamide nitrido-and oxo-technetium bis(aminoethanethiol) derivative syntesis and biological results. Potential melanoma tracer agents," *Journal of Labelled Compounds and Radiopharmaceuticals*, 42:567-579, 1999.
Baidoo and Lever, "Evaluation of a diaminedithiol-based bifunctional chelate for labeling small molecules with $^{99m}$Tc," in: Nicolini M., Bandoli G., Mazi U. eds. *Technetum and Rhenium in Chemsitry and Nuclear Medicine*, Verona, Italy: Cortina International, pp. 369-374, 1990.
Baidoo et al., "Synthesis of a new diaminedithiol bifunctional chelate for the preparation of nuetral technetium complexes," *J. Nuclear Med.*, 31:806, Abstract No. 414, 1990.
Bajorin et al., "Phase I Trial of Anti-GD3 Mouse Monoclonal Antibody (Mab) and IL-2 in Patients with melanoma," *Proc. Annu. Meet. Am. Soc. Clin. Oncol.*, 7:250, A967, 1988.
Bakker et al., "Receptor scintigraphy with a radioiodinated somatostatin analogue: radiolabeling, purification, biologic activity and in vivo application in animals," *J. Nucl. Med.*, 31:1501-1509, 1990.
Bar-Sever et al., "Comparison of living related donor and recipient renograms in predicting the early postransplantation course," *J. Nuclear Med.*, 37:292P, Abstract No. 1305, 1996.
Baselga et al., "Phase I studies of anti-epidermal growth factor receptor cheimeric antibody C225 alone and in combination with cisplatin," *J. Clinical Oncology*, 18(4):904-914, 2000.
Baselga et al., "Recombinant humanized anti-HER2 antibody (herceptin) enhances the antitumor activity of pacliltazel and doxorubicin against HER2/new overexpressing human breast cancer xenografts," *Cancer Research*, 58:2825-2831, 1998.
Becker et al., "Analysis of E-cadherin in diffuse-type gastric cancer using a mutation-specific monoclonal antibody," *American Journal of Pathology*, 155(6):1803-1809, 1999.
Benns et al., "Tailoring new gene delivery designs for specific targets," *Journal of Drug Targeting*, 8(1), Database Medline on STN International, Accession No. 2000222278, 2 pages, 2000.
Benveniste and Davies, "Aminoglycoside antibiotic-inactivating enzymes in actinomycetes similar to those present in clinical isolates of antibiotic-resistant bacteria," *Proc. Natl. Acad. Sci. USA*, 70:2276-2280, 1973.
Bertolini et al., "Angiogenic growth factors and endostatin in non-Hodgkin's lymphoma," *Br. J Haematol.*, 106:504-9, 1999.
Blair and Ghose., "Linkage of cytotoxin agents to immunoglobulins," *Journal of Immunological Methods*, 59:129-143, 1983.
Blakenberg et al., "Imaging of apoptosis (programmed cell death) with $^{99m}$Tc annexin V.," *J. Nucl. Med.*, 40:184-191, 1999.
Blankenberg et al., "Apoptosis: the importance of nuclear medicine," *Nucl. Med. Comm.*, 21:241-250, 2000.
Blankenberg et al., "In vivo detection and imaging of phosphatidylserine expression during programmed cell death," *Proc. Natl. Acad. Sci., USA*, 95:6349-6354, 1998.
Block, "Poly(g-benzyl-L-glutamate) and other glutamic acid containing polymers," Gordon and Breach Science Publishers, New York, 11-31, 1983.

Blondeau et al., "Dimerization of an intermediate during the sodium in liquid ammonia reduction of L-thiazolidine-4-carboxylic acid," *Can J. Chem*, 45:49-52, 1967.
Boersma et al., "Quantification of apoptotic cells with fluorescein isothiocyanate-labeled annexin V in Chinese hamster ovary cell cultures treated with cisplatin," *Cytometry*, 24:123-130, 1996.
Bohdiewicz et al., "Indium-111 satumomab pendetide: the first FDA-approved monoclonal antibody for tumor imaging," *J. Nuclear Medicine Technology*, 26(3):155-163, 1998.
Borchardt et al., "Targeted actinium-225 in vivo generators for therapy of ovarian cancer," *Cancer Research*, 63:5084-5090, 2003.
Bormans et al., "Synthesis and biological characteristics of the fourn stereoisomers of 99mTc-N, N'-bis-(mercaptoacetyl)2,3-diaminopropanoate," *Int. J. Rad. Appl. Instrum. B.*, 17(5);499-506, 1990.
Bormans et al., "Synthesis, radio-LC-MS analysis and biodistribution in mice of $^{99m}$Tc-Nim-Bat," *Journal of Labelled Compounds and Radiopharmaceuticals*, 46(6):575-585, 2003.
Borodina et al., "Metabolic network analysis of Streptomyces tenebrarius, a *Streptomyces* species with an active entner-doudoroff pathway," *Appl. Environ. Microb.*, 71:2294-2302, 2005.
Boschi et al., "A CD(4)/T(4) receptor peptide ligand labeled with technetium-99m: synthesis and biological activity," *Nucl. Med. Biol.*, 27:791-795, 2000.
Botta et al., "NMR relaxometric study of new Gd$^{III}$ macrocyclic complexes and their interaction with human serum albumin," *Organic & Biomolecular Chemistry*, 2:570-577, 2004.
Brechbiel et al., "Synthesis of 1 (P-isothiocyanatobenzyl) derivatives of DTPA and EDTA: antibody labeling and tumor-imaging studies," *Inorg. Chem.*, 25:2772-2781, 1986.
Brogi et al., "Hypoxia-induced paracrine regulation of vascular endothelial growth factor receptor expression," *J. Clin. Invest.*, 97(2):469-476, 1996.
Brokx et al., "Designing peptide-based scaffolds as drug delivery vehicles," *Science*, 78(1-3):115-123, 2002.
Brouwers et al., "Optimization of radioimmunotherapy of renal cell carcinoma: labeling of monoclonal antibody cG250 with $^{131}$I, $^{90}$I, $^{177}$Lu, or $^{186}$Re," *J. Nucl. Med.*, 45:327-337, 2004.
Budihardjo et al., "Biochemical pathways of caspase activation during apoptosis," *Annu. Rev. Cell Dev. Biol.*, 15:269-290, 1999.
Burgen, "Targets of drug action," *Ann. Rev. Pharmacol. Toxicol.*, 40:1-16, 2000.
Burian et al., "Angiogenic factors in laryngeal carcinomas: do they have prognostic relevance?," *Acta Otolaryngol.*, 119:289-292, 1999.
Bush et al., "Definitive evidence for hypoxic cells influencing cure in cancer therapy," *Br J Cancer*, (Suppl. III) 37:302-306, 1978.
Cafaggi et al., "Synthesis and antitumor activity of a new cis-diammineplatinum (III) complex containing procaine hydrochloride," *Anticancer Research*, 12:2285-2292, 1992.
Cammisuli et al., "SDZ 281-977: a modified partial structure of lavendustin A that exerts potent and selective antiproliferative activities in vitro and in vivo," *Int J Cancer*, 65:351-359, 1996.
Campbell et al., "Folate-binding protein is a marker for ovarian cancer," *Cancer Res*, 51:5329-5338, 1991.
Canet et al., "Kinetic characterization of CMD-A2-GD-DOTA as an intravascular contrast agent for myocardial perfusion measurement with MRI," *Magentic Resonance in Medicine*, 43:403-409, 2000.
Cao, "Therapeutic potentials of angiostatin in the treatment of cancer," *Haematologica*, 84:643-650, 1999.
Chakrabarti et al., "Interaction of the antitumor antibiotic chromomycin A3 with glutathione, a sulfhydryl agent, and the effect upon its DNA binding properties," *Biochemical Pharmacology*, 56:1471-1479, 1998.
Chapman et al., "Therapeutic antibody fragments with prolonged in vivo half-lives," *Nature Biotech.*, 17:780-783, 1999.
Chappell et al., "Synthesis, characterization, and evaluation of a novel bifunctional chelating agent for the lead isotopes $^{203}$Pb and $^{212}$Pb," *Nucl. Med. Biol.*, 27:93-100, 2000.
Chen et al., "Biological and pharmacokinetic evaluation of tc-99m ma2g2-b: a potential renal agent," *J. Nuclear Med.*, 35:263P, Abstract No. 1082, 1994.

(56) References Cited

OTHER PUBLICATIONS

Cherif et al., "Rapid synthesis of [$^{18}$F]Fluoro-1-(2'-Nitro-1'-Imidazolyl)-2-Propanol ([$^{18}$F]Fluoromisonidazole)," *Pharm Res.*, 11:466-469, 1994.

Chmura et al., "Electrophilic chelating agents for irreversible binding of metal chelates to engineered antibodies," *J. of Controlled Release*, 78:249-258, 2002.

Cleynhens et al., "Synthesis and biological evaluation in mice of a monoamide derivative of tc-99m-l,1-ec," *J. Nuclear Med.*, 38:186P, Abstract No. 799, 1997.

Collier et al. "Immunoscintigraphy performed with In-111-labeled CYT-103 in the management of colorectal cancer: comparison with CT," *Radiology*, 185:179-186, 1992.

Coney et al., "Chimeric murine-human antibodies directed against folate binding receptor are efficient mediators of ovarian carcinoma cell killing," *Cancer Res*, 54:2448-2455, 1994.

Connett et al., "Maximum tolerated dose and large tumor radioimmunotherapy studies of 64Cu-labeled monoclonal antibody 1A3 in a colon cancer model," *Clin. Cancer Res.*, 5(10 Suppl):3207s-3212s, 1999.

Connett et al., "Radioimmunotherapy with a 64Cu-labeled monoclonal antibody: a comparison with 67Cu," *Proc. Natl. Acad. Sci. USA*, 93:6814-6818, 1996.

Connors, "Anticancer drug development: the way forward," *The Oncologist*, 1:180-181, 1996.

Corlija et al., "Contribution of radiolytically induced dissociation of 99mtc-d, 1-hmpao in aqueous solutions," *J. Nuclear Med.*, 31:806, Abstract No. 413, 1990.

Corsi et al., "Inulin as a carrier for contrast agents in magnetic resonance imaging," *Chem.*, 7:64-71, 2001.

Craig et al., "Renal outcomes for children on year after urinary tract infection," *J. Nuclear Med.*, 37:46P, Abstract No. 175, 1996.

Cronin et al., "A new class of macrocycle capable of binding exogenous metals: synthesis, structure, magnetic and electrochemical properties of a Cu(II) trinuclear complex based upon 1,4,8,11-tetraazacyclotetradecane-2,3-dione [exoO(2)]cyclam," *J. Chem. Soc., Dalton Transactions*, 12:1925-1927, 1999.

Culver et al., "In vivo gene transfer with retroviral vector-producer cells for treatment of experimental brain tumors," *Science*, 256:1550-1552, 1992.

Cutler et al., "Dosimetry of copper-64-labeled monoclonal antibody 1A3 as determined by PET imaging of the torso," *J. Nucl. Med.*, 36:2363-2371, 1995.

Dagli et al., "Analysis of the complete dynamic scan data for camera-based determination of renal function," *J. Nuclear Med.*, 37:91P, Abstract No. 354, 1996.

Das et al., "[$^{186/188}$Re] rhenium-ethylene dicysteine (Re-Ec): preparation and evaluation for possible use in endovascular brachytherapy," *Nucl. Med. Biol.*, 27:189-197, 2000.

Davison et al., "A new class of oxotechnetium(5+) chelate complexes containing a TcON$_2$S$_2$ Core," *Inorg Chem*, 20:1629-1632, 1981.

De Klerk et al., "Aspirin versus captopril renography in the diagnosis of renal artery stenosis," *J. Nuclear Med.*, 37:289P, Abstract No. 1291, 1996.

Deguchi et al., "Retention of biologic activity of human epidermal growth factor following conjugation to a blood-brain barrier drug delivery vector via an extended poly(ethylene glycol) linker," *Bioconjugate Chem.*, 10:32-37, 1999.

DeNardo et al., "Enhancement of 67Cu-2IT-BAT-LYM-1 therapy in mice with human Burkitt's lymphoma (Raji) using interleukin-2," *Cancer*, 80(12 Suppl):2576-2582, 1997.

DeNardo et al., "Pharmacokinetics of chimeric L6 conjugated to indium 111- and yttrium-90-DOTA-peptide in tumor-bearing mice," *J. Nuclear Medicine*, 36:829-836, 1995.

DeNardo et al., "Yttrium-90/indoum-111-DOTA-peptide-chimeric L6: Pharmacokinetics, dosimetry and initial results in patients with incurable breast cancer," *Anticancer Research*, 17(3B):1735-1744, 1997.

Deutsch et al., "Synthesis of congeners and prodrugs, water-soluble prodrugs of taxol with potent antitumor activity," *J. Med. Chem.*, 32:788-792, 1989.

Deveraux and Reed, "IAP family proteins-suppressors of apoptosis," *Genes and Development*, 13:239-252, 1999.

Dewanjee et al., "Labeling antisense oligodeoxynucleotide (on) with tc-99m and hybridization with c-myc oncogene mrna in p388 leukemic cells," *J. Nuclear Med*, 35:263P, Abstract No. 1081, 1994.

Dezutter et al., "Preparation and biological evaluation of technetium-$^{99m}$-L,L-propylenedicysteine" *J. of Labelled Cpd. Radiopharm.*, 42:553-565, 1999.

Diamond et al., "Glycolysis in quiescent cultures of 3T3 cells. Stimulation by serum, epidermal growth factor, and insulin in intact cells and persistence of the stimulation after cell homogenization," *J. Biol. Chem.*, 253:866-871, 1978.

Dische, "A review of hypoxic-cell radiosensitization," *Int J Radiat Oncol Biol Phys*, 20:147-152, 1991.

Divgi et al., "Phase I and imaging trial of indium 111-labeled anti-epidermal growth factor receptor monoclonal antibody 225 in patients with squamous cell lung carcinoma," *J. National Cancer Institute*, 83(2):97-104, 1991.

Drapé et al., "Intraarticular diffusion of Gd-DOTA after intravenous injection in the kneww: MR imaging evaluation," *Radiology*, 188:227-234, 1993.

Drobnik et al., "Soluble synthetic polymers in biological systems," *Adv. Polym. Sci.*, 57:1-50, 1984.

Dunn et al., "Receptor-mediated endocytosis of epidermal growth factor by hepatocytes in the perfused rat liver: ligand and receptor dynamics," *J. Cell Biol.*, 98:2148-2159, 1984.

Eary et al., "Radiochemistry of halogenated antibodies," *Antibodies in Radiodiagnosis and Therapy*, Boca Ratan, Florida, CPC Press, 83-100, 1988.

Edreira et al., "Optimization of the small-scale synthesis of DOTA-Tyr$^3$-octreotide," *Nuclear Medicine Communications*, 23:493-499, 2002.

Eiseman et al., "Plasma pharmacokinetics and tissue distribution of paclitaxel in CD2F1 mice," *Cancer Chemother. Pharmacol.*, 34:465-471, 1994.

Eisenhut et al., "Synthesis and In Vivo Testing of a bromobutyl substituted 1,2-Dithia-5,9-diazacycloundecane: a versatile precursor for new $^{99m}$Tc-bis(aminoethanethiol) complexes," *Nucl. Med. Biol.*, 16:805-811, 1989.

Ellis and Sharma, "Co, Fe and Ga chelates for cell labelling: a potential use in PET imaging?" *Nuclear Medicine Communications*, 20:1017-1021, 1999.

Ennis et al., "Anti-epidermal growth factor receptor antibodies inhibit the autosrine-stimulated growth of MDA-468 human breast cancer cells," *Mol. Endocrinology*, 3(11):1830-1838, 1989.

Eshima et al., "Evaluating the role of protein binding on the renal extraction of tc-99m tubular agents utilizing an isolated perfused rat kidney model," *J. Nuclear Med.*, 37:47P, Abstract No. 178, 1996.

Ethier, "Growth factor synthesis and human breast cancer progression," *J. Natl. Cancer Inst.*, 87(13):964-973, 1995.

Fan et al., "Antitumor effect of anti-epidermal growth factor receptor monoclonal antibodies plus cis-diamminedichloroplatinum on well established A431 cell xenografts," *Cancer Research*, 53:4637-4642, 1993.

Fan et al., "Blockade of epidermal growth factor receptor function by bivalent and monovalent fragments of 225 anti-epidermal growth factor receptor monoclonal antibodies," *Cancer Research*, 53:4322-4328, 1993.

Fanciulli et al., "Glycolysis and growth rate in normal and in hexokinase-transfected NIH-3T3 cells," *Oncology Res.*, 6:405-409, 1994.

Fang et al., "Involvement of p21 Wafl in mediating inhibition of paclitaxel-induced apoptosis by epidermal growth factor in MDA-MB-468 human breast cancer cells," *Anticancer Research*, 20(1A):103-112, 2000.

Fidler et al., "The biology of cancer invasion and metastasis," *Adv. Cancer Res.*, 28:149-250, 1987.

Foa et al., "Taxol (paclitaxel): a novel anti-microtubule agent with remarkable anti-neoplastic activity," *J. Clin. Lab. Res.*, 24:6-14, 1994.

(56) References Cited

OTHER PUBLICATIONS

Frankel et al., "Targeted toxins," *Clin. Cancer Res.*, 6:326-334, 2000.

Franklin et al., "New anti-lung-cancer antibody cluster 12 reacts with human folate receptors present on adenocarcinoma," *Int J Cancer-Supplement*, 8:89-95, 1994.

Frisch and Screaton, "Anoikis mechanisms," *Curr. Opin. Cell Biol.*, 13:555-562, 2001.

Froidevaux et al., "Preclinical comparison in AR4-2J tumore bearing mice of four radiolabeled 1,4,7,10-tetraazacyclododecane-1,4,7,10-tetraacetic acid somatostatin analogs for tumor diagnosis and internal radiotherapy," *Endocrinology*, 141:3304-3312, 2000.

Fuertges et al., "The clinical efficacy of poly(ethylene glycol)-modified porteins," *J. Controlled Release*, 11:139-148, 1990.

Fuller et al., "A procedure for the facile synthesis of amino-acid N-carboxyanhydride," *Biopolymers*, 15:1869, 1976.

Gabizon, "Selective tumor localization and improved therapeutic index of anthracyclines encapsulated in long-circulating liposomes," *Cancer Research*, 52:891-896, 1992.

Gambhir et al., "A mutant herpes simplex virus type 1 thymidine kinase reporter gene shows improved sensitivity for imaging reporter gene expression with positron emission tomography," *Proc. Natl. Acad. Sci., USA*, 97(6):2785-2790, 2000.

Gambhir et al., "Imaging adenoviral-directed reporter gene expression in living animals with positron emission tomography," *Proc. Natl. Acad. Sci., USA*, 96:2333-2338, 1999.

Gambhir et al., "Imaging of adenoviral-directed herpes simplex virus type 1 thymidine kinase reporter gene expression in mice with radiolabeled ganciclovir.," *J. Nucl. Med.*, 39:2003-2011, 1998.

Garayoa et al., "Hypoxia-inducible factor-1 (HIF-1) up-regulates adrenomedullin expression in human tumor cell lines during oxygen deprivation: a possible promotion mechanism of carcinogenesis," *Molecular Endocrinology*, 14:848-862, 2000.

Gariepy and Kawamura "Vectorial delivery of macromolecules into cells using peptide-based vehicles," *Trends in Biotechnology*, 19(1):21-28, 2001.

Ginobbi et al., "Folic acid-polylysine carrier improves efficacy of c-myc antisense oligodeoxynucleotides on human melanoma (M14) cell," *Anticancer Research*, 17:29-36, 1997.

Girard, "Mechanisms by which carbohydrates regulate expression genes for clycolytic and lipogenic enzymes," *Ann. Rev. Nutr.*, 17:325-352, 1997.

Giraud et al., "Application to a cartilage targeting strategy: Synthesis and in vivo biodistribution of $^{14}$C-labelled quaternary ammonium-glucosamine conjugates," *Bioconjug. Chem.*, 11:212-218, 2000.

Goh et al., "Growth hormone promotion of tubulin polymerization stabilizes the microtubule network and protects against colchicine-induced apoptosis," *Endocrinology*, 139:4364-4372, 1998.

Goldenberg et al., "Imaging of human tumor xenografts with and indim-111-labeled anti-epidermal growth factor receptor monoclonal antibody," *J. National Cancer Institute*, 81:1616-1625, 1989.

Goldenberg, "Monoclonal antibodies in cancer detection and therapy," *Am. J. Med.*, 94:297-312, 1993.

Goldsmith et al., "Somatostatin receptor imaging in lymphoma," *Sem Nucl Med*, 25:262-271, 1995.

Goldsmith, "Receptor imaging: Competitive or complementary to antibody imaging," *Sem Nucl Med.*, 27:85-93, 1997.

Goldspeil, "Pharmaceutical issues: preparation, administration, stability, and compatibility owth other medications," *Ann. Pharocother.*, 28:S23-S26, 1994.

Gonda, "Aerosols for delivery of therapeutic and diagnostic agents to the respiratory tract," *Critical Reviews in Therapeutic Drug Carrier Systems*, 6(4):273-313, 1990.

Green and Evan, "A matter of life and death," *Cancer Cell*, 1:19-30, 2002.

Green and Wuts, "Protection for the Amino Group," *Protective Groups in Organic Synthesis*, New York: Wiley, Chapter 7, pp. 494-653, 1999.

Green and Wuts, "Protection for the Carbonyl Group," *Protective Groups in Organic Synthesis*, New York: Wiley, Chapter 4, pp. 293-368, 1999.

Green and Wuts, "Protection for the Carboxyl Group," *Protective Groups in Organic Synthesis*, New York: Wiley, Chapter 5, pp. 369-452, 1999.

Green and Wuts, "Protection for the Hydroxyl Group, Including 1,2- and 1,3-Diols," *Protective Groups in Organic Synthesis*, New York: Wiley Chapter 2, pp. 17-139, 1999.

Green and Wuts, "Protection for the Thiol Group," *Protective Groups in Organic Synthesis*, New York: Wiley, Chapter 6, pp. 454-493. 1999.

Green and Wuts, "The role of protective groups in organic synthesis," *Protective Groups in Organic Synthesis*, New York: Wiley, Chapter 1, pp. 1-16, 1999.

Greenfield et al., "In vitro evaluation of immunoconjugates prepared by linking mitomycin C to monoclonal antibodies via polyglutamic acid carriers," *Antibody, Immunoconjugates, and Radiopharmaceuticals*, 2(3):201-216, 1989.

Greenwald et al., "Drug delivery systems: water soluble tazol 2'-poly(ethylene glycol) ester prodrugs-design and in vivo effectiveness," *J. Med. Chem.*, 39:424-431, 1996.

Gregson et al., "meso-5,5,7,12,14-Hexamethyl-1,4,8,11-tetraazacyclotetradecane as a building block in supramolecular chemistry; salts formed with 2,2'-biphenol, 4,4'-thiodiphenol, 4,4'-sulfonyldiphenol, 3-and 4-hydroxybenzoic acids, 3,5-dihydroxybenzoic acid and phenylphosphonic acid; supramolecular structures in zero, one, two and three dimensions," *Acta Crystallogr.*, B56:39-57, 2000.

Griffiths et al., "$^{90}$Y-DOTA-hLL2: an agent for radioimmunotherapy of Non-Hodgkin's lymphoma," *J. Nucl. Med.*, 44:77-84, 2003.

Guo and Gallo, "Selective protection of 2', 2'-difluorodeoxcytidine (Gemcitabine)," *J Org Chem*, 64:8319-8322, 1999.

Guozheng and Boli, "A new potential renal imaging agent 99mtcn-ec," *J. Labelled compounds and Radiopharmaceuticals*, XXXVII:797-798, 1995.

Gutman et al., "Time to completed redistribution of thallium-201 in exercise myocardial scintigraphy: relationship to the degree of coronary artery stenosis," *Am. Heart J.*, 106:989-995, 1983.

Hadley et al, "Magnetic resonance imaging in acute head injury," *Clin. Rad*, 39:131-139, 1988.

Halpern et al., "Stability, characterization, and kinetics of In-labeled monoclonal antitumor antibodies in normal animals and nude mouse human tumor models," *Cancer Research*, 43:5347-5355, 1983.

Harada et al., "Insulin-induced egr-1 expression in chinese hamster ovary cells in insulin receptor an dinsulin receptor substrate-1 phosphorylation-independent," *J. Biol Chem.*, 270:26632-26638, 1995.

Hardy et al., "Neomycin inhibition of intestinal putrescine uptake," *Anticancer Res.*, 18(6A):4163-9, 1998.

Hay et al., "Hypoxia-selective antitumor agents. Bis(nitroimidazolyl)alkanecarboxamides: a new class of hypoxia-selective cytotoxins and hypoxic cell radiosensitizers," *J Med. Chem.*, 37:381-391, 1994.

Henson et al., "Gadolinium-enhanced CT angiography of the circle of Willis and neck," *AJNR Am. J. Neuroradiol.*, 25:969-972, 2004.

Hermann and Patel, "Adaptive recognition by nucleic acid aptamers," *Science*, 287:820-825, 2000.

Hermanson, "Amine detection reagents," *Bioconjugate Techniques*, San Diego, Academic Press, 112-114, 1996.

Hermanson, "Ellman's assay for the determination of sulfhydryls," *Bioconjugate Techniques*, Sand Diego, Academic Press, 88-90, 1996.

Hibi et al., "PGP9.5 as a candidate tumor marker for non-small-cell lung gancer," *American Journal of Pathology*, 155(3):711-715, 1999.

Hirsch et al., "PK11195, a ligand of the mitochondrial benzodiazepine receptor, facilitates the induction of apoptosis and reverses Bcl-2-mediated cytoprotection," *Experimental Cell Research*, 241:426-434, 1998.

(56) References Cited

OTHER PUBLICATIONS

Hjarnaa et al., "CHS 828, a novel pyridyl cyanoguanidine with potent antitumor activity in vitro and in vivo," *Cancer Res.*, 59:5751-5757, 1999.

Hnatowich et al., "Radioactive labeling of antibody: a simple and efficient method," *Science*, 220:613-615, 1983.

Hoelscher et al., "Effects of very high antibiotic concentrations on human intervertebral disc cell proliferation, viability, and metabolism in vitro," *Spine*, 25:1871-1877, 2000.

Hoes et al., "Optimization of macromolecular prodrugs of the antitumor antibiotic adriamycin," *J. Controlled Release*, 2:205-213, 1985.

Holm et al., "Folate receptor of human mammary adenocarcinoma," *APMIS*, 102:413-419, 1994.

Holmes et al., "Current status of clinical trials with paclitaxel and docetaxel, taxane anticancer agents: basic science and current status," *American Chemical Society*, Washington, DC, 31-57, 1995.

Honess et al., "Preclinical evaluation of the novel hypoxic marker $^{99m}$Tc-HL91 (prognox) in murine and xenograft systems in vivo," *Int. J. Radiation Oncology Biol. Phys.*, 42:731-735, 1998.

Hostetler and Hall, "Inhibition of kidney lysosomal phospholipases A and C by aminoglycoside antibiotics: possible mechanism of aminoglycoside toxicity," *PNAS*, 79:1663-1667, 1982.

Hsueh and Dolnick, "Altered folate-binding protein mRNA stability in KB cells grown in folate-deficient medium," *Biochem. Pharmacol.*, 45:2537-2545, 1993.

Hu, "Neomycin inhibits angiogenin-induced angiogenesis," *Proc. Natl. Acad. Sci. USA*, 95:9791-9795, 1998.

Hudecz et al., "Influence of carrier on biodistribution and in vitro cytotoxicity of methotexate-branched polypeptide conjugates," *Bioconjugate Chemistry*, American Chemical Society, 4(1):25-33, 1993.

Ilgan et al., "$^{99m}$Tc-ethylenedicysteine-folate: a new tumor imaging agent, synthesis, labeling and evaluation in animals," *Cancer Biotherapy & Radiopharmaceuticals*, 13(6):427-435, 1998.

Im et al., "Formation, properties, and characterization of a fully reduced Fe(II)Fe(II) form of spinach (and parsley) [2Fe—2S] ferredoxin with the macrocyclic complex [Cr(15-aneN(4))(H(2)O)(2)](2+) as reductant," *Inorg. Chem.*, 36:1388-1396, 1997.

Im et al., "The $Cr^{II}L$ reduction of [2Fe—2S] ferredoxins and site of attachment of $Cr^{III}$ using $^1H$ NMR and site-directed mutagenesis," *Inorg. Chem.*, 39:1755-1764, 2000.

Inoue et al., "Evaluation of In-111 DTPA-paclitaxel scintigraphy to predict response on murine tumors to paclitaxel," *Annals of Nuclear Medicine*, 13(3):169-174, 1999.

Inoue et al., "Paclitaxel enhances the effects of the anti-epidermal growth factor receptor monoclona antibody ImClone C225 in mice with metastatic human bladder transitional cell carcinoma," *Clinical Cancer Res.*, 6:4874, 4884, 2000.

Inoue et al., "The prognostic value of angiogenesis factor expression for predicting recurrence and metastasis of bladder cancer after neoadjuvant chemotherapy and radical cystectomy," *Clin. Cancer Res.*, 6:4866-4873, 2000.

International Search Report issued in PCT/US2001/18060, dated Jun. 21, 2002.

International Search Report issued in PCT/US2003/036078, dated Sep. 20, 2004.

International Search Report issued in PCT/US2006/16784, dated Sep. 25, 2006.

International Search Report issued in PCT/US2007/082411, dated Mar. 26, 2008.

Invitation to Pay Additional Fees and Partial Search Report issued in International Application PCT/US2007/072669, dated Apr. 7, 2008.

Ionov et al., "Mutational inactivation of the proapoptotic gene BAX confers selective advantage during tumor clonal evolution," *Proc. Natl. Acad. Sci., USA*, 97(20):10872-10877, 2000.

Irie and Morton "Regression of cutaneous metastic melanoma by inralesional injection with human monoclonal antibody to ganglioside GD2," *Proc. Natl. Acad. Sci., USA*, 83:8694-8698, 1986.

Ito et al., "PET and planar imaging of tumor hypoxia with labeled metronidazole," *Acad. Radiol.*, 13:598-609, 2006.

Itoh et al., "Graphic (patlak) method in tc-99m-mag3 renal scintigraphy: noninvasive calculation of extraction fraction (ef) and renal plasma flow (RPF)," *J Nuclear Med.*, 37:291P, Abstract No. 1300, 1996.

Iyer et al., "8-[18F]Fluoropenciclovir: an improved reporter probe for imaging HSV1-tk reporter gene expression in vivo using PET," *J. Nucl. Med.*, 42(1):96-105, 2001.

Jamar et al., "Clearance of the new tubular agent Tc-99m L,L-ethylenedicysteine: Estimation by a simplified method," *J Nucl Med*, 34:129P, 1993.

Jamar et al., "Clinical evaluation of Tc-99m L,L-ethylenedicysteine, a new renal tracer, in transplanted patients," *J Nucl Med*, 34:(Abstract 514), 1993.

Jeppesen et al., Impact of polymer tether length on multiple ligand-recepotor bond formation, *Science*, 293:465-468, 2001.

Jiang et al., "3-(Iodoacetamido)-benzoylurea: a novel cancericidal tubulin ligand that inhibits microtubule polymerization, phosphorylates bcl-2, and induces apoptosis in tumor cells," *Cancer Res.*, 58:5389-5395, 1998.

Jiang et al., "Antitumor activity of didemnin B in the human tumor stem cell assay," *Cancer Chemother Pharmacol*, 11:1-4, 1983.

John et al., "Tc-99m labeled ethylenediamines: quest for sigma receptor chelates," *J. Nuclear Med.*, 38:186P, Abstract No. 798, 1997.

Jones and Mayer, "Glucose metabolism in the rat small intestine: the effect of glucose analogues on hexokinase activity," *Biochem. J*, 132:125-128, 1973.

Jurisson et al., "Potential technitium small molecule radiopharmaceuticals," *Chem. Rev.*, 99:2205-2218, 1999.

Kabasakal et al., "Clinical comparison of technetium-$^{99m}$-ec, technetium $^{99m}$-MAG3 and iodine-131-OIH in renal disorders," *J. Nucl. Med.*, 36(2):224-228, 1995.

Kabasakal et al., "Evaluation of technetium-99m-ethylenedicysteine in renal disorders and determination of extraction ratio," *J. Nucl. Med.*, 36(8):1398-1403, 1995.

Kabasakal et al., "Prospective validation of single plasma sample $^{99m}$Tc-ethylenedicysteine clearance in adults," *J. Nucl. Med.*, 40:429-431, 1999.

Kabasakal et al., Simplified technetium-$^{99m}$-EC clearance in adults from a single plasma sample, *J. Nuclear Med.*, 38:1784-1786,1997.

Kabasakal. "Technetium-99m ethylene dicysteine: a new renal tubular function agent," *Eur. J Nucl. Med.* 27:351-357, 2000.

Kanazawa et al., "19F NMR of 2-deoxy-2-fluro-D-glucos for tumor diagnosis in mice. An NDP-bound hexose analog as a new NMR target for imaging," *NMR in Biomed.*, 10:35-41, 1997.

Kanvinde et al., "Technetium-99m-γ-pyrones: a new class of tc-99m cationic complexes," *J. Nuclear Medicine*, 31:908, Abstract, 1990.

Kao et al., "Detection of esophageal carcinoma susing Tc-99m MIBI SPECT imaging," *Clin. Nucl. Med.*, 19(12):1069-1074, 1994.

Kao et al., "Relationship of alveolar permeability and lung inflammation in patients with active diffuse infiltrative lung disease detected by 99Tcm-DTPA radioaerosol inhalation lung scintigraphy and quantitative 67Ga lung scans," *Nucl. Med. Commun.*, 15(10):850-854, 1994.

Kao et al., "Role of radioisotope penile plethysmigraphy in the evaluation of penile hemodynamic of impotent patients," *J. Nuclear Med.*, 37:292P, Abstract No. 1304, 1996.

Kao et al, "Tc-99m MIBI uptake in breast carcinoma and axillary lymph node metastases," *Clin. Nuc. Med.*, 19(10):898-900, 1994.

Kao et al., "Technetium-99m methoxyisobutylisonitrile chest imaging of small cell lung carcinoma," *Cancer*, 83:64-68, 1998.

Kato and Sugiyama, "Targeted delivery of peptides, proteins, and genes by receptor-mediated endocytosis," *Critical Reviews in Therapeutic Drug Carrier Systems*, 14(3):287-331, 1997.

Kato et al., "A novel method of conjugation of daunomycin with antibody with a poly-L-glutamic acid-a-fetoprotien antibody-daynomycin conjugate," *J. Med. Chem.*, 27:1602-1607, 1984.

(56) References Cited

OTHER PUBLICATIONS

Kengen, "Good results of tc-99m-mag3 clearance measurements with a dual headed gamma camera without plasma sampler," *J. Nuclear Med.*, 37:91P, Abstract No. 353, 1996.
Kikukawa et al., "Early and delayed Tc-99m ECD brain SPECT in SLE patients with CNS involvement," *Ann Nucl Med.* 14:25-32, 2000.
Kim et al., "Synthesis, biodistribution and imaging of mammary tumors using 99mtc-ec-polyglutamate; a glutamate receptor peptide," *J. Nuclear Medicine*, 41:231P Abstract, 2000.
King et al., "Imaging of bone infection with labelled white blood cells: role of contemporaneous bone marrow imaging," *European Journal of Nuclear Medicine*, 17:148-151, 1990.
Kitamura and Shibata, "Preparation and the covalent hydration of a hexafluoro-2,4-pentanedionatotetraaminecobalt(III) complex," *Inorganica Chimica Acta*, 203:37-42, 1993.
Kitamura et al., "Chemical engineering of the monoclonal antibody A7 by polyethylene clycol for targeting cancer chemotherapy," *Cancer Research*, 51:4310-4315, 1991.
Klok et al., "Star-shaped fluorescent polypeptides," *Journal of Polymer Science*, 39(10):1572-1582, 2001.
Knight et al, "Thrombus imaging with technetium—99m synthetic peptides based upon the binding domain of a monoclonal antibody to activated platelets," *J. Nucl. Med.*, 35(2):282-288, 1994.
Knight et al., "Radiolabeling of fibrinogen using the lodogen technique," *Thromb. Haemost*, 46(3):593-596, 1981.
Koh et al., "Imaging of hypoxia in human tumors with [F-18]fluoromisonidazole," *Int J Radiat Oncol Biol Phys*, 22:199-212, 1992.
Kopecek and Kopeckova, "Targetable water-soluble polymeric antcancer drugs: achievements and unsolved problems," *Proc. Intern. Symp. Conol. Rel. Bioact. Mater.*, 20:190-191, 1993.
Kopecek et al. "Targetable polymeric prodrugs," *J. Control. Release*, 6:315-327, 1987.
Kopecek, "The potential of water-soluble polymeric carriers in targeted and site-specific drug delivery," *Journal of Controlled Release*, 11:279-290, 1990.
Kranz et al., "Conjugates of folate and anti-T-cell-receptor antibodies specifically target folate-receptor-positive tumor cells for lysis," *Proc Natl Acad Sci*, 92:9057-9061, 1995.
Kundra et al., "Noninvasive monitoring of somatostatin receptor type 2 chimeric gene transfer," *J. Nucl. Med.*, 43:406-412, 2002.
Kung et al., "Synthesis of new bis(aminoethanethiol) (BAT) derivatives: possible ligands for 99mTc brain imaging agents," *J. Med. Chem.*, 28:1280-1284, 1985.
Laissy et al., "Functional evaluation of normal and ischemic kidney by means of gadolinium-DOTA enhanced TurboFLASH MR imaging: a preliminary comparison with 99Tc-MAG3 dynamic scintigraphy," *Magn. Reson. Imaging*, 12:413-419, 1994.
Lamberts et al., "Somatostatin receptor imaging in vivo localization of tumors with a radiolabeled somatostatin analog," *J. Steoid Biochem Mol Biol*, 37:1079-1082, 1990.
Lamki, "Radioimmunoscintigraphy of cancer: problems, pitfalls, and prospects," *Nuclear Medicine Annual* 1990, New York, Raven Press Ltd., 113-150, 1990.
Larson et al., "Overview of clinical radioimmunodetection of human tumors," *Cancer*, 73(supp):832-835, 1994.
Leamon and Low, "Cytotoxicity of momordin-folate conjugates in cultured human cells," *J Biol Chem*, 267:24966-24971, 1992.
Leamon and Low, "Delivery of macromolecules into living cells: a method that exploits folate receptor endocytosis," *Proc Natl Acad Sci*, 88:5572-5576, 1991.
Leamon et al., "Cytotoxicity of folate-pseudomonas exotoxin conjugates toward tumor cells," *J Biol Chem*, 268:24847-24854, 1993.
LeClerc and Cedergren, "Modeling RNA-ligand interactions: the rev-binding element RNA-aminoglycoside complex," *J Med Chem*, 41:175-182, 1998.
Lee and Low, "Delivery of liposomes into cultured KB cells via folate receptor-mediated endocytosis," *J Biol Chem*, 269:3198-3204, 1994.

Lewis et al., "Conjugation of monoclonal antibodies with TETA using activated esters: biological comparison of 64Cu-TETA-1A3 with 64Cu-BAT-2IT-1A3," *Cancer Biother. Radiopharm.*, 16:483-94, 2001.
Li et al., "A calcium-sensitive magnetic resonance imaging contrast agent," *J. Am. Chem. Soc.*, 121(6):1413-1414, 1999.
Li et al., "Antitumor activity of poly (L-glutamic acid)-paclitaxel on syngeneic and xenografter tumors," *Clinical Cancer Res.*, 5:891-897, 1999.
Li et al., "Complete regression of well-established tumors using a novel water-soluble poly(L-glutamic acid)-paclitaxel conjugate," *Cancer Res.*, 58:2404-2409, 1998.
Li et al., "N,N'Ethylenedi-$_L$-cysteine (EC) and its metal complexes: synthesis, characterization, crystal structures, and equilibrium constants," *Inorg. Chem.*, 35:404-414, 1996.
Li et al., "Poly(L-glutamic acid)-anticancer drug conjugates," *Advanced Drug Delivery Rev.*, 54:695-713, 2002.
Li et al., "Synthesis and evaluation of water-soluble polyethylene glycol paclitaxel conjugate as a paclitaxel prodrug," *Anticancer Drugs*, 7(5):642-648, 1996.
Li et al., "Synthesis, metal chelate stability studies, and enzyme digestion of a peptide-linked DOTA derivative and its corresponding radiolabeled immunoconjugates," *Bioconjugate Chem.*, 4:275-283, 1993.
Li et al., "Vinyl sulfone bifunctional derivatives of DOTA allow sulfhydryl- or amino-directed coupling to antibodies. Conjugates retain immunoreactivity and have similar biodistributions," *Bioconjugate Chem.*, 13:110-115, 2002.
Liang et al., "The use of diaminodithiol for labeling small molecules with technetium-99m," *Nucl. Med. Biol.*, 14:63-67, 1987.
Lin et al., "The role of Tc-99m MDP and Ga-67 imaging in the clinical evaluation of malignant fibrous histiocytoma," *Clin. Nucl. Med.*, 19(11):996-1000, 1994.
Liu et al., "99mTc-labeled small peptides as diagnostic radiopharmaceuticals," *Chem. Rev.*, 99:2235-2268, 1999.
Liu et al., "Apoptotic signals delivered through the T-cell receptor of a T-cell hybrid require the immediate-early gene nur77," *Nature*, 367(6460):281-284, 1994.
Liu et al., "Bifunctional chelators for therapeutic lanthanide radiopharmaceuticals," *Bioconjugate Chemistry*, 12:7-34, 2001.
Liu et al., "Detection of anaerobic odontogenic infections by fluorine-18 fluoromisonidazole," *Eur. J. Nucl. Med.*, 23(10):1384-1387, 1996.
Liu et al., "Induction of apoptosis and activation of the capase cascade by anti-EGF receptor monoclonal antibodies in DiFI human colon cancer cells do not involve the C-jun N-terminal kinase activity," *British Journal of Cancer*, 82(12):1991-1999, 2000.
Lu et al., "Polymerizable fab' antibody fragments for targeting of anticancer drugs," *Nat. Biotech.*, 17:1101-1104, 1999.
Lu, "Antimitotic agents," In: Foye, WO. Ed., "Cancer chemotherapeutic agents," Washington, DC: American Chemical Society, 345-368, 1995.
Luckay et al., "Synthesis and structure of a complex of bismuth(III) with nitrogen donor macrocycle," *Journal of the Chemical Society, Chem. Comm.*, 2365-2366, 1995.
Lundberg et al., "Conjugation of an anti-B-cell lymphoma monoclonal antibody, LL2, to long-circulating drug-carrier lipid emulsions," *J Pharm Pharmacol*, 51:1099-1105, 1999.
Macapinlac et al., "Gallium-67-citrate imaging in nuclear oncology," Nucl. Med. Biol., 21(5):731-738, 1994.
Maeda et al., "Tumoritropic and lymphotropic principles of macromolecular drugs," *Crit. Rev. Ther. Drug Carrier Syst.*, 6(3):193-210, 1989.
Maeda, "SMANCS and polymer-conjugated macromolecular drugs: advantages in cancer chemotherapy," *Adv. Drug Delivery Rev.*, 6(2):181-202, 1991.
Makin and Hickman, "Apoptosis and cancer chemotherapy," *Cell Tissue Res.*, 301:143-152, 2000.
Mang'era and Verbruggen, "Synthesis and evaluation of beta-homocysteine derivatives of 99mtc-l,1-ec and 99mtc-l,1-ecd," *J. of Labelled Compounds and Radiopharmaceuticals*, 42:743-750, 1999.

(56) References Cited

OTHER PUBLICATIONS

Mann et al., "Molecular amplifiers: synthesis and functionalization of a poly(aminopropyl dextran bearing a uniquely reactive terminus for univalent attachment to biomolecules," *Bioconjugate Chemistry*, 3:154-159, 1992.
Marti and Risau, "Systematic hypoxia changes the organ-specific distribution of vascular endothelial growth factor and its receptors," *Proc. Natl. Acad. Sci., USA*, 95:15809-15814, 1998.
Martin et al., "Enhanced binding of the hypoxic cell marker [$^3$H]fluoromisonidazole in ischemic myocardium,"*J Nucl Med*, 30:194-201, 1989.
Martin et al., "Noninvasive detection of hypoxic myocardium using fluorine-18 fluoromisonidazole and positron emission tomography," *J. Nucl. Med.*, 33(12):2202-2208, 1992.
Mason et al., "99mtc-desferoxamine: production, stability and solute clearance measurements after aerosolization," *J. Nuclear Med.*, 31:908, Abstract No. 865, 1990.
Masui et al., "Growth inhibition of human tumor cells in athymic mice by anti-epidermal growth factor receptor monoclonal antibodies," *Cancer Research*, 44:1002-1007, 1984.
Mather et al., "Tumour cell uptake of technetium dithiocarbamate complexes," *J. Nuclear Med.*, 38:186P, Abstract No. 797, 1997.
Mathew et al., "Synthesis and evaluation of some water-soluble prodrugs and derivatives of taxol with antitumor activity," *J. Med. Chem.*, 35:145-151, 1992.
Mathias et al., "Indium-111-DTPA-folate as a radiopharmaceutical for targeting tumor-associated folate binding protein," *J Nucl Med*, (Supplement) 38:133P, 1997.
Mathias et al., "Synthesis of Tc-99m-DTPA-folate and preliminary evaluation as a folate-receptor-targeted radiopharmaceutical," *J Nucl Med*, (Supplement); 38:87P, 1997.
Mathias et al., "Tumor-selective radiopharmaceudcal targeting via receptor—mediated endocytosis of Gallium- 67-deferoxamine-folate," *J Nucl Med*, 37:1003-1008, 1996.
McGahon et al., "Chemotherapeutic drug-induced apoptosis in human leukaemic cells is intependent of the Fas (APO-1/CD95) receptor/ligand system," *British Journal of Haematology*, 101:539-547, 1998.
Meares et al., "Macrocyclic chelates of radiometals for diagnosis and therapy," *British J. Cancer*, 62:21-26, 1990.
Mease et al., "Comparison of renal agents for detecting unilateral acute ischemic/reperfusion renal injury in rats," *J. Nuclear Med.*, 36:231P, Abstract No. 1033, 1995.
Mendelsohn et al., "Anti-epidermal growth factor recepotr monoclonal antibodies may inhibit A431 tumor cell proliferation by blocking autocrine pathway," *Trans. Assoc. Am. Phys.*, 100:173-178, 1987.
Mendelsohn, "Epidermal growth factor receptor inhibition by a monoclonal antibody as anticancer therapy," *Clinical Cancer Research*, 3:2703-2707, 1997.
Meredith et al., "Treatment of metastatic prostate carcinoma with radiolabeled antibody CC49," *J. Nucl. Med.*, 35(6):1017-1022, 1994.
Meyer et al., "Tryptophan hydrolase antibodies used in the diagnosis of carcinoid," *Hepato-Gastroenterology*, 45:1522-1526, 1998.
Michalik et al., "Effect of various aminoglycoside antibiotics on glucose formation in isolated rabbit kidney-cortex tubules ,"*Pharmacol. Res.*, 21:405-414, 1989.
Michiels et al., "Simultaneous estimation of effective renal plasma flow and glomerular filtration rate using tc-99m-ec.," *J. Nuclear Med.*, 37:91P, Abstract No. 355, 1996.
Milross et al., "Relationship of mitotic arrest and apoptosis to antitumor effect of paclitaxel,"*J. National Cancer Institute*, 88(18):1308-1314, 1996.
Mitchell et al., "Active-specific immunotherapy for melanoma," *J. Clin. Oncol.*, 8(5):856-869, 1990.
Mochizuki et al., "Synthesis of poly-L-glutamates containing 5-substituted uracil moieties," *Nucleic Acids Symp. Ser.*, 16:121-124, 1985.
Modjahedi et al., "The receptor for EGF and its ligands: expression, prognostic value and target for therapy in cancer (review)," *Int. J. Oncology*, 4(2):277-296, 1994.
Moller et al., "Biologic activities of naturally occurring human insulin receptor mutations," *J Biol. Chem.*, 266:10995-11001, 1991.
Moran, "Technetium-$^{99m}$-EC and other potential new agents in renal nuclear medicine," *Seminars in Nucl. Med.*, 29: 91-101, 1999.
Morton et al., "Comparison of 2-point postural drainage with diuresis renography in the assessment hydronephrosis," *J. Nuclear Med.*, 37:46P, Abstract No. 174, 1996.
Morton et al., "Prolongation of survival in metastatic melanoma after active specific immunotherapy with a new polyvalent melanoma vaccine," *Ann. Surg.*, 216(4):463-482, 1992.
Mosmann, "Rapid colorimetic assay for cellular growth and survival: application to proliferation ans cytotoxicity assay," *J. Immunol. Methods*, 65:55-63, 1983.
Mrhac et al., "Abnormal first-pass flow through the azygos vein from valsalva maneuver," *Clinical Nucl. Med.*, 21:331-332, 1996.
Murakami et al., "Calcium hydroxide ameliorates tobramycin toxicity in cultured chick tibiae," *Bone*, 21:411-418, 1997.
Murakami et al., "Interaction of tobramycin and pH in cultured chick tibiae," *J. Orthop. Res.*, 14:742-748, 1996.
Murray et al., "Matrix metalloproteinase-1 is associated with poor prognosis in oesophageal cancer," *Journal of Pathology*, 185:256-261, 1998.
Myszka et al., "Synthesis and induction of apoptosis in B cell chronic leukemia by diosgenyl 2-amino-2-deoxy-beta-D-glucopyranoside hydrochloride and its derivatives," *Carb. Res.*, 338:133-141, 2003.
Nakae and Nakae, "Diffusion of aminoglycoside antibiotics across the outer membrane of *Escherichia coli,"* *Antimicrobial Agents and Chemo.*, 22:554-559, 1982.
Namavari et al., "Synthesis of 8-[18F]Fluoroguanin derivatives: in vivo probes for imaging gene expression with positron emission tomography," *Nucl. Med. Biol.*, 27:157-162, 2000.
Nicolaou et al., "Design, synthesis, and biological activity of protaxols," *Nature*, 364:464-466, 1993.
Nordsmark et al., "Pretreatment oxygenation predicts radiation response in advanced squamous cell carcinoma of the head and neck," *Radiotherapy and Oncology*, 41:31-39, 1996.
Nosco et al., "Development of a kit formulation for 99mtcmag3 of very high purity and very high stability," *J. Nuclear Med.*, 31:908, Abstract No. 863, 1990.
Office Action issued in Japanese Patent Application No. 2004-552132 dated Mar. 17, 2009. (English Translation).
Office Action, issued in U.S. Appl. No. 10/732,919, dated Apr. 8, 2009.
Office Action, issued in U.S. Appl. No. 10/732,919, dated Jan. 4, 2007.
Office Action, issued in U.S. Appl. No. 10/732,919, dated Nov. 5, 2007.
Office Action, issued in U.S. Appl. No. 10/732,919, dated Oct. 2, 2008.
Office Action, issued in U.S. Appl. No. 11/405,334, dated Dec. 11, 2008.
Office Action, issued in U.S. Appl. No. 11/405,334, dated Mar. 27, 2008.
Office Action, issued in U.S. Appl. No. 11/405,334, dated Mar. 18, 2009.
Office Action, issued in U.S. Appl. No. 11/627,299, dated Feb. 25, 2009.
Office Action, issued in U.S. Appl. No. 11/627,299, dated May 29, 2008.
Office Action, issued in U.S. Appl. No. 11/760 , dated Jul. 8, 2008. 456.
Office Action, issued in U.S. Appl. No. 11/760,456, dated Nov. 13, 2008.
Office Communication issued in European Patent Application No. 07799253, dated Mar. 7, 2011.
Office Communication issued in U.S. Appl. No. 11/737,694, dated Sep. 22, 2010.
Office Communication issued in U.S. Appl. No. 11/737,694, dated Nov. 23, 2010.

(56) References Cited

OTHER PUBLICATIONS

Office Communication issued in U.S. Appl. No. 11/737,694, dated Apr. 28, 2011.
Office Communication issued in U.S. Appl. No. 12/563,724, dated Jul. 12, 2011.
Offield et al., "PDX-1 is required for pancreatic outgrowth and differentiation of the rostral duodenum," *Development*, 122:983-995, 1996.
Ohtsuki et al., "Technetium-99m HYNIC-annexin V: a potential radiopharmaceutical for the in-vivo detection of apoptosis," *Eur. J. Nucl. Med.*, 26:1251-1258, 1999.
Oldham et al., "Comparison of action of paclitaxel and poly (L-glutamic acid)-paclitaxel conjugate in human breast cacner cells," *Int. J. Oncol.*, 16(1):125-132, 2000.
Omelyanenko et al., "HPMA copolymer-anticancer drug-OV-TL16 antibody conjugates: influence of synthesis on the binding affinity to OVCAR-3 ovarian carcinoma cells in vitro," *J. Drug Targeting*, 3:357-373, 1996.
Omelyanenko et al., "HPMA copolymer-anticancer drug-OV-TL16 antibody conjugates II. Processing in epithelial ovarian carcinoma cells in vitro," *International Journal of Cancer*, 75(4):600-608, 1998.
Orr et al., "Similarity of folate receptor expression in UMSCC 38 cells to squamous cell carcinoma differentiation markers," *Natl. Cancer Inst.*, 87:299-303, 1995.
Ozaki et al., "Assesment of tumor imaging using $^{99m}$Tc-LA-beled guanine analogue," *The Journal of Nuclear Medicine*, 44(Suppl. 5):298P(Abstract 1067), 2003.
Ozanne et al., "Over-expression of the EGF receptor is a hallmark of squamous cell carcinomas," *J. Pathol*, 149:9-14, 1986.
Ozker et al., "Technetium-$^{99m}$-N,N-ethylenedicysteine-a comparative study of renal scintigraphy with technetium-$^{99m}$-MAG3 and iodine-131-OIH in patients with obstructive renal disease," *J. Nucl. Med.*, 35:840-845, 1994.
Ozmen et al., "Effects of some antibiotics on activity of glucose-6-phosphate dehydrogenase from human erythrocytes in vitro and effect of isepamicin sulfate on activities of antioxidant enzymes in rat erythrocytes," *Drug Chem. Toxicol.*, 28:433-445, 2005.
Palyi et al., "Effects of methylacetylenic putrescine, and ornithine decarboxylase inhibitor and potential novel anticancer agent, on human and mouse cancer cell lines," *Anti-Cancer Drugs*, 10:103-111, 1999.
Panneerselvam et al., "(12-hydroxymethyl-5,5,7,12,14-pentamethyl-1,4,8,11-tetraazacyclo-tetradecane-N-acetato-N,N', N'', N''', O,O')cobalt(III) chloride perchlorate monohydrate," *Acta Crystallogr., C* 56:659-660, 2000.
Pavicevic et al., "Serum tumor marker CYFRA 21-1 in the diagnostics of NSCLC lung cancer," *Coll Antropol*, 22(2):629-635, 1998.
Pavlik et al., "Properties of anticancer agents relevant to in vitro determinations of human tumor cell sensitivity," *Cancer Chem other Pharmacol*, 11:8-15, 1983.
PCT International Search Report and Written Opinion issued in Application No. PCT/US2007/072669, dated Jan. 13, 2009.
Pedley et al., "The potential for enhanced tumour localisation by poly(ethylene glycol) modification of anti-CEA antibody," *British J. Cancer*, 70:1126-1130, 1994.
Petrak et al., "Transport of macromolecules across the capillary walls," *Adv. Drug Deliv. Review*, 3:191-214, 1989.
Phillips-Hughes et al., "Restenosis: pathophysiology and preventive strategies," *JVIR*, 7:321-333, 1996.
Philpott et al., "RadioimmunoPET: detection of colorectal carcinoma with positron-emitting copper-64-labeled monoclonal antibody," *J. Nucl. Med.*, 36:1818-1824, 1995.
Pietersz et al., "Specific in vitro anti-tumor activity of methotrexate-monoclonal antibody conjugates prepared using human serum albumin as an intermediary," *Immunol. Cell Biol.*, 66:43-49, 1988.
Pimm et al., "Differences in tumor and normal tissue concentrations of iodine and indium labeled monoclonal antibody II: biodistribution studies in mice with human tumor xenografts," *Dur. J. Nucl. Med.*, 11:300-304, 1985.
Pimm et al., "Strategies for labelling branched polypeptides with a poly (L-Lysine) backbone with radioiodines 123I, 125I, 131I) and radiometals (111In, 51Cr) for biodistribution studies wnad radiopharmaceutical development," *Journal of Labelled Compunds and Radiopharmaceuticals*, 36(2):157-172, 1995.
Piper et al., "A synthetic approach to poly(γ-glutamyl) conjugates of methotrexate," *J. Med. Chem.*, 26:291-294, 1983.
Pirmettis et al., "Synthesis and characterization of the tcd(ec) complex, a renal imaging agent," *J. Nuclear Med.*, 35:263P, Abstract No. 1079, 1994.
Pohost et al., "Differentiation of transiently ischemic from infarcted myocardium by serial imaging after a single dose of thallium-201 ," *Circulation*, 55:294-302, 1977.
Popovici et al., "The influence of some antibiotics on hexokinase and pyruvate-kinase activity in the rat liver and kidney," *Arch. int. Pharmacodyn*, 193:80-86, 1971.
Potamianos et aL, "Radioimmunoscintigraphy and radioimmunotherapy in cancer: principles and application," *Anticancer Research*, 20(2A):925-948, 2000.
Prvulovich et al., "Clinical evaluation of technetium-$^{99m}$-L,L-ethylenedicysteine in patients with chronic renal failure," *J. Nucl. Med.*, 38:809-814, 1997.
Putnam and Kopecek, "Polymer conjugates with anticancer activity," *Polymer Science*, 122:55-123, 1995.
Qu et al., "Technetium-99m labeling on monoclonal antibodies via N,N'-ethylen-bis-L-cysteine," *Radiochimica Acta*, 63:209-212, 1993.
Quadri et al., "Effects of linker chemistry on the pharmacokinetics of radioimmunoconjugates," *Quart. J. Nucl., Med.*, 42:250-261, 1998.
Raffauf et al., "Colchicine. Derivatives of trimethylcolchicinic acid," *J. Am Chem Soc*, 75:5292-5294, 1953.
Ranganathan et al., "Polymethylated DOTA ligands. 2. synthesis of rigified lanthanide chelates and studies on the effect of alkyl substitution on conformational mobility and relaxivity," *Inorg. Chem.*, 41:6856-6866, 2002.
Rasey et al., "Characterization of the binding of labeled fluoromisonidazole in cells in vitro," *Radiat Res*, 122:301-308, 1990.
Rasey et al., "Radiolabeled fluoromisonidazole as an imaging agent for tumor hypoxia," *Int. J Radiat Oncol. Biol Phys*, 17:985-991, 1989.
Ramer and Clarke, "The action of formaldehyde upon cysteine," *J. Am Chem. Soc.*, 59:200-206, 1937.
Ravindranath et al., "Quantitation of the density of cell surface carbohydrate antigens on cancer cells with a sensitive cell-suspension ELISA," *J. Immunol. Methods*, 16(197):51-67, 1996.
Reed, "Apoptosis-targeted therapies for cancer," *Cancer Cell*, 3:17-22, 2003.
Reilly et al., "A comparison of EGF and Mab 528 labeled within for imaging human breast cancer," *J. Nucl. Med.*, 41:903-911, 2000.
Remington's Pharmaceutical Sciences, 19$^{th}$ Ed., Mach Printing Company, 1990, Smith and Rutlage, 1975.
Reutelingsperger and van Heerde, "Annexin V, the regulator of phosphatidylserine-catalyzed inflammation and coagulation during apoptosis," *Cell Mol Life Sci*, 53:527-532, 1997.
Rihova et al., "Antiproliferative effect of a lectin- and anti-thy-1.2 antibody-targeted HPMA copolymer-bound doxorubicin on primary and metastatic human colorectal carcinoma and on human colorectal carcinoma transfected with the mouse thy-1.2 gene," *Bioconjugate Chemistry*, 11(5):664-673, 2000.
Rihova, "Receptor-mediated targeted drug or toxin delivery," *Adv. Drug Deliv. Rev.*, 29:273-289, 1998.
Rogers et al., "Neomycin effects on glucose transport by rat small intestine," *Digestion*, 1:159-164, 1968.
Roohi et al., "Synthesis, quality control and biodistribution of 99mTc-Kanamycin," *Journal of Radioanalytical and Nuclear Chemistry*, 267(3):561-566, 2006.

(56) References Cited

OTHER PUBLICATIONS

Rosenberg et al., "Experience with the use of high-dose interleukin-2 in the treatment of 652 cancer patients," *Ann. Surg.*, 210(4):474-548, 1989.
Ross et al., "Differential regulation of folate receptor isoforms in normal and malignant tissue in vivo and in established cell lines," *Cancer*, 73:2432-2443, 1994.
Roth et al., "Gene therapy for cancer: what have the inventors done and where are the inventors going?" *J. Natl. Can. Inst.*, 89(1):21-39, 1997.
Rowinsky and Donehower, "Paclitaxel (taxol)," *New England Journal of Medicine*, 332:1004-1014, 1995.
Rowinsky et al., "Phase I and pharmacologic study of paclitaxel and cisplatin with granulocyte colony-stimulating factor: neuromuscular toxicity is dose-limiting," *J. Clin. Oncol.*, 11(10):2010-2020, 1993.
Rowland et al., "Suppression of tumor growth in mice by drug-antibody conjugate using a novel approach to linkage," *Nature*, 255:487-488, 1975.
Ruegg et al., "Improved in vivo stability and tumor targeting of bismuth-labeled antibody," *Cancer research*, 50:4221-4226, 1990.
Sabbantini et al., "Early findings in a phase I study of PG-Paclitaxel (CT2103 in recurrent ovarian or primary peritoneal cancer," *Proc. AACR-NCI-EORTC Int. Conference on Molecule Targets and Cancer Therapeutics*, Abs, 470:96, 2001.
Sasaki et al., "Assessment of antioxidative ability in brain: imaging of glutathione localization with technetium-99m meso-hexamethyl propyleneamine," *J. Nuclear Med.*, 35:263P, Abstract No. 1083, 1994.
Sato et al., "Simple estimation of fractional renal uptake of tc-99m mag3 using graphical analysis without syringe counting and renal depth correction," *J. Nuclear Med.*, 37:292P, Abstract No. 1303, 1996.
Schechter et al., "Assessment of epidermal growth factor receptor with 99mTc-ethylenedicysteine-C225 monoclonal antibody," *Anticancer Drugs*, 14:49-56, 2003.
Schechter et al., "Radiation dosimetry of 99mTc-labeled C225 in patients with squamous cell carcinoma of the head and neck," *J. Nucl. Med.*, 45:1683-1687, 2004.
Seabold et al., "Comparison of $^{99m}$Tc-Methoxyisobutyl Isonitrile and $^{201}$Tl Scintigraphy for Detection of Residual Thyroid Cancer After $^{131}$I Ablative Therapy," *J. Nucl. Med.*, 40(9):1434-1440, 1999.
Semenza, "Regulation of mammalian O2 homeostasis by hypoxia-inducible factor 1," *Ann. Rev. Cell Dev. Biol.*, 15:551-578, 1999.
Serruys et al., "A comparison of balloon-expandable-stent implantation with balloon angioplasty in patients with cornonary artery disease," *New England J. Medicine*, 331(8):489-495, 1994.
Seymour et al., "Synthetic polymers conjugated to monoclonal antibodies: vehicles for tumor-targeted drug delivery," *Select. Cancer Therapeut.*, 7(2):59-73, 1991.
Shankar et al., "Glucosamine infusion in rats mimics the beta-cell dysfunction of non-insulin-dependent diabetes mellitus," *Metabolism*, 47:573-577, 1998.
Sharkey et al., "Radio immunotherapy of Non-Hodgkin's lymphoma with $^{90}$Y-DOTA humanized anti-CD22 IgG ($^{90}$Y-Epratuzumab): do tumor targeting and dosimetry predict therapeutic response?" *J. Nucl. Med.*, 44:2000-2018, 2003.
Shattuck et al., "Validation of the two sample technique for measuring gfr in renal transplant patients," *J. Nuclear Med.*, 36:231P, Abstract No. 1036, 1995.
Shih et al., "Anthracycline immunoconjugates prepared by a site-specific linkage via an amino-dextran intermediate carrier," *Cancer Res.*, 54:4192-4198, 1991.
Shimada et al., "Biodistribution of liposomes containing synthetic galactose-terminated diacylglyceryl-poly(ethylen glycol)s," *Biochimica et Biophysica Acta*, 1326:329-341, 1997.
Shuke et al., "Modified renal counting method for estimation of tc-99m mag3 renal clearance," *J. Nuclear Med.*, 37:291P, Abstract No. 1301, 1996.
Silverman et al., "Evaluating tumor biology and oncological disease with positron-emission tomography," *Seminars in Radiation Oncology*, 8:183-196, 1998.
Skrzypczak-Jankun et al., "Structure of the hirugen and hirulog 1 complexes of α-thrombin," *J. Mol. Biol.*, 221:1379-1393, 1991.
Smalley et al., "Localization of fluorescent compounds in the firefly light organ," *J. Histochem. Cytochem.*, 28(4):323-329, 1980.
Smith et al., "Prognostic significance of vascular endothelial growth factor protein levels in oral and oropharyngeal squamous cell carcinoma," *J. Clin. Oncol.*, 18(10):2046-2052, 2000.
Smith et al., "Radiochemical investigations of $^{177}$Lu-DOTA-8-Aoc-BBN[7-14]NH$_2$: an in vitro/in vivo assessment of the targeting ability of this new radiopharmaceutical for PC-3 human prostate cancer cells," *Nuclear Medicine and Biol.*, 30:101-109, 2003.
Smith., "Molecular imaging with copper-64," *J. Inorg. Biochem.*, 98:1874-1901, 2004.
Song et al., "Prognostication of recovery in patients with acute ischemic stroke through the use of brain SPECT with Technetium-99m—labeled metronidazole," *Stroke*, 34:982-986, 2003.
Srivastava et al., "Comparative evaluation of chelating agents on the mobilization of cadmium: a mechanistic approach," *J. Toxicology and Environmental Health*, 47:173-182, 1996.
Stein et al., "Radioimmunotherapy of a human lung cancer xenograft with monoclonal antibody RS7: evaluation of $^{177}$Lu and comparison of its efficacy with that of $^{90}$Y and residualizing $^{131}$I," *J. Nucl. Med.*, 42:967-974, 2001.
Stoffel et al., "Evaluation of technetium-99m-L,l-ec in renal transplant recipients: a comparative study with technetium-$^{99m}$-MAG3 and iodine-125-OIH," *J. Nucl. Med.*, 35:1951-1958, 1994.
Subramanian et al., "Transchelation reactions in labeling ecd with tc-99m,", *J. Nuclear Med.*, 31:908, Abstract No. 867, 1990.
Sudimack et al., "Targeted delivery via folate receptor," *Adv. Drug Deliv. Rev.*, 41:147-162, 2000.
Sumita, "Evaluation of left ventricular function using 99mTc-diethylenetriamine-pentaacetic acid-human serum albumin (DTPA-HSA)," *Radioisotopes*, 37:502-8, 1988. (Abstract).
Sun et al., "Idium(III) and Gallium(III) Complexes of Bis(aminoethanethiol) Ligands with Different Denticities: Stabilities, Molecular Modeling, and in Vivo Behavior," *Journal of Medicinal Chemistry*, 39(2):458-470, 1996.
Surma et al., "Usefulness of Tc-99m-N,N'-ethylene-1-dicysteine complex for dynamic kidney investigations," *Nucl Med Comm*, 15:628-635, 1994.
Surwit et al., "Clinical assessment of In-CYT-103 immunoscintigraphy in ovarian cancer," *Gynecol. Oncol.*, 48:285-292, 1993.
Suzuki et al., "A modified graphic method for estimation of glomerular filtration index using dynamic renal images with tc-99m dtpa," *J. Nuclear Med.*, 36:231P, Abstract No. 1035, 1995.
Tachibana et al., "Inhibitory effects of kanamycin on glycolysis in cochlea and kidney-possible involvement in the formation of oto- and nephrotoxicities," *Biochem. Pharmacol.*, 25:2297-2301, 1976.
Taggart et al., "Novel mutations associated with carnitine palmitoyltransferase II deficiency," *Human Mutation*, 13(3):210-220, 1999.
Tait and Smith, "Site-specific mutagenesis of annexin V: role of residues from Arg-200 to Lys-207 in phospholipid binding," *Arch Biochem Biophys*, 288:141-144, 1991.
Takamizawa et al., "Differential apoptosis gene expression in pediatric tumors of the kidney," *J. Ped Surg.*, 35(2):390-395, 2000.
Takashina et al., "Comparative pharmacokinetic properties of murine monoclonal antibody A7 modified with neocarzinostatin, dextran and polyethylene glycol," *Jpn. J. Cancer Res.*, 82:1145-1150, 1991.
Tam, "Synthetic peptide vaccine design: synthesis and properties of a high-density multiple antigenic peptide system," *Proc. Natl. Acad. Sci., USA*, 85:5409-5413, 1988.
Taylor et al., "Comparison of tc-99m0(n,n1-ethylenedicysteine isomers in rats and in normal volunteers," *J. Nuclear Med.*, 37:46P-47P, Abstract No. 177, 1996.
Taylor et al., "Comparison of technetium-$^{99m}$-LL-EC isomers in rats and humans," *J. Nucl. Med.*, 38:821-826, 1997.
Thompson, "Apoptosis in the pathogenesis and treatment of disease," *Science*, 267:1456-1462, 1995.

(56) References Cited

OTHER PUBLICATIONS

Tjuvajev et al., "Comparison of radiolabeled nucleoside probes (FIAU, FHGB, and FHPG) for PET imaging of HSV1-tk gene expression," *J. Nucl. Med.*, 43:1072-1083, 2002.
Tod et al., "Clinical pharmacokinetics and pharmacodynamics of isepamicin," *Clin. Pharmacokinet.*, 38:205-223, 2000.
Tolomeo et al., "The CD95/CD95 ligand system is not the major effector in anticancer drug-mediated apoptosis," *Cell Death and Differentiation*, 5:735-742, 1998.
Tomalia et al., "Starburst dendrimers: molecular-level control of size, shape, surface chemistry, topology and flexibility from atoms to macroscopic matter," *Agnew. Chem. Int. Ed. Engl.*, 29:138-175, 1990.
Torchilin et al., "Chelating polymer modified monoclonal antibodies for radioimmunodiagnostics and radioimmunotherapy," *J. Controlled Release*, 24:111-118, 1993.
Tschopp et al., "Apoptosis: silencing the death receptors," *Curr. Biol.*, 9:R381-R384, 1999.
Tsukamoto et al., "The quantitation of absolute tc-99m-dmsa renal uptake in children from planar posterior-view method," *J. Nuclear Med.*, 37:291P, Abstract No. 1299, 1996.
Tubis and Endow, "The preparation of $^{99m}$technetium-labelled cystine, methionine and synthetic polypetide and their distribution in mice," *Int;. Journ. Appl. Rad. Isotop.*, 19:835-840, 1968.
Tuli et al., "Comparison of a simplified quantitation of tc-99m mag-3 renogram to core needle biopsy in the diagnosis of renal transplant rejection," *J. Nuclear Med.*, 37:289P, Abstract No. 1290, 1996.
Ugur et al., "Renovascular hypertension due to takayasu's arteritis demonstrated by Tc-$^{99m}$ ethylenedicysteine captopril scintigraphy," *Clinical Nuclear Medicine*, 21:714-716, 1996.
Ugur et al., "Technetium-$^{99m}$-ethylenedicysteine in the diagnosis and follow-up of renovascular hypertension," *Investigative Radiology*, 31:378-381, 1996.
Ugur et al., "Technetium-$^{99m}$-ethylenedicysteine: an alternative agent to detect renovascular hypertension," *J. of Nuclear Med.*, 38:1662-1664, 1997.
Ugur et al., "The diagnosis of renovascular hypertension with tc-99m ethylenedicysteine captopril scintigraphy," *J. Nuclear Med.*, 37:291P, Abstract No. 1302, 1996.
Ugur et al., "The diagnosis of renovascular hypertension with technetium-99m-ethylenedicysteine captopril scintigraphy," *Investigative Radiology*, 31:497-501, 1996.
Ugurel et al., "Increased serum concentration of angiogenic factors in malignant melanoma patients correlates with tumor progression and survival," *J. Clin. Oncol.*, 19(2):577-583, 2001.
Valk et al., "Hypoxia in human gliomas: Demonstration by PET with [$^{18}$F]fluoromisonidazole," *J Nucl Med*, 33:2133-2137, 1992.
Van den Eijnde et al., "In situ detection of apoptosis during embryogenesis with annexin V: from whole mount to ultrastructure," *Cytometry*, 29:313-320, 1997.
Van Heeswijk et al., "The synthesis and characterization of polypeptide-adriamycin conjugates and its complexes with adiramycin Part 1," *J. Controlled Release*, 1:301-315, 1985.
Van Nerom et al., "Comparative evaluation of Tc-99m L,L-ethylenedicysteine and Tc-99m MAG3 in volunteers," *Eur J Nucl Med*, 16:417, 1990.
Van Nerom et al., "Comparison of renal excretion ocharacteristics of isomers l,l and d,d of tc-99m ethylenedicysteine," *J. Nuclear Med.*, 31:806, Abstract No. 412, 1990.
Van Nerom et al., "Optimalization of the labelling of ethylenedicysteine (ec) with technetium-99m," *J. Labelled Compounds and Radiopharmaceuticals*, XXX:37-39, 1991.
Van Nerom et al., "First experience in healthy volunteers with Tc-99m-L,L-ethylenedicysteine, a new renal imaging agent," *Eur J Nucl Med*, 20:738-746, 1993.
Van Schepdael et al., "Capillary electrophoretic analysis of ethylene dicysteine, a precursor of the radiopharmaceutical $^{99m}$Tc ethylene dicysteine," *J. Chromatography B*, 697:251-254, 1997.
Van't Veen et al., "Lung clearance of intratracheally instilled 99mTc-tobramycin using pulmonary surfactant as vehicle," *British Journal of Pharmacology*, 126(5):1091-1096, 1999.
Vega et al., "Targeting ariamycin to EGF receptors by site-specific conjugation of monoclonal antibody to poly(L-glutamic acid)," 5th International Symposium on Polymer Therapeutics: from Laboratory to Clinical Practice, Cardiff, UK:63, 2002.
Verbeke et al., "Development of a conjugate of 99mtc-ec with aminomethylenediphosphonate in the search for a bone tracer with fast clearance from soft tissue," *Bioconjugate Chemistry*, 13(1):16-22, 2002.
Verbeke et al., "Preparation and preliminary evaluation of <99m>Tc-EC-for-MLFK," *Nuclear Medicine and Biology*, 29(5):585-592, 2002.
Verbruggen et al., "Evaluation of Tc-99m-L,L-ethylenedicysteine as a potential alternative to Tc-99m MAG3," *Eur J Nucl Med*, 16:429, 1990.
Verbruggen et al., "Is syn or anti orientation of the oxotechnetium and carboxyl group in tc-99m renal function agents affecting the renal excretion rate?" *J. Labelled Compounds and Radiopharmaceuticals*, XXX:86-88, 1991.
Verbruggen et al., "Tc-99m 1,1-ethylenedicysteine, A potential alternative to tc-99m mag3," *J. Nuclear Med.*, 31:908, Abstract No. 864, 1990.
Verbruggen et al., "Tc-99m-L,L-ethylenedicysteine: a renal imaging agent. I. Labelling and evaluation in animals," *J Nucl Med*, 33:551-557, 1992.
Villevalois-Cam et al., "Insulin-induced redistribution of the insulin-like growth factor II/mannose 6-phosphate receptor in intact rat liver," *J. Cell. Biochem.*, 77:310-322, 2000.
Vogler et al., "Pre-clinical evaluation of gadobutrol: a new, neutral, extracellular contrast agent for magnetic resonance imaging," *Eur. J. Radiol.*, 21:1-10, 1995.
Vriens et al., "The use of technetium $^{99m}$Tc annexin V for in vivo imaging of apoptosis during cardiac allograft rejection," *J. Thorac. Cardiovasc. Surg.*, 116:844-853, 1998.
Vyas et al., "Phosphatase-activated prodrugs of paclitaxel," Taxane Anticancer Agents: Basic Science and Current Status, *American Chemical Society*, Washington, DC, 124-137, 1995.
Wahl et al., "Loss of normal p53 function conferes sensation to taxol by increasing g2/m arrest and apoptosis," *Nat. Med.*, 2(1):72-79, 1996.
Wahl, "Monoclonal antibodies in nuclear medicine," *Nuclear Medicine Annual 1992*, New York, Raven Press Ltd., 91-103, 1992.
Walsh et al., "Noninvasive estimation of regional myocardial oxygen consumption by positron emission tomography with carbon-11 acetate in patients with myocardial infaction," *J. Nucl. Med.*, 30:1798-1808, 1989.
Wang et al., "[Cu(L)Mn(N$_3$)$_2$]$_n$: the first complex containing both macrocyclic oxamido and alternate (mu-1,1 and mu-1,3) azido bridges," *Inorg. Chem.*, 43:852-854, 2004.
Wang et al., "Design and synthesis of [$^{111}$In]DTPA-folate for use as a tumor-targeted radiopharmaceutical," *Bioconjugate Chem*, 8:673-679, 1997.
Wang et al., "Microtubule-interfering agents activate c-Jun N-terminal kinase/stress-activated protein kinase through both Ras and apoptosis signal-regulating kinase pathways," *J. Bio. Chem.*, 273:4928-4936, 1998.
Wang et al., "Synthesis, purification, and tumor cell uptake of Ga-67 deferoxamine-folate, a potential radiopharmaceutical for tumor imaging," *Bioconjugate Chem*, 7:56-62, 1996.
Washburn et al., "Reliable kit preparation of tc99m pentavalent dimercaptosuccinic acid [tc-99m (v) dmsa]," *J. Nuclear Med*, 35:263P, Abstract No. 1080, 1994.
Weir et al, "Prognostic value of single-photon emission tomography in acute ischaemic strike," *Eur. Journ. Nuc. Med.*, 24(1):21-26, 1989.
Weiss et al., "Hypersensitivity reaction from taxol," *J. Clin. Oncol.*, 8(7):1263-1268, 1990.
Weitman et al., "Cellular localization of the folate receptor: potential role in drug toxicity and folate homeostasis," *Cancer Res*, 52:6708-6711, 1992.

(56) References Cited

OTHER PUBLICATIONS

Weitman et al., "Distribution of the folate receptor GP38 in normal and malignant cell lines and tissues," *Cancer Research*, 52:3396-3401, 1992.

Weitman et al., "The folate receptor in central nervous system malignancies of childhood," *J Neuro-Oncology*, 21:107-112, 1994.

Wells et al., "Glycosylation of nucleocytoplasmic proteins: signal transduction and )-glcNAc," *Science*, 291:2376-2378, 2001.

Wen et al., "Conjugation with 111In-DTPA-poly(ethylene glycol) improves imaging of anti-EGF receptor antibody C225," *J Nuclear Medicine*, 42(10):1530-1537, 2001.

Wen et al., "Improved radiolabeling of PEFylated protein: PEGylated annexin V for noninvasive imaging of tumor apoptosis," *Bioconjugate Chemistry*, 2002.

Wen et al., "Poly(ethylene glucol) conjugated anti-EGF receptor antibody C225 with radiometal chelator attached to the termini of polymer chains," *Bioconjugate Chem.*, 12:545-553, 2001.

Wester et al., "Synthesis and radiopharmacology of O-(2-[18F]fluoroethyl)-L-tyrosine for tumor imaging," *J. Nucl. Med.*, 40:205-212, 1999.

Westerhof et al., "Membrane transport of natural folates and antifolate compounds in murine L1210 leukemia cells: role of carrier- and receptor-mediated transport systems," *Cancer Res.*, 51:5507-5513, 1991.

Wright et al., "Aminoglycoside antibiotics: structures, functions, and resistance," In: *Resolving the Antibiotic Paradox*, Rosen and Mobashery eds, Kluwer Academic/Plenum Pub NY, 1998.

Wu et al., "Apoptosis induced by and anti-epidermal growth factor receptor monoclonal antibody in a human colorectal carcinoma cell line and its delay by insulin," *J. Clin. Invest.*, 95:1897-1905, 1995.

Wu et al., "High-resolution microPET imaging of carcinoembryonic antigen-positive xenografts by using a copper-64-labeled engineered antibody fragment," *Proc. Nat. Acad. Sci. USA*, 97:8495-8500, 2000.

Wu et al., "Investigations of N-linked macrocycles for 111In and 90Y labeling of proteins," *Nucl. Med. & Biol.*, 19:239-244, 1992.

Wu et al., "Using Tc-99m DMSA renal cortex scan to detect renal damage in women with type 2 diabetes," *J. Diabetes Complications*, 17:297-300, 2003.

Yaghoubi et al., "Human pharacokinetic and dosimetry studies of {18F]FHBG: a reporter probe for imaging herpes simplex virus type-1 thymidine kinase reporter gene expression," *J. Nucl. Med.*, 42:1225-1234, 2001.

Yamori et al., Potent antitumor activity of MS-247, a novel DNA minor groove binder, evaluated by an in vitro and in vivo human cancer cell line panel., *Cancer Res.*, 59:4042-4049, 1999.

Yanai et al., "Amplification of the entire kanamycin biosynthetic gene cluster during empirical strain improvement of *Streptomyces kanamyceticus*," *Proc. Natl. Acad. Sci. USA*, 103:9661-9666, 2006.

Yang and Kim, "Tracer development and hybrid imaging," *Eur. J. Nucl. Med. Mol. Imaging*, 32:1001-1002, 2005.

Yang et al., "(99m)Tc-EC-guanine: synthesis, biodistribution, and tumor imaging in animals," *Pharm. Res.*, 22:1471-1479, 2005.

Yang et al., "99mtc-ec-deoxyglucose: synthesis, cellular uptake, biodistribution an dscintigraphic imaging," *J. Labelled Cpd. Radiopharm.*, 44:S513-S514, Abstract, 2001.

Yang et al., "Assessment of antiangiogenic effect using 99mTc-EC-endostatin," *Cancer Biother. Radiopharm.*, 17:233-245, 2002.

Yang et al., "Assessment of cyclooxygense-2 expression with 99mTc-labeled celebrex," *Anticancer drugs*, 15:255-263, 2004.

Yang et al., "Development of F-18-labeled fluoroerythronitroimidazole as a PET agent for imaging tumor hypoxia," *Radiology*, 194:795-800, 1995.

Yang et al., "Imaging tumor folate receptors using 99mtc-ethylenedicysteine-folate," *Proceedings of the American Association for Cancer Research*, 40:259, Abstract #1720, 1999.

Yang et al., "Imaging tumor folate receptors using radiolabeled folate and methotrexate," *J. Labelled Cpd. Radiopharm.*, 42:S696-S697, 1999.

Yang et al., "Imaging with 99mTc ECDG targeted at the multifunctional glucose transport system: feasibility study with rodents," *Radiology*, 226:465-473, 2003.

Yang et al., "In vivo and in vitro measurement of apoptosis in breast cancer cells using (99m)Tc-EC-annexin V," *Cancer Biotherapy*, 16:73-83, 2001.

Yang et al., "Metabolic pathways that mediate inhibition of hypothalamic neurons by glucose," *Diabetes*, 53:67-73, 2004.

Yang et al., "Molecular imaging using 99m-tc-ec-nitroimidazole, and 99mtc-ec-annexin v in tumor-bearing rodents," *Proceedings of the American Association for Cancer Research Annual Meeting*, 41:766, Abstract, 2000.

Yang et al., "Molecular targets for cancer imaging and therapy applications," *Ann. Nucl. Med. Sci.*, 13:19-36, 2000.

Yang et al., "Noninvasive assessment of tumor hypoxia with $^{99m}$Tc labeled metronidazole," *Pharmaceutical Research*, 16(5):743-750, 1999.

Yang et al., "Targeted molecular imaging in oncology," *Ann. Nucl. Med.*, 20:1-11, 2006.

Yasui et al., "Expression of epidermal growth factor receptor in human gastric and colonic carcinomas," *Cancer Res.*, 48:137-141, 1995.

Ye et al., TRAF family proteins interact with the common neurotrophin receptor and modulate apoptosis induction, *J. Biol. Chem.*, 274(42):30202-30208, 1999.

Yeh et al., "Fluorine-18 fluoromisonidazole tumour to muscle retention ratio for the detection of hypoxia in nasopharyngeal carcinoma," *Eur. J. Nucl. Med.*, 23(10):1378-1383, 1996.

Yen et al., "A comparative study of evaluating renal scars by 99mTc-DSMA planar and SPECT renal scans, intravenous urography, and ultrasonography," *Ann. Nucl. Med.*, 8(2):147-152, 1994.

Yen et al., "Technetium-99m-DMSA renal SPECT in diagnosing and monitoring pediatric acute pyelonephritis," *J. Nucl. Med.*, 37(8):1349-1353, 1996.

Yen et al., "The role of technetium-99m sestamibi whole-body scans in diagnosing metastatic Hurthle cell carcinoma of the thyroid gland after total thyroidectomy: a comparison with iodine-131 and thallium-201 whole-body scans," Eur. J. Nucl. Med., 21(9):980-983, 1994.

Yokoyama et al., "Polymer micelles as novel drug carrier: adriamycin-conjugated poly(ethylen glycol)-poly(aspartic acid) block copolymer," *J. Controlled Release*, 11:269-278, 1990.

Yokoyama et al., "Preparation of micelle-formin polymer-drug conjugates," *Bioconjugate Chem.*, 3:295-301, 1992.

Yoshinari et al., "Mode of action of a new indolocarbazole anticancer agent, J-107088, targeting topoisomerase I," *Cancer Res.*, 59:4271-4275, 1999.

Yoshino et al., "Differential effects of troglitazone and D-chiroinositol on glucosamine-induced insulin resistance in vivo in rats," *Metabolism.* 48:1418-23, 1999.

Young et al., "Influence of immunoglobulin heavy and light-chain expression on B-cell differentiation," *Genes Develop.*, 8:1043-1057, 1994.

Zakko et al., "Biliary excretion of Tc-$^{99m}$ ec in renal studies," *Clinical Nuclear Medicine*, 23:417-419, 1998.

Zareneyrizi et al., "Synthesis of [$^{99m}$Tc] ethylenedicysteine-colchicine for evaluation of antiangiogenic effect," *Anti-Cancer Drugs*, 7(10):685-692, 1999.

Zhang et al., "A ferromagnetically coupled $CrCu_3$ tetramer and $GdCu_4$ pentamer with a $[15]N_4$ macrocytic ligand incorporating an oxamido bridge," *Inorg. Chem.*, 42:1462-1466, 2003.

Zhao et al., "Effects of Dextranation on the pharmacokinetics of short peptides. a PET study on mEGF," *Bioconjugate Chem.*, 10:938-946, 1999.

Zhou et al., "Efficient intracellular delievery of oligonucleotides formulated in folate receptor-targeted lipid vesicles," *Bioconjugate Chem.*, 13:1220-1225, 2002.

Extended European Search Report issued in European Patent Application No. EP 10 181 884, dated Mar. 25, 2011.

Extended European Search Report issued in European Patent Application No. 06769952.0, dated Nov. 12, 2010.

Inohara et al., "Identification of human melanoma cellular and secreted ligands for galectin-3," *Biochem Biophys Res Commun*,201(3): 1366-1375, 1994.

(56) References Cited

OTHER PUBLICATIONS

Maemura et al., "Poly-N-acetyllactosaminyl O-glycans attached to leukosialin. The presence of sialyl Le(x) structures in O-glycans," *J. Biol. Chem.*, 267(34): 24379-24386, 1992.
Mathias et al., "Indium-111-DTPA folate as a potential folate-receptor-targetted radiopharmaceutical," *J. Nucle. Med.*, 39(9):1579-1585, 1998.
Office Communication issued in Australian Patent Application No. 2007308022, dated Mar. 29, 2012.
Office Communication issued in Canadian Patent Application No. 2,410,906, dated Nov. 2, 2010.
Office Communication issued in Canadian Patent Application No. 2,410,906, dated Apr. 29, 2009.
Office Communication issued in Canadian Patent Application No. 2006342202, dated Jun. 28, 2012.
Office Communication issued in Canadian Patent Application No. 2006342202, dated Feb. 7, 2012.
Office Communication issued in Chinese Patent Application No. 01811605.1, dated Mar. 12, 2004. (English translation).
Office Communication issued in Chinese Patent Application No. 01811605.1, dated Mar. 4, 2005. (English translation).
Office Communication issued in Chinese Patent Application No. 01811605.1, dated Sep. 30, 2005. (English translation).
Office Communication issued in Chinese Patent Application No. 01811605.1, dated Apr. 7, 2006. (English translation).
Office Communication issued in Chinese Patent Application No. 200780049931.X, dated Sep. 19, 2011. (English translation).
Office Communication issued in Chinese Patent Application No. 200780049931.X, dated Jul. 18, 2012. (English translation).
Office Communication issued in Chinese Patent Application No. 200680055029.3, dated Jun. 5, 2012. (English translation).
Office Communication issued in Chinese Patent Application No. 200680055029.3, dated Sep. 21, 2011. (English translation).
Office Communication issued in Chinese Patent Application No. 200680055029.3, dated Nov. 29, 2010. (English translation).
Office Communication issued in European Patent Application No. 01 941 895.3, dated Dec. 6, 2011.
Office Communication issued in European Patent Application No. 01 941 895.3, dated Feb. 28, 2011.
Office Communication issued in European Patent Application No. 01 941 895.3, dated Aug. 4, 2009.
Office Communication issued in European Patent Application No. 01 941 895.3, dated May 23, 2008.
Office Communication issued in European Patent Application No. 01 941 895.3, dated Jan. 19, 2006.
Office Communication issued in European Patent Application No. 01 941 895.3, dated Dec. 15, 2004.
Office Communication issued in European Patent Application No. 10 181 884.7, dated Dec. 6, 2011.
Office Communication issued in Japanese Patent Application No. 2001-587819, dated Aug. 3, 2011.
Office Communication issued in Japanese Patent Application No. 2004-552132, dated Sep. 9, 2009. (English translation).
Office Communication issued in Japanese Patent Application No. 2009-506472, dated Mar. 28, 2012. (English translation).
Office Communication issued in Japanese Patent Application No. 2008-123946, dated Feb. 3, 2011. (English translation).
Office Communication issued in Japanese Patent Application No. 2008-123946, dated Aug. 22, 2011. (English translation).
Office Communication issued in Japanese Patent Application No. 2008-123946, dated Mar. 12, 2012. (English translation).
Office Communication issued in Japanese Patent Application No. 2001-587819, dated Feb. 21, 2012. (English translation).
Office Communication issued in Japanese Patent Application No. 2001-587819, dated Mar. 17, 2011. (English summary).
Office Communication issued in Norwegian Patent Application No. 2002 5729, dated Nov. 14, 2008. (English translation).
Office Communication issued in Norwegian Patent Application No. 2002 5729, dated May 20, 2009. (English translation).
Office Communication issued in Norwegian Patent Application No. 2002 5729, dated Aug. 8, 2011. (English translation).
Office Communication issued in U.S. Appl. No. 12/563,724, dated Oct. 27, 2011.
Office Communication issued in U.S. Appl. No. 12/563,724, dated Feb. 23, 2012.
Office Communication issued in U.S. Appl. No. 10/732,919, dated Dec. 4, 2009.
Office Communication issued in U.S. Appl. No. 10/732,919, dated Sep. 25, 2006.
PCT International Preliminary Examination Report issued in International Application No. PCT/US01/18060, dated Oct. 11, 2002.
PCT International Preliminary Report on Patentability issued in International Application No. PCT/US2007/072669, dated Apr. 16, 2009.
PCT International Search Report issued in International Application No. PCT/US01/18060, dated Jun. 21, 2002.
Redini et al., "Cell surface glycosaminoglycans of rat rhabdomyosarcoma lines with different metastatic potentials and of non-malignant rat myoblasts," *Biochim Biophys Acta*, 883(1): 98-105, 1986.
U.S. Appl. No. 60/828,347 entitled "Efficient Synthesis of Chelators for Nuclear Imaging and Radiotherapy: Compositions and Applications" by David J. Yang and Dongfang Yu filed Oct. 5, 2006.
Office Action issued in U.S. Appl. No. 11/770,395, dated Sep. 12, 2011.
Office Action issued in U.S. Appl. No. 11/770,395, dated Jan. 3, 2012.
Office Action issued in U.S. Appl. No. 11/770,395, dated Oct. 10, 2012.
Azhdarinia, "PET and SPECT applications in medicine and pharmacology," Thesis, 2001.
Azhdarinia, "Targeted cancer diagnosis with radiolabeled endostatin," Dissertation Presented to the Faculty of the University of Texas Health Science Center at Houston, Aug. 2005.
Bryant, "Structural Characterization and Synthetic route Development for EC-DG," Project Report, Protocol No. TTP-CFM-M0002, Project Phase: SD, Cardinal Health, Nov. 1, 2006.
Codée et al., "Novel protecting groups in carbohydrate chemistry," *C.R. Chimie*, 14:178-193, 2011.
Li and Trost, "Green chemistry for chemical synthesis," *PNAS*, 105(36):13197-13202, 2008.
Liberek et al., "N-alkyl derivatives of 2-amino-2-deoxy-D-glucose," *Carbohydrate Research*, 340:1876-1884, 2005.
Litjens et al., "The use of cyclic bifunctional protecting groups in oligosaccharide synthesis—an overview," *Carbohydrate Research*, 2006.
Oscarson, "Protecting group strategies," *The Organic Chemistry of Sugars*, Chapter 3, 2005.
Pompeo and Resasco, "Water solubilization of single-walled carbon nanotubes by functionalization with glucosamine," *Nano Lett.*, 2:369-373, 2002.
Rodrigues et al., "A convenient, one-step, synthesis of β-C-glycosidic ketones in aqueous media," *Chem. Commun.*, 2049-2050, 2000.
Storr et al., "A glucosamine-dipicolylamine conjugate of $^{99m}$Tc(I) and $^{186}$Re(I) for use in imaging and therapy," *Dalton Trans.*, 654-655, 2005.
Sun et al., "Synthesis of a typical N-acetylglucosamine-containing saponin, oleanolic acid 3-yl α-L-arabinopyranosyl-(1→2)-α-L-arabino-pyranosyl-(1→6)-2-acetamido-2-deoxy-β-D-glucopyranoside," *Carbohydrate Research*, 338:827-833, 2003.
Wang et al., "Regioselective one-pot protection of carbohydrates," *Nature Letters*, 446:896-899 and Supplementary Figures, 2007.
Office Action issued in European Application No. 07 799 253.5, dated Apr. 3, 2014.
Yang et al., "Assessment of therapeutic tumor response using 99mTc-ethylenedicysteine-glucosamine," *Cancer Biotherapy & Radiopharmaceuticals*, 19(4):443-456, 2004.
Office Action issued in Japanese Application No. 2009-531499, dated Jul. 24, 2013 (English language translation thereof).
Braat, "99mTc myocardial perfusion imaging," *Curr Opin Radiol.*, 3(6):810-816, 1991. (Abstract only).

(56) References Cited

OTHER PUBLICATIONS

Khaw et al., "Imaging experimental atherosclerotic lesions in ApoE knockout mice: enhanced targeting with $Z_2D_3$-anti-DTPA bispecific antibody and $^{99m}$Tc-labeled negatively charged polymers," *The Journal of Nuclear Medicine*, 47(5):868-876, 2006.

Loubeyre et al., "Carboxymethyl-dextran-gadolinium-DTP a as a blood-pool contrast agent for magnetic resonance angiography. Experimental study in rabbits," *Invest Radiol.*, 31(5):288-293, 1996. (Abstract only).

Nedelman et al., "Rapid infarct imaging with a technetium-99m-labeled antimyosin recombinant single-chain Fv: evaluation in a canine model of acute myocardial infarction," *J Nucl Med.*, 34(2):234-241, 1993.

Nishimura et al. ,"Cardiac blood-pool scintigraphy using technetium-99m DTPA-HAS: comparison with in vivo technetium-99m RBC labeling," *J Nucl Med.*, 30:1713-1717, 1989.

Office Action issued in Canadian Application No. 2,893,683, dated May 30, 2016.

Toft et al., "Quantification of NC100668, a new tracer for imaging of venous thromboembolism, in human plasma using reversed-phase liquid chromatography coupled with electrospray ionization ion-trap mass spectrometry," *J Chroinatogr B Analyt Technol Biomed Life Sci.*, 829:91-96, 2005.

\* cited by examiner

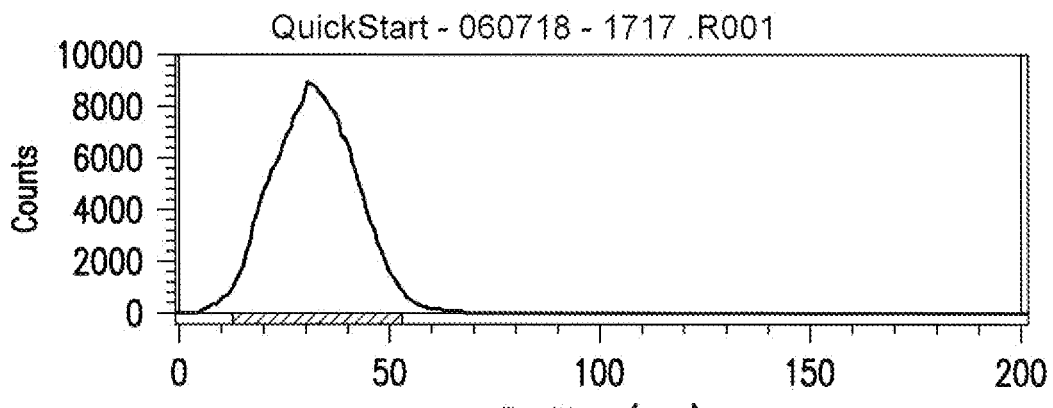
FIG.8A-(a)
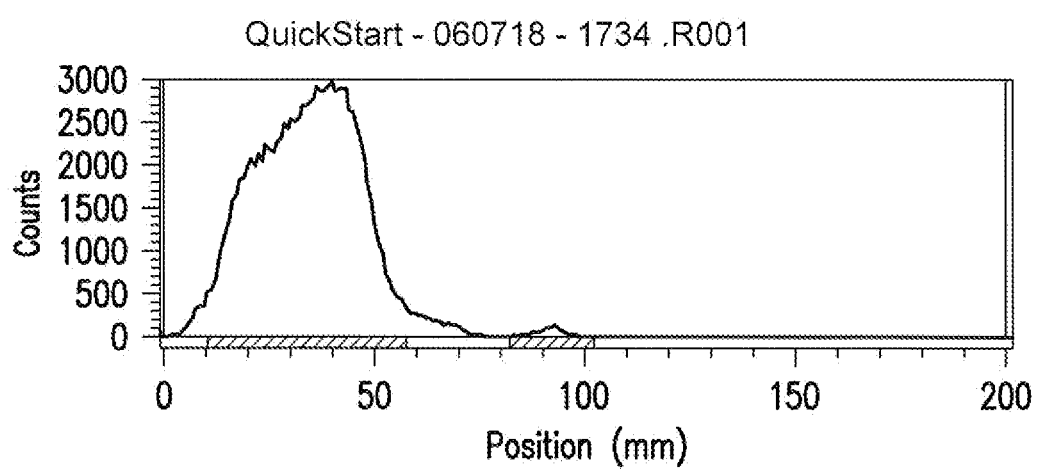
FIG.8A-(b)
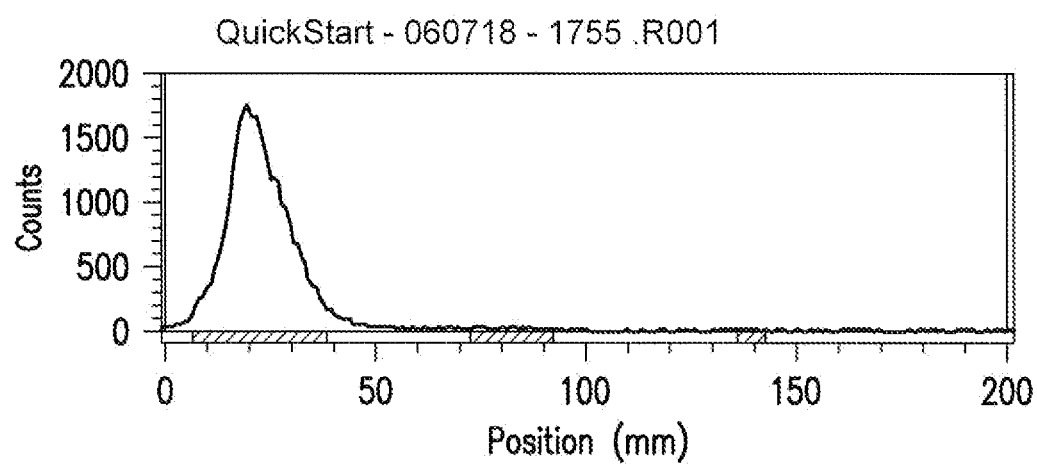
FIG.8A-(c)

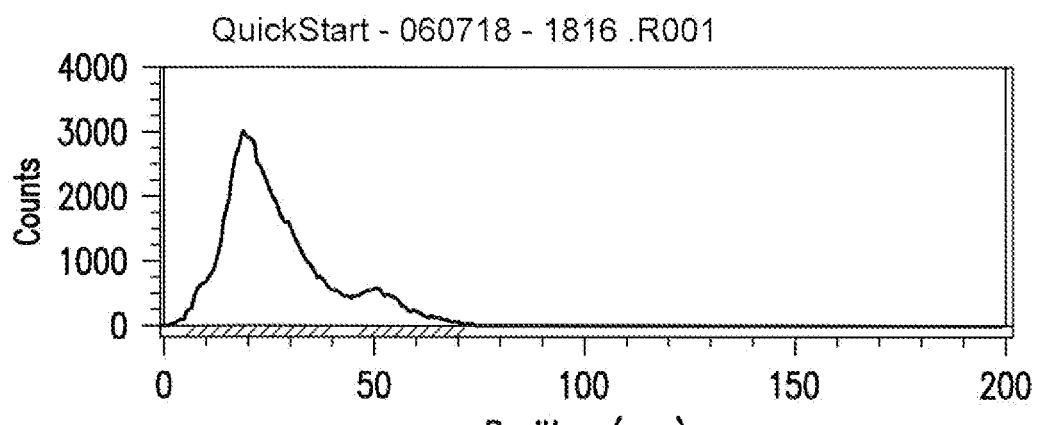
FIG.8B-(a)
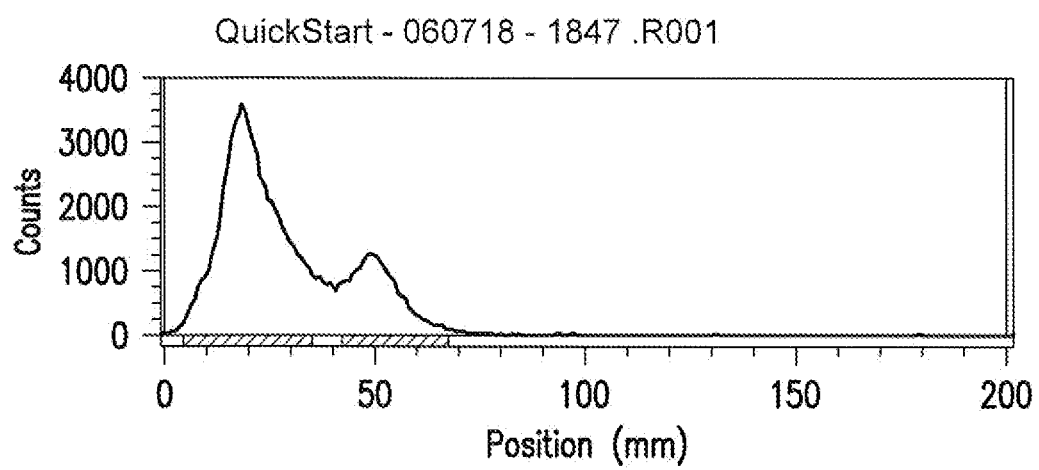
FIG.8B-(b)
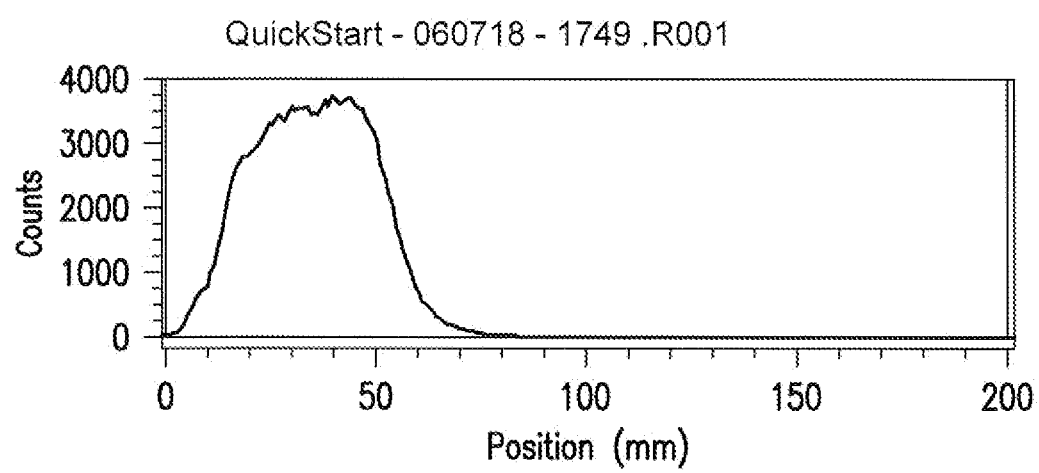
FIG.8B-(c)

EFFICIENT SYNTHESIS OF CHELATORS FOR NUCLEAR IMAGING AND RADIOTHERAPY: COMPOSITIONS AND APPLICATIONS

This application is a divisional application of co-pending U.S. patent application Ser. No. 11/770,395 filed Jun. 28, 2007, which claims the benefit of the filing date of U.S. Provisional Patent Application Ser. No. 60/828,347, filed Oct. 5, 2006, the entire contents of which are hereby incorporated by reference.

BACKGROUND OF THE INVENTION

1. Field of the Invention

The present invention relates generally to the fields of chemical synthesis, imaging, radiotherapy, labeling, chemotherapy, medical therapy, treatment of cardiovascular disease and treatment of cancer. More particularly, the invention concerns novel methods of synthesizing chelator-targeting ligand conjugates. Organic methods of synthesis are set forth herein that yield chelator-targeting ligands of high purity in comparison to chelator-targeting conjugates prepared by aqueous methods. Methods of imaging a site using these conjugates, as well as kits for preparing these conjugates, are also set forth herein. Methods of diagnosing and treating diseases (i.e., cancers, cardiovascular diseases, infections and inflammation) in a subject using compositions that includes the aforementioned conjugates are also disclosed.

2. Description of Related Art

Biomedical imaging includes various modalities that are widely used by physicians and researchers to assist with not only the diagnosis of disease in a subject, but also to gain a greater understanding of normal structure and function of the body. Exemplary imaging modalities include PET, SPECT, gamma camera imaging, CT, MRI, ultrasound, dual imaging and optical imaging.

In many instances, optimal imaging of a particular site within a subject requires the administration of a particular agent to the subject. Inorganic metals such as technetium ($^{99m}$Tc), iron, gadolinium, rhenium, manganese, cobalt, indium, platinum, copper, gallium, or rhodium have proved to be a valuable component of many imaging agents.

Labeling molecules with inorganic metals can be achieved by chelating the metal to combinations of oxygen, sulfur and nitrogen atoms, for example, of particular compounds. Chelators such as sulfur colloid, diethylenetriaminepentaacetic acid (DTPA, $O_4$), ethylenediaminetetraacetic acid (EDTA, $O_4$) and 1,4,7,10-tetraazacyclododecane-N,N',N'',N'''-tetraacetic acid (DOTA, $N_4$) have been used for this purpose. However, inorganic metals that are chelated in this manner are of limited usefulness for imaging because of their fast clearance from the body.

The preferred radioactive label for imaging agents is technetium ($^{99m}$Tc) due to its favorable half life (6 hrs), ease of production, wide availability, low energy (140 keV) and low cost. The longer half-life of isotopes such as $^{99m}$Tc facilitates shipping of the radiolabelled amino acids to hospitals without an on-site cyclotron or dedicated radiochemistry laboratory. However, attaching $^{99m}$Tc to drugs for imaging purposes is often a challenge.

$^{188}$Re has good characteristics for imaging and for potential therapeutic use because of its high B energy (2.1 MeV), short physical half-life (16.9 hr) and 155 keV gamma-ray emission for dosimetric and imaging purposes. The short physical half-life of $^{188}$Re allows for higher doses compared with long-lived radionuclides. Furthermore, the short half-life reduces the problems of radioactive waste handling and storage. In particular, $^{188}$Re is available from an in-house generator system similar to a $^{99m}$Tc generator. $^{188}$Re can be obtained from a $^{188}$W/$^{188}$Re generator, which makes it very convenient for clinical use. Both $^{99m}$Tc and $^{188}$Re emit gamma rays, so the dosimetry generated based on $^{99m}$Tc images is expected to be more accurate than that produced using the current standard radioisotope, Y-90.

Regarding imaging using positron emission tomography (PET), PET radiosynthesis must be rapid because the radio-isotope will decay during lengthy chemical synthesis and higher risk of radiation exposure may occur during radiosynthesis. Cyclotron-based tracers are constrained by the availability of a local cyclotron and its high cost. The Food and Drug Administration (FDA) permits radiopharmaceutical production in central commercial facilities under well-controlled conditions, and distributes these to local clinics where they are administered. Similarly, radionuclide generator systems that can be produced in a well-controlled facility are embraced by current FDA procedures and have a long history of successful clinical application. A generator uses a parent-daughter nuclide pair wherein a relatively long-lived parent isotope decays to a short-lived daughter isotope that is used for imaging. The parent isotope, which is produced at a cyclotron facility, can be shipped to a clinical site and from which the daughter isotope may be eluted on site for clinical use.

$^{68}$Ga has a high positron emitting quantity (89% of its total decay), therefore the main consideration with this radionuclide is its spatial resolution, which depends on the positron range (energy), the non-colinearity of annihilating photons, intrinsic properties, size and geometry of the detector and the selection of the reconstruction algorithm. Aspects of the detector design, physical properties and their influence on system spatial resolution have been extensively addressed by many authors, leading to a continuous optimization of hardware. Although the maximum positron energy of $^{68}$Ga (max=1.90 MeV, mean=0.89 MeV) is higher than that of $^{18}$F (max=0.63 MeV, mean=0.25 MeV), a study using Monte Carlo analysis on spatial resolution revealed that under the assumption of 3 mm spatial resolution of PET detectors, the conventional full width at half maximum (FWHM) of $^{18}$F and $^{68}$Ga are indistinguishable in soft tissue (3.01 mm vs. 3.09 mm). It implies that with the spatial resolution at 5 to 7 mm of current clinical scanners, the imaging quality using $^{68}$Ga-based tracers can be as good as that of $^{18}$F-based agents and this has stimulated others to investigate potential $^{68}$Ga-based imaging agents. Further, $^{68}$Ga-based PET agents possess significant commercial potential because the isotope can be produced from a $^{68}$Ge generator (275-day half-life) on site and serve as a convenient alternative to cyclotron-based PET isotopes, such as $^{18}$F or $^{13}$N.

Regarding synthetic preparations of imaging agents, when such agents are prepared in aqueous (wet) conditions, purification of the agents can sometimes present a problem. Purification in aqueous conditions can be achieved using, for example, size exclusion chromatography, or dialysis with membranes of particular molecular weight cut-offs; for example, dialysis is typically most effective when separating species of molecular weights of 1000 g/mol or higher. However, this method of purification often isolates not only the desired agent, but also any other species that may pass through the membrane. Introduction of impurities into imaging agents may be problematic in future applications of the imaging agents, especially regarding imaging and/or therapeutic uses. For example, if an imaging agent incorporating a radionuclide (the "true" imaging agent) is thought to be pure but actually contains impurities that also incorporate a radionuclide, the proper measurement or detection of the "true" imaging agent may be obscured or rendered false due to the presence of the impurities.

Methods of synthesizing organic compounds in organic media, which employ organic solvents and the use of protecting groups, typically offer improvements in the purification of compounds over aqueous purifications. The installation of protecting groups permits various functional groups of intermediates during the synthesis to be protected, and facilitates the purification of those intermediates. Various means of purification using organic solvents allow for separation and isolation of desired compounds, such as imaging agents, with very little impurities. Further, species of molecular weights under 1000 g/mol can often easily be purified using organic chemistry purification methods. In view of the benefits offered by organic synthesis and purification over aqueous purification, methods of organically synthesizing and purifying imaging agents would likely yield agents of higher purity than those obtained via aqueous purification.

To date, certain imaging agents have been prepared only via aqueous means. The impurities present in these agents can detract from their use as imaging and/or therapeutic agents. Thus, a need exists for the preparation of these and other agents using synthetic organic techniques to allow for agents of higher purities to be obtained.

SUMMARY OF THE INVENTION

The present inventors have identified novel methods of synthesizing agents that are, in certain embodiments, conjugates of a chelator and a targeting ligand (also called a targeting moiety). Such agents may be used for imaging, diagnostic, and/or therapeutic purposes, for example. Both organic (solvent) and wet (aqueous) synthetic and purification methods are described, and it is shown that organic synthetic and purification methods result in compounds of higher purity than those prepared/purified by wet chemistry. Compounds of high purity are better candidates for clinical application, for example. Furthermore, certain compounds and methods of the present invention offer wide flexibility and selectivity in terms of (1) available sites of conjugation of a chelator to a targeting ligand and (2) atoms available for chelation to a metal ion.

Accordingly, one general aspect of the present invention contemplates a method of synthesizing a chelator-targeting ligand conjugate comprising:

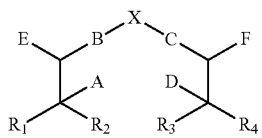

to at least one targeting ligand comprising at least one functional group, wherein:
A, D, E and F are each independently H, lower alkyl, —COOH, protected carboxylic acid, —NH$_2$, protected amine, thiol, or protected thiol, wherein at least one position is —NH$_2$ or thiol;

B and C are each independently a secondary amine, a tertiary amine, —S—, —S(O)—, or —S(O)$_2$—;
R$_1$, R$_2$, R$_3$ and R$_4$ are each independently H or lower alkyl;
X is selected from the group consisting of —CH$_2$—CH$_2$—, —CH$_2$—CH$_2$—CH$_2$—, —CH$_2$—C(O)—, —C(O)—CH$_2$—, —C(O)—CH$_2$—CH$_2$— and —CH$_2$—CH$_2$—C(O)—; and
the conjugation is between A, D, E or F of the chelator and at least one unprotected functional group of each targeting ligand;
wherein at least one of A, D, E, F, or the targeting ligand comprises a protected functional group, provided that at least one functional group of the targeting ligand is unprotected, and
provided that when A and D are each —NH$_2$, neither B nor C is a secondary or a tertiary amine. Conjugates of the present invention may include one targeting ligand, or more than one targeting ligand. In some embodiments, the conjugate includes two targeting ligands. The targeting ligands may be identical, or may be of distinct types. Types of targeting ligands are discussed in greater detail below.

Methods discussed herein are distinct from methods described in copending U.S. application Ser. No. 11/737, 694, filed Apr. 19, 2007, and are distinct from methods described in copending International Application No. PCT/US2006/016784, filed May 4, 2006.

The chelator pictured above may also be visualized as the following:

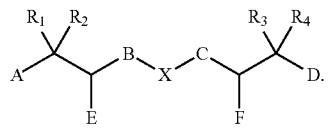

In general, methods of the present invention take place in an organic medium. As used herein, "organic medium" refers to solutions and purification methods comprising one or more organic solvents. Solvent choices for the methods of the present invention will be known to one of ordinary skill in the art. Solvent choices may depend, for example, on which one(s) will facilitate the solubilizing of all the reagents, or, for example, which one(s) will best facilitate the desired reaction (particularly if the mechanism of the reaction is known). Solvents may include, for example, polar solvents and/or non-polar solvents. A solvent may be a polar aprotic solvent, such as dimethylsulfoxide. Solvents choices include, but are not limited to, dimethylformamide, dimethylsulfoxide, dioxane, methanol, ethanol, hexane, methylene chloride, tetrahydrofuran, and/or acetonitrile. In some embodiments, solvents include ethanol, dimethylformamide and/or dioxane. More than one solvent may be chosen for any particular reaction or purification procedure. Water may also be admixed into any solvent choice; this can be done to enhance the solubility of one or more reactants, for example.

In some embodiments, only the conjugation between a chelator and a targeting ligand takes place via organic synthesis (that is, in organic media). In some embodiments, only the synthesis of a chelator takes place via organic synthesis. In some embodiments, only the chelation of a valent metal ion takes place via organic synthesis. In certain embodiments, any one or more of these steps take place via organic synthesis.

Any chelator (that is, a compound that is capable of chelating, or binding, one or more metal ions) known to those of skill in the art may be utilized using the methodology of the present invention, and exemplary chelators are described in further detail herein. Chelators typically bind to one or more metal ions via an ionic bond. In some embodiments, the chelator comprises DTPA (diethylenetriaminepentaacetic acid), one or more amino acids, or any combination of one or more of these groups. In certain embodiments, one or more amino acids are selected from the group consisting of glycine and cysteine. In some embodiments, the chelator is selected from the group consisting of dicysteine, triglycine cysteine and tricysteine glycine. The number and choices of amino acids may be limited by their solubility in organic media. In certain embodiments, the chelator is ethylenedicysteine (EC).

Targeting ligands are also described in further detail herein. While a chelator may be conjugated (that is, chemically attached or bound) to a targeting ligand via any mode known to those of skill in the art (e.g., a covalent bond, an ionic bond, a dative bond, an ion pair), typically the attachment comprises a covalent bond.

Methods of the present invention may further comprise at least one purification step. Any compound of the present invention may be purified via any method known to those of skill in the art. Persons of skill in the art are familiar with such methods, and when those methods may be employed. For example, in a multi-step synthesis that is aimed at arriving at a particular compound, a purification step may be performed after every synthetic step, after every few steps, at various points during the synthesis, and/or at the very end of the synthesis. In some methods, one or more purification steps comprises technique selected from the group consisting of silica gel column chromatography, HPLC (high-performance liquid chromatography) and LC (liquid chromatography). In certain embodiments, purification methods specifically exclude size exclusion chromatography and/or dialysis. Methods of purification are described in more detail below.

In certain embodiments, unconjugated chelators and/or chelator-targeting ligand conjugates are generated via synthetic organic methods in very high purity relative to such compounds generated via aqueous methodology. For example, in some embodiments of the present invention, an unconjugated chelator, an unprotected chelator, a protected chelator, a chelator-targeting ligand conjugate, or a metal ion-labeled chelator-targeting ligand conjugate generated via organic means (or any compound comprising a combination of chelator, protecting group, targeting ligand and metal ion) is between about 90% and about 99.9% pure, compared to between about 50% and about 70% pure for the aqueous product. In certain embodiments, an unconjugated chelator, an unprotected chelator, a protected chelator, a chelator-targeting ligand conjugate, or a metal ion-labeled chelator-targeting ligand conjugate generated via organic means (or any compound comprising a combination of chelator, protecting group, targeting ligand and metal ion) is about or at least about 60%, 61%, 62%, 63%, 64%, 65%, 66%, 67%, 68%, 69%, 70%, 71%, 72%, 73%, 74%, 75%, 76, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% pure, or higher, or any range derivable therein. In certain embodiments, the range is about 70% to about 99.9%. In certain embodiments, the range is about 75% to about 99.9%. In certain embodiments, the range is about 80% to about 99.9%. In certain embodiments, the range is about 85% to about 99.9%. In certain embodiments, the range is about 90% to about 99.9%. In certain embodiments, the range is about 95% to about 99.9%.

In certain embodiments of the present invention, at least one of A, D, E, or F is protected in at least one step using at least one protecting agent, and at least one functional group of the targeting ligand is protected in at least one step using at least one protecting agent. Functional groups, as described herein, may be those of any type known to one of skill in the art. The term "functional group" generally refers to how persons of skill in the art classify chemically reactive groups. Non-limiting examples include alkene, alkyne, aryl (e.g., phenyl, pyridinyl), alcohol, aldehyde, ketone, azide, halogen, ester, —COOH, —NH$_2$, thiol, a secondary amine, a tertiary amine, —S—, —S(O)— and —S(O)$_2$—. In some embodiments, at least one functional group comprises an atom selected from the group consisting of C, H, O, N, P and S. Positions A, B, C, D, E and/or F may comprise one or more functional groups (e.g., —COOH, —NH$_2$, thiol, a secondary amine, a tertiary amine, —S—, —S(O)—, or —S(O)$_2$—). In certain embodiments, at least one functional group of the targeting ligand comprises an atom selected from the group consisting of O, N, S and P. The functional group of the targeting ligand may be, for example, selected from the group consisting of amino, amido, thiol, hydroxyl, ether, ester, carbonyl, carboxylic acid, sulfonamido, thioether, thioester and thiocarbonyl.

Both the targeting ligand and the chelator will typically have one or more functional groups. Functional groups and protecting agents that may be used to generate a protected functional group are described herein. Persons of skill in the art will understand that any functional group may be protected using a protecting agent as necessary, as described herein. As such, a functional group may be protected (e.g., a protected amine, such as —NH-Cbz) or unprotected—also called, "free" (such as —NH$_2$). As is known to those of skill in the art, protecting groups are utilized in organic syntheses and not aqueous syntheses.

Further, in certain embodiments, one or more protecting groups may be removed. The removal of a protecting group can be done at any time during any method or synthesis described herein, but is typically performed when the protecting group is no longer needed and the functional group that is being protected is desired to be "revealed." In any method described herein, any compound comprising a chelator described herein (e.g., a chelator-targeting ligand conjugate, a metal ion labeled-chelator-targeting ligand conjugate) may not contain any protecting groups, or may comprise one or more protecting groups. For example, a site may be imaged using a metal ion labeled-chelator-targeting ligand conjugate that contains no protecting groups, or contains one or more protecting groups.

In certain embodiments, the targeting ligand comprises a leaving group. The term "leaving group" generally refers to groups readily displaceable by a nucleophile, such as an amine, an alcohol or a thiol nucleophile. Such leaving groups are well known and include, for example, carboxylates, N-hydroxysuccinimide, N-hydroxybenzotriazole, halides, triflates, tosylates, mesylates, alkoxys, thioalkoxys, sulfonyls and the like.

In further embodiments, the three or more functional groups of the chelator together form a chelate. Typically, three or four atoms together form a chelate. In certain embodiments, the chelate is selected from the group consisting of NS$_2$, N$_2$S, S$_4$, N$_2$S$_2$, N$_3$S and NS$_3$. For example, three thioethers and one secondary amine may form an NS$_3$ chelate. In some embodiments, such as with ethylenedicysteine, the chelate is an $N_2S_2$ chelate. Chelates may be that of any type known to those of skill in the art, and are further described herein. Other atoms besides N and S may comprise a chelate, such as oxygen.

As used herein, "chelate" may be used as a noun or a verb. As a noun, "chelate" refers to one or more atoms that are either capable of chelating one or more metal ions, or are chelating to one or more metal ions. Metal ions are described in more detail herein. In some embodiments, only one metal ion coordinates to a chelate. A non-limiting example of "chelate" includes "an $N_2S_2$" chelate: this means that two nitrogen atoms and two sulfur atoms of a chelator are either a) capable of chelating to one or more metal ions or b) are coordinated to (or chelated to) to one or more metal ions. Accordingly, in some embodiments, the chelate is $N_2S_2$. A compound comprising a chelate is a chelator. Typically, just one metal ion is chelated to a chelator.

In certain embodiments, at least one of A, D, E and F is a thiol. The thiol may be protected in at least one step using at least one thiol protecting agent. The thiol protecting agent may be any of those known to those of skill in the art. For example, the thiol protecting agent may be selected from a group consisting of an alkyl halide, a benzyl halide, a benzoyl halide, a sulfonyl halide, a triphenylmethyl halide, a methoxytriphenylmethyl halide and cysteine.

In certain embodiments, at least one of A, D, E and F comprises a primary amine or at least one of B and C comprises a secondary amine. In certain embodiments, at least one amine may be protected in one or more steps using at least one amine protecting agent. Amine protecting agents may be any of those known to those of skill in the art. For example, the amine protecting group may be selected from the group consisting of benzylchloroformate, p-nitro-chlorobenzylformate, ethylchloroformate, di-tert-butyl-dicarbonate, triphenylmethyl chloride and methoxytriphenylmethyl chloride.

In certain embodiments, the chelator is ethylenedicysteine. When employing ethylenedicysteine as a chelator in the synthesis of an ethylenedicysteine-targeting ligand conjugate, the two thiol groups of ethylenedicysteine are protected using at least one thiol protecting agent (e.g., using two or more equivalents of a thiol protecting agent) and in another step the two amine groups of ethylenedicysteine are protected using at least one amine protecting agent (e.g., using two or more equivalents of an amine protecting agent). Since thiol groups are more reactive than amine groups, thiol groups will typically be protected before amine groups are protected when both are initially unprotected ("free").

As mentioned, conjugation between the chelator and a targeting ligand may take place via any method and chemical linkage known to those of skill in the art. That is, the targeting ligand may be conjugated or bound to one or more chelators in any manner known to those of ordinary skill in the art. In certain embodiments, conjugation between the chelator and the targeting ligand takes place in a single step (i.e., a "one-pot" reaction). As is known by those of skill in the art, such one-step reactions are desirable as they save time, help minimize waste reagents and minimize loss of product. Any of A, B, C, D, E, and/or F may participate in conjugation to a targeting ligand. In addition, any of A, B, C, D, E, and/or F may participate in chelation. Further, any of A, B, C, D, E, and/or F may participate in both chelation and conjugation. Such flexibility allows chelators of the present invention to be manipulated in a variety of ways, depending on, for example, the reactivity of a chosen targeting ligand, the selectivity of conjugation desired, the solubility of the reagents, the metal ion desired for chelation, etc. Typically, but not always, conjugation occurs prior to chelation.

Typically, one type of targeting ligand is conjugated to one chelator, but multiple targeting ligands may be conjugated to a single chelator. Commonly, during the organic synthesis of chelator-targeting ligand conjugates, as between the chelator and the targeting ligand, one acts as the nucleophile and one acts as the electrophile such that conjugation takes place via a covalent bond. The covalent bond may be of any type known to those of skill in the art. In some embodiments, the covalent bond is selected from the group consisting of an amide bond, an ether bond, an ester bond, a thioether bond, a thioester bond, a sulfonamido bond and a carbon-carbon bond. The carbon-carbon bond is typically a single bond, but can also be a double or a triple bond. When acting as electrophiles, chelators and targeting ligands may comprise functional groups such as halogens and sulfonyls, which act as leaving groups during conjugation. In some embodiments, the conjugation takes place at one or more functional groups of the chelator selected from the group consisting of carboxylic acid, amine and thiol. Targeting ligands may also comprise nucleophilic groups, such as —$NH_2$, which may participate in conjugation with an electrophilic chelator. Modes of conjugation are discussed in greater detail below.

In certain embodiments, the chelator-targeting ligand conjugate further comprises a linker between the chelator and the targeting ligand. Such a linker may, for example, provide for easier conjugation between the chelator and the targeting ligand by providing a reactive group that facilitates the conjugation reaction. The linker may be of any type known to those of skill in the art. The linker may be initially attached to the chelator or to the targeting ligand. A linker may be attached to the chelator, while another linker is attached to the targeting ligand, such that the two linkers may then be joined. Persons of skill in the art will be familiar with the types of linkers available for methods of the present invention. In some embodiments, the linker is selected from the group consisting of a peptide, glutamic acid, aspartic acid, bromo ethylacetate, ethylene diamine, lysine and any combination of one or more of these groups.

In certain embodiments, E and F are each independently selected from the group consisting of —COOH, —$NH_2$, or thiol. In some embodiments, E and F are each —COOH. In certain embodiments, the conjugation of at least one targeting ligand takes place at E and/or F. In certain embodiments, each of A and D are each protected by at least one protecting group prior to conjugation.

As one of skill in the art would appreciate, in order to conjugate a chelator to a targeting ligand, at least one functional group of the chelator and at least one functional group of the targeting ligand must be "free" (that is, unprotected by a protecting group) such that the two compounds may be joined together.

The chelator may further comprise a spacer, X. In certain aspects, use of a spacer allows for the proper number and orientation of chelating atoms to chelate a metal ion. Persons of skill in the art will be familiar with the types of spacers that may be used for methods of the present invention, and examples of spacers are disclosed below. For example, an alkyl spacer, such as (—$CH_2$—)$_n$, wherein n is 1-100, may be employed. One type of chelator employable in methods of the present invention that comprises an ethylene spacer is ethylenedicysteine (EC). In certain embodiments, X is —$CH_2$—C(O)—, —C(O)—$CH_2$—, —$CH_2$—$CH_2$—C(O)—, or —C(O)—$CH_2$—$CH_2$— and B and/or C is a secondary amine. This embodiment typically results in either B or C being less nucleophilic than the other. For example, if together B, C and L are depicted as —NH—C(O)—CH$_2$—CH$_2$—NH—, the secondary amine of position C will be more nucleophilic than the secondary amine of B. Thus, C will be more reactive, resulting in selective conjugation of a targeting ligand at position C. In certain embodiments, both positions A and D or E and F are each protected by at least one protecting group prior to conjugation at C.

One feature of using amide bonds, such as when B, C, and L together form —NH—C(O)—CH$_2$—CH$_2$—NH—, lies in the fact that reactions wherein a metal ion is chelated to a chelator often take place in acidic media. Amide bonds are relatively resistant to degradation in acidic media, and therefore provide structural stability in the chelator during such chelation reactions. Thus, X together with B and/or C may comprise an amide bond.

Chelator-targeting ligand conjugates chelated to a metal ion may function as, for example, imaging and/or diagnostic agents, as described herein. They can also function as therapeutic agents, or agents for dual diagnosis and therapy, or dual imaging and therapy. Accordingly, in certain embodiments, methods of the present invention further comprise chelation of a metal ion to a chelator to generate a metal ion labeled-chelator-targeting ligand conjugate. The metal ion may be any of those known to one of ordinary skill in the art. The metal ion may be a "cold" (non-radioactive) metal ion, or a radionuclide. In non-limiting examples, the metal ion may be selected from the group consisting of a technetium ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion and a rhodium ion. The cold metal ion may be, for example, selected from the group consisting of Cu-62, As-72, Re-187, Gd-157, Bi-213, Fe-56, Mn-55, an iron ion, a manganese ion, a cobalt ion, a platinum ion and a rhodium ion.

The metal ion may be a radionuclide, and may be any radionuclide known to those of skill in the art. The radionuclide, in some embodiments, may be selected from the group consisting of $^{99m}$Tc, $^{188}$Re, $^{186}$Re, $^{153}$Sm, $^{166}$Ho, $^{90}$Y, $^{89}$Sr, $^{67}$Ga, $^{68}$Ga, $^{111}$In, $^{148}$Gd, $^{55}$Fe, $^{225}$Ac, $^{212}$Bi, $^{211}$At, $^{45}$Ti, $^{60}$Cu, $^{61}$Cu, $^{67}$Cu, and $^{64}$Cu. In some embodiments, the metal ion is $^{99m}$Tc.

If the metal ion is chosen to be $^{99m}$Tc, for example, the method may further comprise the addition of a reducing agent. The reducing agent may be that of any known to those of skill in the art. In some embodiments, the reducing agent comprises an ion selected from the group consisting of a dithionite ion, a stannous ion and a ferrous ion. In some embodiments, the metal ion is $^{188}$Re. In other embodiments, the metal ion is $^{68}$Ga.

When a metal ion is employed in the method of the present invention, the metal ion may be chelated to any chelate known to those of skill in the art, as described herein. Persons of skill in the art recognize that metal ions chelate to varying numbers of atoms depending on, for example, the type of metal, its valency and the atoms available for chelation. For example, three or four atoms of the chelator may chelate to one metal ion. In certain embodiments, a chelated metal ion may be $^{99m}$Tc. In certain embodiments, a chelated metal ion may be $^{186}$Re. In certain embodiments, a chelated metal ion may be $^{187}$Re.

In some embodiments, the chelate may be selected from the group consisting of NS$_2$, N$_2$S, S$_4$, N$_2$S$_2$, N$_3$S and NS$_3$. In certain embodiments, any one or more of these chelates may not be a chelate of the present invention. In some embodiments, N$_3$S is not a chelate. In certain embodiments, the chelate is N$_2$S$_2$, for example, ethylenedicysteine. Methods of the present invention may further comprise the synthesis of a metal ion labeled-chelator-targeting ligand conjugate wherein the targeting ligand participates with A, B, C, D, E, and/or F in chelation to a metal ion. Metal ions, chelation and targeting ligands are discussed in more detail below. In some embodiments, the metal ion can be imaged. The imaging can be by any method known to those of ordinary skill in the art. Exemplary methods of imaging are discussed at length in the specification below, and include PET and SPECT.

As discussed above, metal ion labeled-chelator-targeting ligand conjugates prepared via organic synthesis typically enjoy purities higher than those achieved via aqueous preparations. For example, in some embodiments of the present invention, the metal ion labeled-chelator-targeting ligand conjugate generated via organic means is between about 90% and about 99.9% pure, compared to between about 50% and about 70% pure for the aqueous product. In certain embodiments, the metal ion labeled-chelator-targeting ligand conjugate synthesized via organic means is about or at least about 60%, 61%, 62%, 63%, 64%, 65%, 66%, 67%, 68%, 69%, 70%, 71%, 72%, 73%, 74%, 75%, 76, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% pure, or higher, or any range derivable therein.

Any chelator described herein may be chelated to a metal ion. A protected chelator may be used, or an unprotected chelator. The chelator may be chelated before or after the chelator is purified.

In certain embodiments, generation of a metal ion labeled-chelator-targeting ligand conjugate comprises:
(a) removing at least one protecting group from a chelator-targeting ligand conjugate as described herein; and
(b) chelating a metal ion to the chelator of the chelator-targeting ligand conjugate.

In certain embodiments, generation of a metal ion labeled-chelator-targeting ligand conjugate comprises:
(a) obtaining a chelator of the following formula:

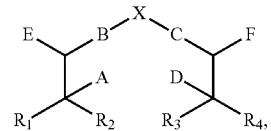

wherein A, B, C, D, E, F, X, R$_1$, R$_2$, R$_3$ and R$_4$ are as defined above and at least one of A, B, C, D, E, F, X, R$_1$, R$_2$, R$_3$ and R$_4$ is protected by at least one protecting agent;
(b) conjugating the chelator to a targeting ligand to generate a chelator-targeting ligand conjugate;
(c) removing at least one protecting group from the chelator-targeting ligand conjugate; and
(d) chelating a metal ion as described herein to the chelator of the chelator-targeting ligand conjugate.

Indeed, it is contemplated that any compound described herein comprising one or more protecting groups may, in any particular method, undergo removal of one or more protecting groups. A protecting group may be removed, for example, from the chelator moiety, the targeting ligand moiety, or both moieties in one or more steps before or after a chelator-targeting ligand conjugate is chelated to a metal ion, as described herein. Protecting groups are described in more detail herein, including their installation and removal.

In other embodiments, generation of a metal ion labeled-chelator-targeting ligand conjugate comprises:
(a) chelating a metal ion to a chelator as described herein to generate a metal ion labeled-chelator;
(b) conjugating the metal ion labeled-chelator to a targeting ligand; and
(c) removing one or more protecting groups from the metal ion labeled-chelator-targeting ligand conjugate.

Certain embodiments of the present invention contemplate a method of synthesizing a protected chelator comprising:
(a) obtaining a chelator of the following formula:

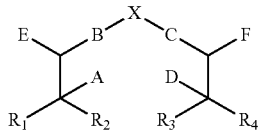

wherein:
A, D, E and F are each independently H, lower alkyl, —COOH, —NH$_2$, or thiol, wherein at least one position is —COOH, —NH$_2$, or thiol;
B and C are each independently a secondary amine, a tertiary amine, —S—, —S(O)—, or —S(O)$_2$—;
R$_1$, R$_2$, R$_3$ and R$_4$ are each independently H or lower alkyl; and
X is selected from the group consisting of —CH$_2$—CH$_2$—, —CH$_2$—CH$_2$—CH$_2$—, —CH$_2$—C(O)—, —C(O)—CH$_2$—, —C(O)—CH$_2$—CH$_2$— and —CH$_2$—CH$_2$—C(O)—; and
(b) protecting the —COOH, —NH$_2$, or thiol using a carboxylic acid protecting agent, an amine protecting agent, or a thiol protecting agent, respectively.

As for any synthetic method of the present invention, the method may be carried out in an organic medium. The protected chelator may be protected ethylenedicysteine. The method may further comprise a purification step, a chelation step comprising chelation of a metal ion, the removal of at least one protecting group, or any combination of these steps. (Indeed, any method described herein may comprise a purification step, a chelation step comprising chelation of a metal ion, the removal of at least one protecting group, or any combination of these steps.) In this or any method described herein, the protected chelator may be about 80% to about 99.9% pure. For example, the protected chelator may be about 80% to about 90% pure. In this or any method described herein comprising a chelator with the core structure shown above, when A and D are each —NH$_2$, neither B nor C may be a secondary or a tertiary amine.

Certain embodiments of the present invention also contemplate a chelator-targeting ligand conjugate of the following formula:

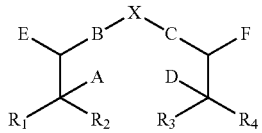

wherein:
A, D, E and F each independently comprise H, lower alkyl, —COOH, a protected carboxylic acid, —NH$_2$, a protected amine, thiol, a protected thiol, an unprotected targeting ligand, or a protected targeting ligand,
wherein at least one of A, D, E and F comprises a protected carboxylic acid, a protected amine, or a protected thiol and at least one of A, D, E and F comprises a protected targeting ligand or an unprotected targeting ligand;
B and C are each independently a secondary amine, a tertiary amine, —S—, —S(O)—, or —S(O)$_2$—;
R$_1$, R$_2$, R$_3$ and R$_4$ are each independently H or lower alkyl;
X is selected from the group consisting of —CH$_2$—CH$_2$—, —CH$_2$—CH$_2$—CH$_2$—, —CH$_2$—C(O)—, —C(O)—CH$_2$—, —C(O)—CH$_2$—CH$_2$— and —CH$_2$—CH$_2$—C(O)—; and
wherein the chelator-targeting ligand conjugate is between about 70% and about 99.9% pure.

The conjugate may be between about 80% and about 99.9% pure. The conjugate may be between about 90% and about 99.9% pure. The conjugate may be further defined as a metal ion labeled-chelator-targeting ligand conjugate. The conjugate may be further defined as $^{99m}$Tc-EC-glucosamine, $^{186}$Re-EC-glucosamine, or $^{187}$Re-EC-glucosamine.

As mentioned, the targeting ligand may be of any type known to those of skill in the art, and such ligands are discussed in more detail herein. A "targeting ligand" is defined herein to be a molecule or part of a molecule that binds with specificity to another molecule. One of ordinary skill in the art would be familiar with the numerous agents that can be employed as targeting ligands in the context of the present invention. The targeting ligand can be any such molecule known to those of ordinary skill in the art. Non-limiting examples of targeting ligands include a tissue-specific ligand, an antimicrobial, an antifungal, or an imaging agent.

In some embodiments, the targeting ligand is a "tissue-specific ligand." A "tissue-specific ligand" is defined herein to refer to a molecule or a part of a molecule that can bind or attach to one or more tissues. The binding may be by any mechanism of binding known to those of ordinary skill in the art.

Non-limiting examples of tissue-specific ligands include a drug, a DNA topoisomerase inhibitor, a DNA intercalator, an antimetabolite, a disease cell cycle targeting compound, a gene expression marker, an angiogenesis targeting ligand, a tumor marker, a folate receptor targeting ligand, an apoptotic cell targeting ligand, a hypoxia targeting ligand, a disease receptor targeting ligand, a receptor marker, a peptide, a nucleotide, an antibody, an antisense molecule, a siRNA, glutamate pentepeptide, an agent that mimics glucose, amifostine, angiostatin, monoclonal antibody C225, monoclonal antibody CD31, monoclonal antibody CD40, capecitabine, deoxycytidine, fullerene, herceptin, human serum albumin, lactose, quinazoline, thalidomide, transferrin, and trimethyl lysine.

In some embodiments, the tissue-specific ligand may be a drug, such as an anticancer agent. Non-limiting examples of anti-cancer agents include tamoxifen, topotecan, LHRH, podophyllotoxin, colchicine, endostatin, tomudex, thiotepa, cyclosphosphamide, busulfan, improsulfan, piposulfan, benzodopa, carboquone, meturedopa, uredopa, altretamine, triethylenemelamine, trietylenephosphoramide, triethiylenethiophosphoramide, trimethylolomelamine, bullatacin, bullatacinone, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, a sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, and ranimnustine, calicheamicin, dynemicin, clodronate, an esperamicin, neocarzinostatin chromophore, an aclacinomysin, actinomycin, authrarnycin, azaserine, a bleomycin, cactinomycin, carabicin, caminomycin, carzinophilin, a chromomycini, dactinomycin, daunorubicin, detorubicin, 6-diazo-5-oxo-L-norleucine, epirubicin, esorubicin, idarubicin, marcellomycin, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin, 5-fluorouracil (5-FU), denopterin, methotrexate, pteropterin, trimetrexate, 6-mercaptopurine, thiamiprine, thioguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, a maytansinoid, mitoguazone, mopidanmol, nitraerine, pentostatin; phenamet; pirarubicin; losoxantrone; podophyllinic acid; 2-ethylhydrazide; procarbazine, PSK polysaccharide complex, razoxane, rhizoxin, sizofuran, spirogermanium, tenuazonic acid, triaziquone, 2,2',2"-trichlorotriethylamine, a trichothecene, urethan, vindesine, dacarbazine, mannomustine, mitobronitol, mitolactol, pipobroman, gacytosine, arabinoside ("Ara-C"), cyclophosphamide, thiotepa, doxetaxel, chlorambucil, 6-thioguanine, mercaptopurine, methotrexate, cisplatin, oxaliplatin, carboplatin, vinblastine, platinum, ifosfamide, mitoxantrone, vincristine, vinorelbine, novantrone, teniposide, edatrexate, daunomycin, aminopterin, xeloda, ibandronate, irinotecan, RFS 2000, difluoromethylornithine (DMFO), retinoic acid, and capecitabine.

Other examples of drugs include cardiovascular drugs. Non-limiting examples of such drugs include an antihyperlipoproteinemic agent, an antiarteriosclerotic agent, an antithrombotic agent, a fibrinolytic agent, an antiplatelet agent, a blood coagulant, a thrombolytic agent, an antiarrythmic agent, an antihypertensive agent, a vasopressor, an antiangiotension II agent, an afterload-preload reduction agent, a diuretic, and an inotropic agent. Examples of cardiovascular drugs include mexiletine, tocamide, moricizine, procainamide, disopyramide, quinidine, popafenone, flecamide, encamide, bepridil, verapamil, diltiazem, bretylium, sotalol, amiodarone, ibutilide, propranolol, atropine, adenosine and digoxin. More examples are set forth below.

In some embodiments, the targeting ligand is a DNA topoisomerase inhibitor. Non-limiting examples include a fluoroquinolone antibiotic, irinotecan, topotecan, etoposide, teniposide, lurtotecan, exatecan and rubitecan. Non-limiting examples of DNA intercalators include 7-aminoactinomycin, etihidium, proflavin, daunomycin, doxorubicin, and thalidomide.

In some embodiments, the targeting ligand is an antimetabolite. Non-limiting examples include azathioprine, a mercaptopurine, a pyrimidine, a sulfanilamide drug, methotrexate, tetrahydrofolate, folic acid, pemetrexed, raltitrexed, thioguanine, fludarabine, pentostatin, cladribine, fluorouracil, floxuridine, and gemcitabine.

The targeting ligand may be a disease cell cycle targeting ligand. Non-limiting examples include adenosine, FIAU, FIRU, IVFRU, GCV, PCV, FGCV, FPCV, FHPG, FHBG and guanine.

In some embodiments, the targeting ligand is a gene expression marker. For example, the gene expression marker may be an epidermal growth factor receptor ligand. In further embodiments, the targeting ligand is an angiogenesis targeting ligand. Non-limiting examples include a COX-2 inhibitor, anti-EGF receptor, herceptin, angiostatin, or thalidomide. Examples of COX-2 inhibitors include celecoxib, rofecoxib, and etoricoxib.

Other examples of targeting ligands include tumor markers. Non-limiting examples of tumor markers include PSA, ER, PR, CA-125, CA-199, CEA, AFP, an interferon, BRCA1, HER-2/neu, Cytoxan, p53 and endostatin. The targeting ligand may also be a folate receptor targeting ligand. Examples include folate, methotrexate and tomudex.

The targeting ligand may also be an apoptotic cell targeting ligand. For example, the apoptotic cell targeting ligand may further be defined as a tumor apoptotic cell targeting ligand. Non-limiting examples include a TRAIL monoclonal antibody, a substrate of caspase-3 and a Bcl family member. Examples of a substrate of caspase-3 include a peptide or polypeptide comprising the amino acid sequence aspartic acid-glutamic acid-valine-aspartic acid. Examples of Bcl family members include Bax, Bcl-xL, Bid, Bad, Bak and Bcl-2

In some embodiments, the targeting ligand is a hypoxia targeting ligand. For example, the hypoxia targeting ligand may be a tumor hypoxia targeting ligand, a cardiac ischemia marker, a cardiac viability tissue marker, a congestive heart failure marker, or a rest/stress cardiac tissue marker. Non-limiting examples of tumor hypoxia targeting ligands include annexin V, colchicine, a nitroimidazole, mitomycin, metronidazole, 99mTc-HL91, and Cu-ATSM. Non-limiting examples of cardiac ischemia markers include interleukin-6, tumor necrosis factor alpha, matrix metalloproteinase 9, myeloperoxidase, intercellular and vascular adhesion molecules, soluble CD40 ligand, placenta growth factor, high sensitivity C-reactive protein (hs-CRP), ischemia modified albumin (IMA), free fatty acids, and choline. Non-limiting examples of cardiac viability tissue markers include phospholipase C, myosin light-chain phosphatase, nitric oxide, prostacyclin, endothelin, thromboxane, L-arginine and L-citrulline. Non-limiting examples of congestive heart failure markers include interleukin-1, cardiotrophin-1, insulin-like growth factor, epidermal growth factor, tyrosine kinase receptor, angiotensin II, and metronidazole. Non-limiting examples of rest/stress cardiac tissue markers include a mitogen-activated protein kinase, cyclic adenosine monophosphate, phospholipase C, phosphatidylinositol bisphosphate, isositol trisphosphate, diacylglycerol, a tyrosine kinase, and metronidazole.

Non-limiting examples of peptides contemplated as targeting ligands include neuropeptide Y, calcitonin gene-related peptide, substance P, and vasoactive intestinal peptide. Non-limiting examples of nucleotides contemplated as targeting ligands include adenine, thymine, guanine, cytosine, and uracil. Non-limiting examples of antibodies contemplated as targeting ligands include an antibody that binds to a troponin, tropomyosin, a sarcolemmal, a collagen, a matrix metalloproteinase, or a tissue inhibitor of a matrix metalloproteinase.

In some embodiments, the targeting ligand is an antisense molecule or an siRNA. The targeting ligand may also be glutamate pentapeptide.

In particular embodiments, the targeting ligand is an agent that mimics glucose. Non-limiting examples of agents that mimic glucose include deoxyglucose, glucosamine, tetraacetylated glucosamine, neomycin, kanamycin, gentamycin, paromycin, amikacin, tobramycin, netilmicin, ribostamycin, sisomicin, micromicin, lividomycin, dibekacin, isepamicin, astromicin and aminoglycoside. In particular embodiments, the agent that mimics glucose is glucosamine.

In further embodiments, the targeting ligand is a disease receptor targeting ligand. Non-limiting examples of disease receptor targeting ligands include an estrogen, an androgen, luteinizing hormone, luteinizing hormone releasing hormone (LHRH), transferrin, a progestin, tetraacetate mannose, α-β-tyrosine, tyrosine, a tyrosine derivative, estrone, tamoxifen, and α-methyltyrosine.

Other general aspects of the present invention contemplate a composition comprising a metal ion labeled-chelator-targeting ligand conjugate synthesized by any of the methods described herein. In particular embodiments, the metal ion labeled-chelator-targeting ligand conjugate comprises ethylene dicysteine chelated to a metal ion selected from the group consisting of $^{99m}$Tc, $^{68}$Ga $^{188}$Re, $^{187}$Re and $^{186}$Re; the targeting ligand comprises a ligand selected from the group consisting of glucosamine, deoxyglucose, metronidazole, annexin V, guanine and LHRH; and the conjugation between the chelator and the targeting ligand takes place via an amide bond or an ester bond.

Exemplary anti-cancer compositions include a chelator capable of chelating to a therapeutic radiometallic substance, such as Re-188, Re-187, Re-186, Ho-166, Y-90, Sr-89, or Sm-153, arsenic, cobalt, copper, calcium, selenium, thallium or platinum. Other exemplary anti-cancer ligands include, for example, epipodophyllotoxin, vincristine, docetaxel, paclitaxel, daunomycin, doxorubicin, mitoxantrone, topotecan, bleomycin, gemcitabine, fludarabine and 5-FUDR. In certain particular embodiments, the anti-cancer ligand is methotrexate.

Other aspects of the present invention contemplate a composition comprising a chelator-targeting ligand conjugate synthesized by any of the methods described herein. In certain embodiments, the invention contemplates a composition comprising a metal ion labeled-chelator-targeting ligand conjugate synthesized by any of the methods described herein. In any given composition embodiment, the chelator-targeting ligand conjugate composition may comprise one or more protecting groups at any position of either/both the chelator and/or the targeting ligand, or no protecting groups at all. Furthermore, the chelator or chelator-targeting ligand conjugate may or may not comprise a metal ion.

Embodiments of the present invention also pertain to a composition comprising a metal ion-labeled chelator-targeting ligand conjugate synthesized by any of the methods set forth herein. The composition may include a pharmaceutically acceptable carriers such as glutamic acid and others mild acids and cold metals. In some embodiments, the composition comprises (a) the metal ion labeled-chelator-targeting ligand conjugate comprises ethylenedicysteine chelated to a metal ion selected from the group consisting of $^{99m}$Tc, $^{68}$Ga, $^{188}$Re, and $^{187}$Re; (b) the targeting ligand comprises a ligand selected from the group consisting of glucosamine, deoxyglucose, metronidazole, annexin V, guanine and LHRH; and (c) the conjugation between the chelator and the targeting ligand takes place via an amide bond or an ester bond.

Further embodiments of the present invention include a reagent for preparing an imaging agent, a therapeutic agent or a radio/therapeutic agent, comprising a metal ion labeled-chelator conjugate prepared by any of the methods set forth herein. In specific embodiments, the reagent is a reagent for preparing a chemotherapeutic agent or a radio/chemotherapeutic agent. In some embodiments, the metal ion labeled-chelator-targeting ligand conjugate is between about 90% and about 99.9% pure. In certain embodiments, the metal ion labeled-chelator-targeting ligand conjugate comprises ethylenedicysteine.

The present invention also pertains to kits for preparing an imaging agent, a therapeutic agent, or a radio/therapeutic agent, comprising one or more sealed containers and a predetermined quantity of a composition comprising a chelator-targeting ligand conjugate prepared by any method described herein in one or more sealed containers. In some embodiments, the kit includes a chelator-targeting ligand conjugate that is between about 90% and about 99.9% pure. In some embodiments, the kit includes a chelator-targeting ligand conjugate that is between about 80% and about 99.9% pure. In some embodiments, the kit includes a chelator-targeting ligand conjugate that is between about 70% and about 99.9% pure. In particular embodiments, the kit includes an ethylenedicysteine-targeting ligand conjugate. In some embodiments, the kit further includes a metal ion. The metal ion may or may not be a radionuclide. In particular examples, the metal ion is a cold metal ion (not a radionuclide). In a particular embodiments, the cold metal ion is Re-187. In other examples, the metal ion is a radionuclide. Examples of metal ions include any of those metal ions discussed above. In some embodiments, the kit includes one or more vials containing a composition comprising disodium hydrogen phosphate dehydrate, mannitol, ascorbic acid, sodium edentate, stannous chloride dehydrate, tartaric acid, or potassium dihydrogen-phosphate, and a pharmaceutically acceptable carrier.

Further embodiments of the present invention pertain to an imaging, therapeutic, or radio/therapeutic agent, prepared by a method comprising any of the methods set forth above. In some embodiments, the chelator-targeting ligand conjugate is between about 90% and about 99.9% pure. In some embodiments, the chelator-targeting ligand conjugate is between about 80% and about 99.9% pure. In some embodiments, the chelator-targeting ligand conjugate is between about 70% and about 99.9% pure. In specific embodiments, the metal ion-labeled chelator-targeting ligand conjugate comprises ethylenedicysteine. In particular embodiments, the metal ion labeled chelator-targeting ligand conjugate is $^{99m}$Tc-EC-glucosamine. In further particular embodiments, the metal ion labeled chelator-targeting ligand conjugate is $^{186}$Re-EC-glucosamine. In still further embodiments, the metal ion labeled chelator-targeting ligand conjugate is $^{187}$Re-EC-glucosamine.

Further embodiments pertain to a method of imaging, diagnosing, or treating a subject, comprising administering to the subject a pharmaceutically or diagnostically effective amount of a metal ion labeled chelator-targeting ligand conjugate, wherein the chelator-targeting ligand conjugate is prepared by a method comprising any of the methods set forth above, wherein the disease is imaged, diagnosed, or treated. In certain embodiments, the metal ion labeled-chelator conjugate is between about 90% and about 99.9% pure. In certain embodiments, the metal ion labeled-chelator conjugate is between about 80% and about 99.9% pure. In certain embodiments, the metal ion labeled-chelator conjugate is between about 70% and about 99.9% pure. In particular embodiments, the metal ion labeled-chelator conjugate comprises ethylenedicysteine. The metal ion, for example, may be any of those metal ions set forth above.

Certain embodiments pertain to a method of treating a subject with a hyperproliferative disease, comprising administering to the subject a pharmaceutically effective amount of a metal ion-labeled chelator-targeting ligand conjugate prepared by any of the methods set forth herein. In particular embodiments, the hyperproliferative disease is cancer. For example, the cancer may be breast cancer, lung cancer, prostate cancer, ovarian cancer, brain cancer, liver cancer, cervical cancer, colon cancer, renal cancer, skin cancer, head and neck cancer, bone cancer, a esophageal cancer, bladder cancer, uterine cancer, lymphatic cancer, stomach cancer, pancreatic cancer, testicular cancer, lymphoma, or leukemia. In certain embodiments, the method is further defined as a method for performing dual radio/chemotherapy. Some embodiments further comprise administering one or more secondary forms of therapy of a hyperproliferative disease. For example, the secondary form of therapy may be chemotherapy, gene therapy, surgical therapy, radiation therapy, or immunotherapy. Certain embodiments pertain to methods of performing dual imaging and therapy in a subject.

Embodiments of the present invention also generally pertain to methods of diagnosis, assessing efficacy of treatment, or imaging in a subject with known or suspected cardiovascular disease. The subject can be any subject, such as a mammal or animal models used to assess the presence of cardiovascular disease. The mammal, for example, may be a human or member of the monkey species. Animal models include dogs, cats, rats, mice or rabbits. In preferred embodiments, the subject is a human with known or suspected cardiovascular disease.

The cardiovascular disease can be any disease of the heart or tissue nourished by the vascular system. The vascular system includes coronary arteries, and all peripheral arteries supplying nourishment to the peripheral vascular system and the brain. The vascular system includes arteries, veins, arterioles, venules, and capillaries. Examples of cardiovascular diseases include diseases of the heart, such as myocardial infarction, myocardial ischemia, angina pectoris, congestive heart failure, cardiomyopathy (congenital or acquired), arrhythmia, or valvular heart disease. In particular embodiments, the subject is known or suspected to have myocardial ischemia.

The subject, for example, may be a patient who presents to a clinic with signs or symptoms suggestive of myocardial ischemia or myocardial infarction. Imaging of the heart of the subject to diagnose disease may involve administering to the subject a pharmaceutically effective amount of a metal ion labeled chelator-targeting ligand conjugate synthesized using any of the methods set forth herein. Imaging can be performed using any imaging modality known to those of ordinary skill in the art. In particular embodiments, imaging involves use radionuclide-based imaging technology, such as PET or SPECT. In particular embodiments, the metal ion-labeled radionuclide-targeting ligand conjugate is 99m-Tc-EC-glucosamine. Glucosamine is not actively taken up by viable myocardial tissue but rather is target specific for regions of ischemia. Severity of ischemia can be visually assessed or graded depending on magnitude of the signal that is measured using any method known to those of ordinary skill in the art. In some embodiments, imaging using any of the conjugates set forth herein is performed before, during, or after imaging of the heart using a second imaging agent. For example, the second imaging agent may be thallium imaged by scintigraphy to would define the region of normal myocardial perfusion (non-ischemic tissue).

Myocardial perfusion SPECT (MPS) consist of a combination of a stress modality (exercise or pharmacologic) with rest and stress administration and imaging of radiopharmaceuticals. Thallium has excellent physiologic properties for myocardial perfusion imaging. Being highly extracted during the first pass through the coronary circulation, a linear relationship between blood flow to viable myocardium and thallium uptake has been shown during exercise; however, at very high levels of flow, a "roll-off" in uptake occurs. As an unbound potassium analogue, thallium redistributes over time. Its initial distribution is proportional to regional myocardial perfusion and at equilibrium, the distribution of thallium is proportional to the regional potassium pool, reflecting viable myocardium. The mechanisms of thallium redistribution are differential washout rates between hypoperfused but viable myocardium and normal zones and wash-in to initially hypoperfused zones. The washout rate of thallium is the concentration gradient between the myocardial cell and the blood. There is slower blood clearance of thallium following resting or low-level exercise injection. Diffuse slow washout rates, mimicking diffuse ischemia, may be observed in normal patients who do not achieve adequate levels of stress. Hyperinsulinemic states slow redistribution, leading to an underestimation of viable myocardium; thus fasting is recommended prior to and for 4 hrs following thallium injection. This is why if EC-G is used as an viable agent in combination with thallium it will target the precise area of interest which would be the Ischemic but viable area (see Angello et al., 1987; Gutman et al., 1983; Pohost et al., 1977).

Imaging using any of the metal ion-labeled chelator-targeting ligand conjugates of the present invention may also be performed in conjunction with other diagnostic methods, such as measurement of cardiac isozymes, or cardiac catheterization. The imaging may be performed at various intervals following onset of symptoms, or can be performed to assess for changes in myocardial perfusion over time.

Further embodiments pertain to a method of imaging a site within a subject comprising (a) administering to the subject a diagnostically effective amount of a metal ion labeled-chelator-targeting ligand conjugate, wherein the metal ion-labeled chelator-targeting ligand conjugate is synthesized by any of the methods set forth herein; and (b) detecting a signal from the metal ion labeled-chelator-targeting ligand conjugate that is localized at the site. In certain embodiments, the metal ion labeled-chelator-targeting ligand conjugate is between about 90% and about 99.9% pure. In specific embodiments, the metal ion labeled-chelator-targeting ligand conjugate comprises ethylenedicysteine.

The signal can be detected by any method known to those of ordinary skill in the art. Non-limiting examples of such methods include PET, PET/CT, CT, SPECT, SPECT/CT, MRI, optical imaging and ultrasound.

The subject can be any subject, such as a mammal or avian species. In particular embodiments, the mammal is a human. The site to be imaged can be any site in a subject, and may include, for example, a tumor, heart, lung, esophagus, muscle, intestine, breast, prostate, stomach, bladder, liver, spleen, pancreas, kidney, a tumor, duodenum, jejunum, ileum, cecum, colon, rectum, salivary gland, gall bladder, urinary bladder, trachea, larynx, pharynx, aorta, artery, vein, thymus, lymph node, bone, pituitary gland, thyroid gland, parathyroid gland, adrenal gland, brain, cerebrum, cerebellum, medulla, pons, spinal cord, nerve, skeletal muscle, smooth muscle, bone, testes, epidiymides, prostate, seminal vesicles, penis, ovary, uterus, mammary gland, vagina, skin, eyes, or optic nerve. In particular embodiments, the site to be imaged is a tumor. In further particular embodiments, the site to be imaged is the heart.

In some embodiments, the method of imaging further comprises performing one or more additional diagnostic or imaging procedures to evaluated the subject for a disease. In further embodiments, the method of imaging is further defined as a method of performing dual imaging and therapy.

In certain embodiments, the disease to be treated is a cardiovascular disease. Non-limiting examples of such diseases include myocardial infarction, congestive heart failure, cardiomyopathy, valvular heart disease, an arrhythia, congenital heart disease, and angina pectoris.

The present invention also generally pertains to methods for imaging the brain or spinal cord (neuroendocrine system) of a subject, comprising administering to a subject one or more of the conjugates of the present invention. In some embodiments, for example, the chelate is conjugated to a targeting ligand that is capable of crossing the blood-brain barrier of a subject. A non-limiting example of such a targeting ligand is an amino acid, such as tyrosine or an analog of tyrosine such as alpha-methyl tyrosine. Other examples include somatostatin, octreotide, and tryptophan.

The present invention also generally pertains methods of treating a subject with a disorder of the central nervous system of a subject. The disorder of the central nervous system may be, for example, a neurodegenerative disease such as Parkinson's disease, Huntington's disease, amyotrophic lateral sclerosis, Alzheimer disease, or a neuroendocrine tumor. Examples of neuroendocrine tumors include primary and metastatic brain tumors. Examples of primary brain tumors include astrocytomas, glioblastomas, oligodendrogliomas, ependymomas, mixed gliomas, mixed glioneuronal tumors (tumors displaying a neuronal, as well as a glial component, e.g. gangliogliomas, disembryoplastic neuroepithelial tumors) and tumors originating from neuronal cells (e.g., gangliocytoma, central gangliocytoma). The tumor may be a metastatic tumor. In some embodiments, the disorder of the central nervous system is an inflammatory disease. For example, the disease may be an infectious disease, or an immune disease.

The present invention also pertains to a method of determining the purity of a composition comprising a metal ion labeled-chelator-targeting ligand conjugate of unknown purity is also contemplated by the present invention, said method comprising:
a) obtaining a first composition comprising a metal ion labeled-chelator-targeting ligand conjugate of unknown purity;
b) obtaining a second composition comprising a metal ion labeled-chelator-targeting ligand conjugate prepared by any of the methods described herein;
c) performing quantitative analysis on a sample of the first composition to generate a first measurement;
d) performing quantitative analysis of the second composition to generate a second measurement; and
e) calculating a ratio of the first measurement to the second measurement, wherein the ratio of the first measurement to the second measurement is a measure of purity of the composition comprising a metal ion labeled-chelator-targeting ligand conjugate of unknown purity.

Quantitative analysis may be performed via any technique known to those of skill in the art. In certain embodiments, quantitative analysis is performed by technique selected from the group consisting of autoradiography, dialysis, mass spectroscopy, melting point determination, ultra violet analysis, colorimetric analysis, high-performance liquid chromatography, thin-layer chromatography and nuclear magnetic resonance analysis.

Other aspects of the present invention contemplate a composition comprising a chelator-targeting ligand conjugate, wherein the chelator is of the following formula:

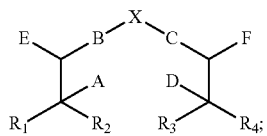

wherein:
the point of conjugation between the chelator and the targeting ligand is at one or more positions selected from the group consisting of A, B, C, D, E and F;
A, D, E and F are each independently H, lower alkyl, —COOH, —NH$_2$, or thiol, with the proviso that at least one position is —NH$_2$ or thiol;
B and C are each independently a secondary amine, a tertiary amine, —S—, —S(O)—, or —S(O)$_2$—;
R$_1$, R$_2$, R$_3$ and R$_4$ are each independently H or lower alkyl; and
X is selected from the group consisting of —CH$_2$—CH$_2$—, —CH$_2$—CH$_2$—CH$_2$—, —CH$_2$—C(O)—, —C(O)—CH$_2$—, —C(O)—CH$_2$—CH$_2$— and —CH$_2$—CH$_2$—C(O)—;
wherein at least one of A, B, C, D, E, F, or one functional group of the targeting ligand is protected by a protecting group, and
wherein the chelator-targeting ligand conjugate is between about 75% and about 99.9% pure.

The protecting group may be of any type described herein. The targeting ligand may be of any type described herein. In certain embodiments, the composition has the proviso that when A and D are each —NH$_2$, neither B nor C is a secondary or a tertiary amine. The composition may comprise a chelator-targeting ligand conjugate that is between about 70% and about 99.9% pure. The composition may comprise a chelator-targeting ligand conjugate that is between about 80% and about 99.9% pure. The composition may comprise a chelator-targeting ligand conjugate that is between about 85% and about 99.9% pure. The composition may comprise a chelator-targeting ligand conjugate that is between about 90% and about 99.9% pure. The composition may comprise a chelator-targeting ligand conjugate that is between about 95% and about 99.9% pure. The composition may, in certain embodiments, be further defined as a metal ion labeled-chelator-targeting ligand conjugate, as discussed herein.

Another aspect of the present invention contemplates a composition comprising a chelator-targeting ligand conjugate, wherein the chelator is of the following formula:

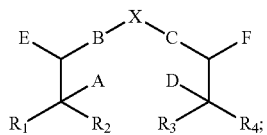

wherein:
the point of conjugation between the chelator and the targeting ligand is at one or more positions selected from the group consisting of A, B, C, D, E and F;
A, D, E and F are each independently H, lower alkyl, —COOH, —NH$_2$, or thiol, with the proviso that at least one position is —NH$_2$ or thiol;
B and C are each independently a secondary amine, a tertiary amine, —S—, —S(O)—, or —S(O)$_2$—;
R$_1$, R$_2$, R$_3$ and R$_4$ are each independently H or lower alkyl; and
X is selected from the group consisting of —CH$_2$—CH$_2$—, —CH$_2$—CH$_2$—CH$_2$—, —CH$_2$—C(O)—, —C(O)—CH$_2$—, —C(O)—CH$_2$—CH$_2$— and —CH$_2$—CH$_2$—C(O)—;
wherein the chelator-targeting ligand conjugate is between about 75% and about 99.9% pure.

The targeting ligand may be of any type described herein. In certain embodiments, the composition has the proviso that when A and D are each —NH$_2$, neither B nor C is a secondary or a tertiary amine. The composition may comprise a chelator-targeting ligand conjugate that is between about 70% and about 99.9% pure. The composition may comprise a chelator-targeting ligand conjugate that is between about 80% and about 99.9% pure. The composition may comprise a chelator-targeting ligand conjugate that is between about 85% and about 99.9% pure. The composition may comprise a chelator-targeting ligand conjugate that is between about 90% and about 99.9% pure. The composition may comprise a chelator-targeting ligand conjugate that is between about 95% and about 99.9% pure. The composition may, in certain embodiments, be further defined as a metal ion labeled-chelator-targeting ligand conjugate, as discussed herein. The composition may be further defined as $^{99}$mTc-EC-glucosamine. The composition may be further defined as $^{186}$Re-EC-glucosamine. The composition may be further defined as $^{187}$Re-EC-glucosamine.

It is contemplated that any embodiment discussed in this specification can be implemented with respect to any method, compound or composition of the invention, and vice versa. Furthermore, compounds and compositions of the invention can be used to achieve methods of the invention.

A person of ordinary skill in the art will recognize that chemical modifications can be made to the compounds of the present invention, as well as compounds employed in the method of the present invention, without departing from the spirit and scope of the present invention. Substitutes, derivatives, or equivalents can also be used, all of which are contemplated as being part of the present invention.

As used herein, "organic medium" refers to solutions (e.g., reaction solutions) and purification methods comprising one or more organic solvents (also called "solvents" herein). Solvent choices for the methods of the present invention will be known to one of ordinary skill in the art. Solvent choices may depend, for example, on which one(s) will facilitate the solubilizing of all the reagents, or, for example, which one(s) will best facilitate the desired reaction (particularly if the mechanism of the reaction is known). Solvents may include, for example, polar solvents and non-polar solvents. Solvents choices include, but are not limited to, dimethylformamide, dimethylsulfoxide, dioxane, methanol, ethanol, hexane, methylene chloride and acetonitrile. In some preferred embodiments, solvents include ethanol, dimethylformamide and dioxane. More than one solvent may be chosen for any particular reaction or purification procedure. Water (i.e., an aqueous component) may also be admixed into any solvent choice; water is typically added to facilitate solubilization of all the reagents. In certain embodiments, the organic component of the organic medium, by volume, is about or at least about 20%, 25%, 30%, 35%, 40%, 45%, 50%, 55%, 60%, 65%, 70%, 75%, 80%, 85%, 90%, 95%, or 100% organic solvent compared to the aqueous component.

The word "conjugate" and "conjugated" is defined herein as chemically joining within the same molecule. For example, two or more molecules and/or atoms may be conjugated together via a covalent bond, forming a single molecule. The two molecules may be conjugated to each other via a direct connection (e.g., where the compounds are directly attached via a covalent bond) or the compounds may be conjugated via an indirect connection (e.g., where the two compounds are covalently bonded to one or more linkers, forming a single molecule). In other instances, a metal atom may be conjugated to a molecule via a chelation interaction.

The term "functional group" generally refers to how persons of skill in the art classify chemically reactive groups. Non-limiting examples of functional groups include carbon-carbon bonds (including single, double and triple bonds), hydroxyl (or alcohol), amine, sulfhydryl (or thiol), amide, ether, ester, thioether, thioester, carboxylic acid and carbonyl groups. As used herein, "amine" and "amino" and other similar pairs of words such as "hydroxy" and "hydroxyl" refer to the same functional moiety and thus are used interchangeably. As used herein, "amine" may refer to either or both —NH$_2$ and —NH—.

As used herein, "chelate" may be used as a noun or a verb. As a noun, "chelate" refers to one or more atoms that are either capable of chelating one or more metal ions, or are chelating to one or more metal ions. In preferred embodiments, only one metal ion coordinates to a chelate. A non-limiting example of "chelate" includes "an N$_2$S$_2$" chelate: this means that two nitrogen atoms and two sulfur atoms of a chelator are either a) capable of chelating to one or more metal ions or b) are coordinated to (or chelated to) to one or more metal ions (preferably just one metal ion). As a verb, "chelate" refers to the process of a metal ion becoming coordinated or chelated to, for example, a chelator or a chelator-targeting ligand conjugate.

As used herein, an "unconjugated chelator" refers to a chelator that is not conjugated to a targeting ligand.

As used herein, an "unprotected chelator" refers to a chelator that does not comprise any protecting groups.

As used herein, a "protected chelator" refers to a chelator that comprises at least one protecting group.

As used herein, an "unprotected targeting ligand" refers to a targeting ligand that does not comprise any protecting groups.

As used herein, a "protected targeting ligand" refers to a targeting ligand that comprises at least one protecting group.

The term "nucleophile" or "nucleophilic" generally refers to atoms bearing one or more lone pairs of electrons. Such terms are well known in the art and include —NH$_2$, thiolate, carbanion and alcoholate (also known as hydroxyl).

The term "electrophile" or "electrophilic" generally refers to species that react with nucleophiles. Electrophilic groups typically have a partial positive charge. Such a term is well known in the art and includes the carbon of a carbon bonded to a leaving group such as a halogen, sulfonyl, or a quarternary amino group.

The term "leaving group" generally refers to groups readily displaceable by a nucleophile, such as an amine, and alcohol or a thiol nucleophile. Such leaving groups are well known and include carboxylates, N-hydroxysuccinimide, N-hydroxybenzotriazole, halogen (halides), triflates, tosylates, mesylates, alkoxy, thioalkoxy, sulfonyls and the like.

As used herein, "alkyl" or "alk" refers to a straight, branched or cyclic carbon-carbon or hydrocarbon chain, optionally including alkene or alkyne bonding, containing 1-30 carbons. "Lower alkyl" refers to alkyl radicals comprising 1-4 carbons. Non-limiting examples of lower alkyls include methyl, ethyl, propyl, butyl and isopropyl. "Substituted alkyl" refers to an alkyl radical substituted with at least one atom known to those of skill in the art. In certain embodiments, one or more substituents may be selected from the group consisting of hydrogen, halogen, oxo (e.g., ether), hydroxy, alkoxy, silyloxy, cycloalkyl, acyl, aryl, acetyl, carbonyl, thiocarbonyl, cyano, azido, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, NO$_2$ and sulfo (e.g., thioether, thioester, sulfonamido, sulfonyl).

The term "aryl" refers to a carbocyclic aromatic group, including but not limited to those selected from the group consisting of phenyl, naphthyl, indenyl, indanyl, azulenyl, fluorenyl, and anthracenyl; or a heterocyclic aromatic group, including but not limited to those selected from the group consisting of furyl, furanyl, thienyl, pyridyl, pyrrolyl, oxazolyl, thiazolyl, imidazolyl, pyrazolyl, pyrazolinyl, pyrazolidinyl, isoxazolyl, isothiazolyl, oxadiazolyl, triazolyl, thiadiazolyl, pyridazinyl, pyrimidinyl, pyrazinyl, triazinyl, trithianyl, indolizinyl, indolyl, isoindolyl, indolinyl, thiophenyl, indazolyl, benzimidazolyl, benzthiazolyl, purinyl, quinolizinyl, quinolinyl, isoquinolinyl, innolinyl, phthalazinyl, quinazolinyl, quinoxalinyl, naphthyridinyl, pteridinyl carbazolyl, acridinyl, phenazinyl, phenothiazonyl, phenoxazinyl and any combination or derivative of one or more of these groups.

"Aryl" groups, as defined in this application may independently contain one or more functional groups as substituents. In certain embodiments, substituents may be selected from the group consisting of hydrogen, alkyl, halogen, oxo (e.g., ether), hydroxy, alkoxy, silyloxy, cycloalkyl, acyl, aryl, acetyl, carbonyl, thiocarbonyl, cyano, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, NO$_2$ and sulfo (e.g., thioether, thioester, sulfonamido, sulfonyl). Further, any of these substituents may be further substituted with substituents as just described.

As used herein the term "cycloalkyl" refers to carbocycles or heterocycles of three or more atoms, the ring atoms of which may be optionally substituted with C, S, O or N, and the ring atoms of which may comprise one or more functional group as substituents. Substituents may be selected, in some embodiments, from the group consisting of hydrogen, alkyl, halogen, oxo (e.g., ether), hydroxy, alkoxy, silyloxy, cycloalkyl, acyl, aryl, acetyl, carbonyl, thiocarbonyl, cyano, azido, amido, aminocarbonyl, amino, —NH-alkyl, —N(alkyl)$_2$, —NH-cycloalkyl, —N(cycloalkyl)$_2$, —NH-aryl, —N(aryl)$_2$, trialkylsilyloxy, acyloxy, acylamino, bis-acylamino, ester, NO, NO$_2$ and sulfo (e.g., thioether, thioester, sulfonamido, sulfonyl).

The term "amino acid" refers to any of the naturally occurring amino acids, as well as synthetic analogs (e.g., D-stereoisomers of the naturally occurring amino acids, such as D-threonine) and derivatives thereof α-Amino acids comprise a carbon atom to which is bonded an amino group, a carboxyl group, a hydrogen atom, and a distinctive group referred to as a "side chain." Amino acids comprising an additional methylene group in their backbone are often called β-amino acids. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (1989); Evans et al. (1990); Pu et al. (1991); Williams et at (1991); and all references cited therein. The present invention includes the side chains of unnatural amino acids as well.

The terms "primary amine," "secondary amine" and "tertiary amine" refer to amines, as derivatives of ammonia (NH$_3$), in which one (primary), two (secondary) or three (tertiary) of the hydrogens have been replaced by carbon, wherein said carbon may be attached to any other atom. In certain embodiments, said carbon (C) is comprised in X of the formula shown above, a hydrocarbon group (e.g., —CH$_2$—), —CH(E)(CHAR$_1$R$_2$), —CH(F)(CHDR$_3$R$_4$), or a —C(O)— group, wherein A, D, E, F, X, R$_1$, R$_2$, R$_3$ and R$_4$ are as defined herein.

Compounds as described herein may contain one or more asymmetric centers and thus can occur as racemates and racemic mixtures, single enantiomers, diastereomeric mixtures and individual diastereomers. All possible stereoisomers of the all the compounds described herein, unless otherwise noted, are contemplated as being within the scope of the present invention. The chiral centers of the compounds of the present invention can have the S— or the R-configuration, as defined by the IUPAC 1974 Recommendations. The present invention is meant to comprehend all such isomeric forms of the compounds of the invention.

The claimed invention is also intended to encompass salts of any of the synthesized compounds of the present invention. The term "salt(s)" as used herein, is understood as being acidic and/or basic salts formed with inorganic and/or organic acids and bases. Zwitterions (internal or inner salts) are understood as being included within the term "salt(s)" as used herein, as are quaternary ammonium salts such as alkylammonium salts. Nontoxic, pharmaceutically acceptable salts are preferred as described below, although other salts may be useful, as for example in isolation or purification steps.

Non-limiting examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate and undecanoate.

Non-limiting examples of basic salts include but are not limited to ammonium salts; alkali metal salts such as sodium, lithium, and potassium salts; alkaline earth metal salts such as calcium and magnesium salts; salts comprising organic bases such as amines (e.g., dicyclohexylamine, alkylamines such as t-butylamine and t-amylamine, substituted alkylamines, aryl-alkylamines such as benzylamine, dialkylamines, substituted dialkylamines such as N-methyl glucamine (especially N-methyl D-glucamine), trialkylamines, and substituted trialkylamines); and salts comprising amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myrtistyl and stearyl chlorides, bromides and iodides), arylalkyl halides (e.g. benzyl and phenethyl bromides) and others known in the art.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects. For example, "about" can be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8A and 8B. Stability of $^{68}$Ga-EC-G in dog serum as shown by radio-TLC. (a) $^{68}$Ga-EC-G (0.7 mg/0.7 ml, pH 7.5, 865 µCi); (b) 100 µL $^{68}$Ga-EC-G in 100 µL dog serum, time=0; (c) time=30 min.; (d) time=60 min.; (e) time=120 min.; (f) $^{68}$Ga-EC-BSA.

DESCRIPTION OF ILLUSTRATIVE EMBODIMENTS

Figure 1:
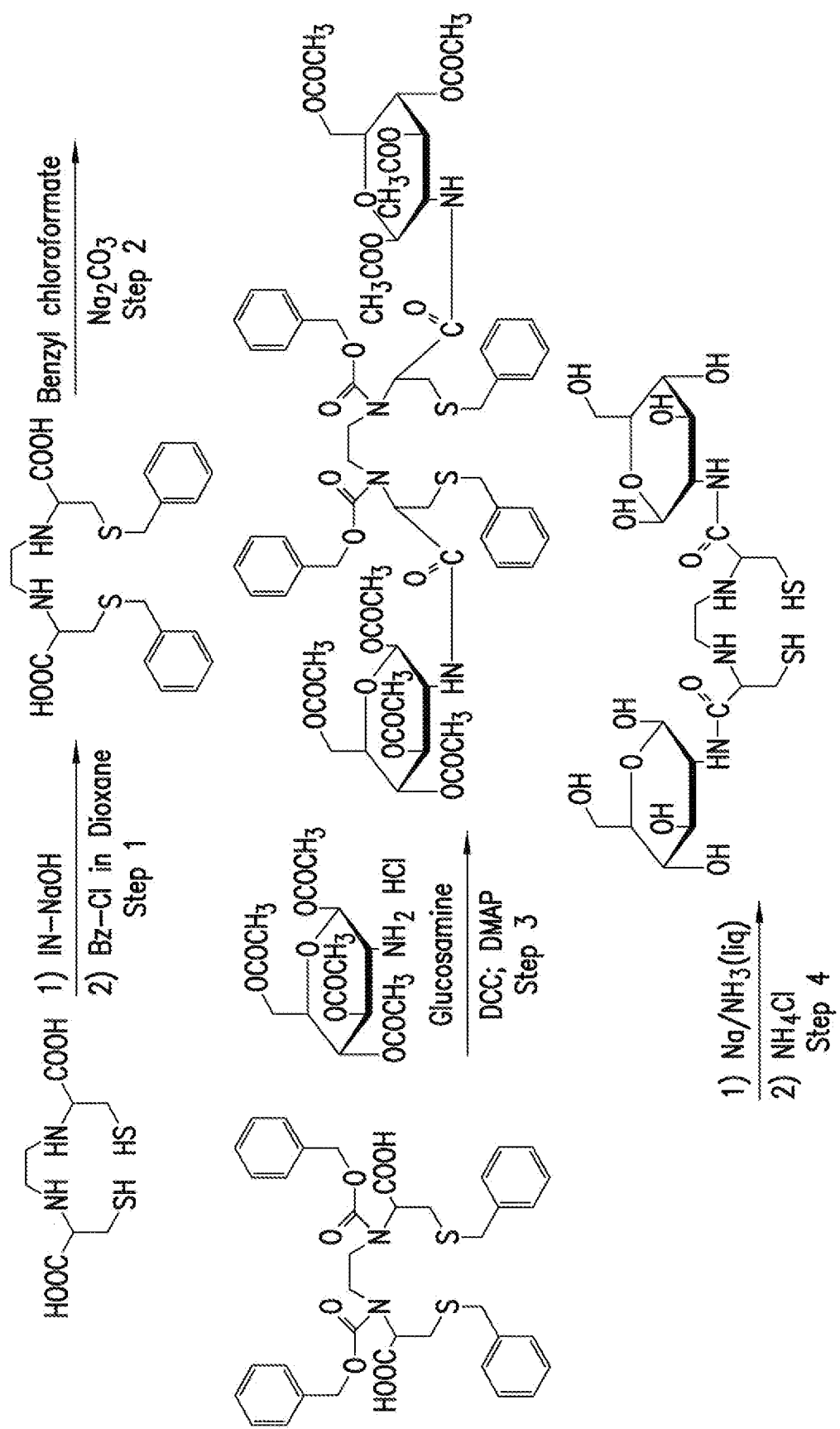
FIG. 1. Non-limiting example of an organic synthesis of ethylenedicysteine-glucosamine (EC-G).

The present inventors have identified novel synthetic methods for the preparation of chelator-targeting ligand conjugates optionally chelated to one or more metal ions. The present invention further provides syntheses of chelators, such as unconjugated chelators, protected chelators (that is, chelators wherein one or more functional groups are protected using a protecting agent) and metal ion labeled-chelators (that is, chelators that are chelated to one or more metal ions). These synthetic methods comprise, generally, the use of organic solvents and synthetic organic procedures and purification methods. Methods based on wet (aqueous) chemistry are also provided. Compounds of the present invention resulting from such organic chemistry methods are high in purity, especially when compared to compounds prepared by wet chemistry. A preferred chelator is ethylenedicysteine. The targeting ligand can be, for example, a tissue-targeting moiety, a diagnostic moiety, or a therapeutic moiety. The metal ions chelated to compounds of the present invention may further render the compound useful for imaging, diagnostic, or therapeutic use. Compounds of the present invention, methods of their synthesis and use are further described below.

A. CHELATORS

Persons of skill in the art will be familiar with compounds capable of chelating one or more metal ions ("chelators"). Chelators employed in the method of the present invention generally comprise one or more atoms capable of chelating to one or more metal ions. Chelators comprising three or four atoms available for chelation are preferred. Typically, a chelator chelates to one metal ion.

Chelation of a metal ion to a chelator can be by any method known to those of ordinary skill in the art. Methods of chelation (also called coordination) are described in more detail below. Atoms available for chelation are known to those of skill in the art, and typically comprise O, N or S. In preferred embodiments, the atoms available for chelation are selected from the group consisting of N and S. In certain preferred embodiments, the metal ion is chelated to a group of atoms, referred to herein as "chelates," selected from the group consisting of $NS_2$, $N_2S$, $S_4$, $N_2S_2$, $N_3S$ and $NS_3$. Chelation can also occur among both the chelator and the targeting ligand—i.e., both the chelator and the targeting ligand may contribute atoms that chelate the same metal ion.

In certain embodiments, the chelator comprises compounds incorporating one or more amino acids. Amino acids will typically be selected from the group consisting of cysteine and glycine. For example, the chelator may comprise three cysteines and one glycine or three glycines and one cysteine. As discussed below, a spacer may connect one amino acid to another.

It is well known to those of ordinary skill in the art that chelators, in general, comprise a variety of functional groups. Non-limiting examples of such functional groups include hydroxy, thiol, amine, amido and carboxylic acid.

1. Bis-aminoethanethiol (BAT) Dicarboxylic Acids

Bis-aminoethanethiol (BAT) dicarboxylic acids may constitute a chelator employed in the method of the present invention. In preferred embodiments, the BAT dicarboxylic acid is ethylenedicysteine (EC). BAT dicarboxylic acids are capable of acting as tetradentate ligands, and are also known as diaminodithiol (DADT) compounds. Such compounds are known to form stable Tc(V)O-complexes on the basis of efficient binding of the oxotechnetium group to two thiol-sulfur and two amine-nitrogen atoms. The $^{99m}$Tc labeled diethylester ($^{99m}$Tc-L,L-ECD) is known as a brain agent. $^{99m}$Tc-L,L-ethylenedicysteine ($^{99m}$Tc-L,L-EC) is its most polar metabolite and was discovered to be excreted rapidly and efficiently in the urine. Thus, $^{99m}$Tc-L,L-EC has been used as a renal function agent. (Verbruggen et al. 1992). Other metals such as indium, rhenium, gallium, copper, holmium, platinum, gadolinium, lutecium, yttrium, cobalt, calcium and arsenic may also be chelated to BAT dicarboxylic acids such as EC.

2. Spacers

Chelators of the present invention may comprise one or more spacers. For example, amino acids and their derivatives may be joined by one or more spacers. An example of two amino acids joined by a spacer includes ethylenedicysteine, described above. Such spacers are well known to those of ordinary skill in the art. These spacers, in general, provide additional flexibility to the overall compound that may facilitate chelation of one or more metal ions to the chelator. Non-limiting examples of spacers include alkyl groups of any length, such as ethylene (—$CH_2$—$CH_2$—), ether linkages, thioether linkages, amine linkages and any combination of one or more of these groups. It is envisioned that multiple chelators (that is, two or more) linked together are capable of forming an overall molecule that may chelate to one or more, or more typically two or more, metal ions. That is, each chelator that makes up the overall molecule may each chelate to a single separate metal ion.

B. PROTECTING GROUPS

When a chemical reaction is to be carried out selectively at one reactive site in a multifunctional compound, other reactive sites often must be temporarily blocked. A "protecting group," as used herein, is defined as a group used for the purpose of this temporary blockage. Thus, the function of a protecting group is to protect one or more functional groups (e.g., —$NH_2$, —SH, —COOH) during subsequent reactions which would not proceed well, either because the free (in other words, unprotected) functional group would react and be functionalized in a way that is inconsistent with its need to be free for subsequent reactions, or the free functional group would interfere in the reaction. Persons of skill in the art recognize that the use of protecting groups is typical in synthetic organic chemistry.

During the synthesis of the compounds of the present invention, various functional groups must be protected using protecting agents at various stages of the synthesis. A "protecting agent" is used to install the protecting group. Thus, in a typical procedure, a protecting agent is admixed with a compound featuring a functional group that is to be protected, and the protecting agent forms a covalent bond with that functional group. In this manner, the functional group is "protected" by a protecting group (and effectively rendered unreactive) by the covalent bond that formed with the protecting agent. Multiple functional groups can be protected in one or more steps using properly selected protecting agents. Such proper selection is understood by those of skill in the art. Such selection is often based upon the varying reactivity of the functional groups to be protected: thus, more reactive groups (such as sulfur/thiol) are typically protected before less reactive groups (such as amine) are protected.

There are a number of methods well known to those skilled in the art for accomplishing such a step. For protecting agents, their reactivity, installation and use, see, e.g., Greene and Wuts (1999), herein incorporated by reference in its entirety. The same protecting group may be used to protect one or more of the same or different functional group(s). Non-limiting examples of protecting group installation are described below.

Use of the phrase "protected hydroxy" or "protected amine" and the like does not mean that every such functional group available to be protected is protected. Similarly, a "protected chelator," as used herein, does not imply that every functional group of the chelator is protected.

Compounds of the present invention, including compounds used and made during the practice of the method of the present invention, are contemplated both in protected and unprotected (or "free") form. Persons of ordinary skill in the art will understand that functional groups necessary for a desired transformation should be unprotected.

When a protecting group is no longer needed, it is removed by methods well known to those skilled in the art. For deprotecting agents and their use, see, e.g., Greene and Wuts (1999). Agents used to remove the protecting group are typically called deprotecting agents. Protecting groups are typically readily removable (as is known to those skilled in the art) by methods employing deprotecting agents that are well known to those skilled in the art. For instance, acetate ester and carbamate protecting groups may be easily removed using mild acidic or basic conditions, yet benzyl and benzoyl ester protecting groups need much stronger acidic or basic conditions. It is well known that certain deprotecting agents remove some protective groups and not others, while other deprotecting agents remove several types of protecting groups from several types of functional groups. For instance, Birch reduction reactions using liquid ammonia and sodium (as described below) deprotect benzyl groups from thiols (or sulfur, more particularly) or carbamate groups from nitrogen, but not acetate groups from oxygen. Thus, a first deprotecting agent may be used to remove one type of protecting group, followed by the use of a second deprotecting agent to remove a second type of protecting group, and so on.

Persons of ordinary skill in the art will be familiar with the proper ordering of protective group removal using deprotecting agents. See e.g., Greene and Wuts (1999). Non-limiting examples of protecting group removal are discussed below.

Amine protecting groups are well known to those skilled in the art. See, for example, Greene and Wuts (1999), Chapter 7. These protecting groups can be installed via protecting agents well known to those of skill in the art. Removal of these groups is also well known to those of skill in the art.

In some embodiments, the amine protecting group may be selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, benzyl chloroformate, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluoylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl, 1-piperidyloxycarbonyl and 9-fluorenylmethyl carbonate.

In some embodiments, the protecting agent for amine protection is selected from the group consisting of benzylchloroformate, p-nitro-chlorobenzylformate, ethylchloroformate, di-tert-butyl-dicarbonate, triphenylmethyl chloride and methoxytriphenylmethyl chloride. In a preferred embodiment, the protecting group is benzyloxycarbonyl, installed by the protecting agent benzyloxychloroformate.

Thiol protecting groups are well known to those skilled in the art. See, for example, Greene and Wuts (1999), Chapter 6. These protecting groups can be installed via protecting agents well known to those of skill in the art. Removal of these groups is also well known to those of skill in the art.

In some embodiments, a thiol protecting group may be selected from the group consisting of acetamidomethyl, benzamidomethyl, 1-ethoxyethyl, benzoyl, triphenylmethyl, t-butyl, benzyl, adamantyl, cyanoethyl, acetyl and trifluoroacetyl.

In some embodiments, the protecting agent for thiol protection is selected from the group consisting of an alkyl halide, a benzyl halide, a benzoyl halide, a sulfonyl halide, a triphenylmethyl halide, a methoxytriphenylmethyl halide and cysteine. Non-limiting examples of these protecting agents include ethyl halides, propyl halides and acetyl halides. Halides may comprise chloro, bromo or iodo, for example. In a preferred embodiment, the protecting group is benzyl, installed by the protecting agent benzyl chloride.

Hydroxy (or alcohol) protecting groups are well known to those skilled in the art. See, for example, Greene and Wuts (1999), Chapter 2. These protecting groups can be installed via protecting agents well known to those of skill in the art. Removal of these groups is also well known to those of skill in the art.

A suitable hydroxy protecting group may be selected from the group consisting of esters or ethers. Esters such as acetate, benzoyl, tert-butylcarbonyl and trifluoroacetyl groups are removable by acidic or basic conditions. Ethers such as methoxy, ethoxy and tri-benzylmethyl are removable by stronger acidic or basic conditions. A preferred protecting group is an acetate ester.

Carbonyl protecting groups are well known to those skilled in the art. See, for example, Greene and Wuts (1999), Chapter 4. Such protecting groups may protect, for example, ketones or aldehydes, or the carbonyl present in esters, amides, esters and the like. These protecting groups can be installed via protecting agents well known to those of skill in the art. Removal of these groups is also well known to those of skill in the art.

In some embodiments, a carbonyl protecting group may be selected from the group consisting of dimethylacetal, dimethylketal, diisopropylacetal, diisopropylketal, enamines and enol ethers.

Carboxylic acid protecting groups are well known to those skilled in the art. See, for example, Greene and Wuts (1999), Chapter 5. Removal of these groups is also well known to those of skill in the art.

A suitable carboxylic acid protecting group may be selected from the group consisting of amides or esters, for example. Amides such as sulfonamide, para-nitroaniline, benzylamide and benzolyamide may be hydrolyzed in acidic conditions. Esters such as methyl ester, ethyl ester and benzyl ester may be hydrolyzed by acidic or basic conditions. A preferred protecting group is an amide.

C. METAL IONS

As set forth above, certain embodiments of the present invention pertain to compositions that will function to chelate one or more metal ions. The targeting ligands of the present invention may also participate in chelating one or more metal ions. A "metal ion" is defined herein to refer to a metal ion that is capable of forming a bond, such as a non-covalent bond, with one or more atoms or molecules. The other atom(s) or molecule(s) may be negatively charged.

Any metal ion known to those of ordinary skill in the art is contemplated for inclusion in the compositions of the present invention. One of ordinary skill in the art would be familiar with the metal ions and their application(s). In some embodiments, the metal ion may be selected from the group consisting of Tc-99m, Cu-60, Cu-61, Cu-62, Cu-67, In-111, Tl-201, Ga-67, Ga-68, As-72, Re-186, Re-187, Re-188, Ho-166, Y-90, Sm-153, Sr-89, Gd-157, Bi-212, Bi-213, Fe-56, Mn-55, Lu-177, a iron ion, a arsenic ion, a selenium ion, a thallium ion, a manganese ion, a cobalt ion, a platinum ion, a rhenium ion, a calcium ion and a rhodium ion. For example, the metal ion may be a radionuclide. A radionuclide is an isotope of artificial or natural origin that exhibits radioactivity. In some embodiments, the radionuclide is selected from the group consisting of $^{99m}$Tc, $^{188}$Re, $^{186}$Re, $^{153}$Sm, $^{166}$Ho, $^{90}$Y, $^{89}$Sr, $^{67}$Ga, $^{68}$Ga, $^{111}$In, $^{148}$Gd, $^{55}$Fe, $^{225}$Ac, $^{212}$Bi, $^{211}$At, $^{45}$Ti, $^{60}$Cu, $^{61}$Cu, $^{67}$Cu, and $^{64}$Cu. In preferred embodiments, the metal ion is rhenium or a radionuclide such as $^{99m}$Tc, $^{188}$Re, or $^{68}$Ga. As described below, a reducing agent may need to accompany one of the radionuclides, such as $^{99m}$Tc. Non-limiting examples of such reducing agents include a dithionite ion, a stannous ion and a ferrous ion.

Due to better imaging characteristics and lower price, attempts have been made to replace the $^{123}$I, $^{131}$I, $^{67}$Ga and $^{111}$In labeled compounds with corresponding $^{99m}$Tc labeled compounds when possible. Due to favorable physical characteristics as well as extremely low price ($0.21/mCi), $^{99m}$Tc has been preferred to label radiopharmaceuticals.

A number of factors must be considered for optimal radioimaging in humans. To maximize the efficiency of detection, a metal ion that emits gamma energy in the 100 to 200 keV range is preferred. A "gamma emitter" is herein defined as an agent that emits gamma energy of any range. One of ordinary skill in the art would be familiar with the various metal ions that are gamma emitters. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site. $^{99m}$Tc is a preferred radionuclide because it emits gamma radiation at 140 keV, it has a physical half-life of 6 hours, and it is readily available on-site using a molybdenum-99/technetium-99m generator. One of ordinary skill in the art would be familiar with methods to determine optimal radioimaging in humans.

In certain particular embodiments of the present invention, the metal ion is a therapeutic metal ion. For example, in some embodiments, the metal ion is a therapeutic radionuclide that is a beta-emitter. As herein defined, a beta emitter is any agent that emits beta energy of any range. Examples of beta-emitters include Re-188, Re-187, Re-186, Ho-166, Y-90, Bi-212, Bi-213, and Sn-153. The beta-emitters may or may not also be gamma-emitters. One of ordinary skill in the art would be familiar with the use of beta-emitters in the treatment of hyperproliferative disease, such as cancer.

In further embodiments of the compositions of the present invention, the metal ion is a therapeutic metal ion that is not a beta emitter or a gamma emitter. For example, the therapeutic metal ion may be platinum, cobalt, copper, arsenic, selenium, calcium or thallium. Compositions including these therapeutic metal ions may be applied in methods directed to the treatment of diseases such as hyperproliferative diseases, cardiovascular disease, infections, and inflammation. Examples of hyperproliferative diseases include cancers. Methods of performing dual chemotherapy and radiation therapy that involve the compositions of the present invention are discussed in greater detail below.

D. TARGETING LIGANDS

A "targeting ligand" is defined herein to be a molecule or part of a molecule that binds with specificity to another molecule. One of ordinary skill in the art would be familiar with the numerous agents that can be employed as targeting ligands in the context of the present invention.

Examples of targeting ligands include disease cell cycle targeting compounds, angiogenesis targeting ligands, tumor apoptosis targeting ligands, disease receptor targeting ligands, gene expression markers, drug-based ligands, antimicrobials, tumor hypoxia targeting ligands, an antisense molecule, an agent that mimics glucose, amifostine, angiostatin, EGF receptor ligands, capecitabine, COX-2 inhibitors, deoxycytidine, fullerene, herceptin, human serum albumin, lactose, leuteinizing hormone, pyridoxal, quinazoline, thalidomide, transferrin, and trimethyl lysine.

In further embodiments of the present invention, the targeting ligand is an antibody. Any antibody is contemplated as a targeting ligand in the context of the present invention. For example, the antibody may be a monoclonal antibody. One of ordinary skill in the art would be familiar with monoclonal antibodies, methods of preparation of monoclonal antibodies, and methods of use of monoclonal antibodies as ligands. In certain embodiments of the present invention, the monoclonal antibody is an antibody directed against a tumor marker. In some embodiments, the monoclonal antibody is monoclonal antibody C225, monoclonal antibody CD31, or monoclonal antibody CD40.

A single targeting ligand, or more than one such targeting ligand, may be conjugated to a chelator of the present invention. In these embodiments, any number of targeting ligands may be conjugated to the chelators set forth herein. In certain embodiments, a conjugate of the present invention may comprise a single targeting ligand. In other embodiments, a conjugate may comprise only two targeting ligands. In further embodiments, a targeting ligand may comprise three or more targeting ligands. In any situation where a conjugate comprises two or more targeting ligands, the targeting ligands may be the same or different.

The targeting ligands can be bound to the chelator in any manner, including for example covalent bonds, ionic bonds and hydrogen bonds. For example, the targeting ligand may be bound to the chelator in an amide linkage, an ester linkage, or a carbon-carbon bond linkage of any length. If two or more targeting ligands are bound to a chelator, the modes of binding may be the same or different. In other embodiments, the linkage comprises a linker. Non-limiting examples of such linkers include peptides, glutamic acid, aspartic acid, bromo ethylacetate, ethylene diamine, lysine and any combination of one or more of these groups. One of ordinary skill in the art would be familiar with the chemistry of these agents, and methods to conjugate these agents as ligands to the chelators of the claimed invention. Methods of synthesis of the compounds of the present invention, including modes of conjugation, are discussed in detail below.

Information pertaining to targeting ligands and conjugation with compounds is provided in U.S. Pat. No. 6,692,724, U.S. patent application Ser. No. 09/599,152, U.S. patent application Ser. No. 10/627,763, U.S. patent application Ser. No. 10/672,142, U.S. patent application Ser. No. 10/703, 405, and U.S. patent application Ser. No. 10/732,919, each of which is herein specifically incorporated by reference in their entirety for this section of the specification and all other sections of the specification.

In some embodiments of the compositions of the present invention, the targeting ligand is a tissue-specific ligand, which is conjugated to the chelator. A "tissue-specific ligand" is defined herein to refer to a molecule or a part of a molecule that can bind or attach to one or more tissues. The binding may be by any mechanism of binding known to those of ordinary skill in the art. Examples include therapeutic agents, antimetabolites, apoptotic agents, bioreductive agents, signal transductive therapeutic agents, receptor responsive agents, or cell cycle specific agents. The tissue may be any type of tissue, such as a cell. For example, the cell may be the cell of a subject, such as a cancer cell. In certain embodiments, the tissue-targeting ligand is a tissue-targeting amino acid sequence that is conjugated to a chelator that is capable of binding to a metal ion.

Representative examples of targeting ligands are discussed below.

1. Drugs

In some embodiments of the compositions of the present invention, a targeting ligand is a drug, or "therapeutic ligand," which is defined herein to refer to any therapeutic agent. A "therapeutic agent" or "drug" is defined herein to include any compound or substance that can be administered to a subject, or contacted with a cell or tissue, for the purpose of treating a disease or disorder, or preventing a disease or disorder, or treating or preventing an alteration or disruption of a normal physiologic process. For example, the therapeutic ligand may be an anti-cancer moiety, such as a chemotherapeutic agent. In certain embodiments of the present invention, the therapeutic ligand is a therapeutic amino acid sequence that is conjugated to the therapeutic amino acid sequence. Such conjugates are discussed further in other parts of this specification.

a. Chemotherapeutic Agents

Examples of anti-cancer ligands include any chemotherapeutic agent known to those of ordinary skill in the art. Examples of such chemotherapeutic agents include, but are not limited to, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing. In certain particular embodiments, the anti-cancer ligand is methotrexate.

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaI1; dynemicin, including dynemicin A); bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY117018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor and a HER2 expression inhibitor; vaccines such as gene therapy vaccines and pharmaceutically acceptable salts, acids or derivatives of any of the above.

Additional examples of anti-cancer agents include those drugs of choice for cancer chemotherapy listed in Table 1:

TABLE 1

Drugs of Choice for Cancer Chemotherapy
The tables that follow list drugs used for treatment of cancer in the USA and Canada and their major adverse effects. The Drugs of Choice listing based on the opinions of Medical Letter consultants. Some drugs are listed for indications for which they have not been approved by the U.S. Food and Drug Administration. Anti-cancer drugs and their adverse effects follow. For purposes of the present invention, these lists are meant to be exemplary and not exhaustive.
DRUGS OF CHOICE

| Cancer | Drugs of Choice | Some alternatives |
|---|---|---|
| Adrenocortical** | Mitotane | Doxorubicin, streptozocin, etoposide |
|  | Cisplatin |  |
| Bladder* | Local: Instillation of BCG | Installation of mitomycin, doxorubicin or thiotape |
|  | Systemic: Methotrexate + vinblastine + doxorubicin + cisplatin (MVAC) | Pacitaxel, substitution of carboplatin for cisplatin in combinations |
|  | Cisplatin + Methotrexate + vinblastine (CMV) |  |
| Brain |  |  |
| Anaplastic astrocytoma* | Procarbazine + lomustine + vincristine | Carmustine, Cisplatin |
| Anaplastic oligodendro-Glioma* | Procarbazine + lomustine + vincristine | Carmustine, Cisplatin |
| Glioblastoma** | Carmustine or lomustine | Procarbazine, cisplatin |
| Medulloblastoma | Vincristine + carmustine ± mechlorethamine ± methotrexate | Etoposide |
|  | Mechlorethamine + vincristine + procarbazine + prednisone (MOPP) |  |
|  | Vincristine + cisplatin ± cyclophosphamide |  |
| Primary central nervous system lymphoma | Methotrexate (high dose Intravenous and/or Intrathecal) ± cytarabine (Intravenous and/or Intrathecal) |  |
|  | Cyclophosphamide + Doxorubicin + vincristine + prednisone (CHOP) |  |
| Breast | Adjuvant[1]: Cyclophosphamide + methotrexate + fluorouracil (CMF); Cyclophosphamide + Doxorubicin ± fluorouracil (AC or CAF); Tamoxifen |  |
|  | Metastatic: Cyclophosphamide + methotrexate + fluorouracil (CMF) or Cyclophosphamide + doxorubicin ± fluorouracil (AC or CAF) for receptor-negative and/or hormone-refractory; Tamoxifen for receptor-positive and/or hormone-sensitive[2] | Paclitaxel; thiotepa + Doxorubicin + vinblastine; mitomycin + vinblastine; mitomycin + methotrexate + mitoxantrone; fluorouracil by continuous infusion; Bone marrow transplant[3] |
| Cervix** | Cisplatin | Chlorambucil, vincristine, fluorouracil, Doxorubicin, methotrexate, altretamine |
|  | Ifosfamide with means |  |
|  | Bleomycin + ifosfamide with means + cisplatin |  |
| Choriocarcinoma | Methotrexate ± leucovorin | Methotrexate + dactinomycin + cyclophosphamide (MAC) Etoposide + methotrexate + dactinomycin + cyclophosphamide + vincristine |
|  | Dactinomycin |  |
| Colorectal* | Adjuvant colon[4]: Fluorouracil + levamisole; fluorouracil + leucovorin | Hepatic metastases: Intrahepatic-arterial floxuridine Mitomycin |
|  | Metastatic: fluorouracil + leucovorin |  |
| Embryonal rhabdomyosarcoma[5] | Vincristine + dactinomycin ± cyclophosphamide | Same + Doxorubicin |
|  | Vincristine + ifosfamide with means + etoposide |  |
| Endometrial** | Megastrol or another progestin | fluorouracil, tamoxifen, altretamine |
|  | Doxorubicin + cisplatin ± cyclophosphamide |  |
| Esophageal* | Cisplatin + fluorouracil | Doxorubicin, methotraxate, mitomycin |
| Ewing's sarcoma[5] | Cyclophosphamide (or ifosfamide with means) + Doxorubicin + vincristine (CAV) ± dactinomycin | CAV + etoposide |
| Gastric** | Fluorouracil ± leucovorin | Cisplatin, Doxorubicin, etoposide, methotrexate + leucovorin, mitomycin |

TABLE 1-continued

Drugs of Choice for Cancer Chemotherapy
The tables that follow list drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.

DRUGS OF CHOICE

| Cancer | Drugs of Choice | Some alternatives |
| --- | --- | --- |
| Head and neck squamous cell* | Cisplatin + fluorouracil Methotrexate | Bleomycin, carboplatin, paclitaxel |
| Islet cell** | Streptozocin + Doxorubicin | Streptozocin + fluorouracil; chlorozotocin[†]; octreotide |
| Kaposi's sarcoma* (Aids-related) | Etoposide or interferon alfa or vinblastine Doxorubicin + bleomycin + vincristine or vinblastine (ABV) | Vincristine, Doxorubicin, bleomycin |
| Leukemia | | |
| Acute lymphocytic leukemia (ALL)[6] | Induction: Vincristine + prednisone + asparaginase ± daunorubicin CNS prophylaxis: Intrathecal methotrexate ± systemic high-dose methotrexate with leucovorin ± Intrathecal cytarabine ± Intrathecal hydrocortisone Maintenance: Methotrexate + mercaptopurine Bone marrow transplant.[3] [7] | Induction: same ± high-dose methotrexate ± cytarabine; pegaspargase instead of asparaginese Teniposide or etoposide High-dose cytarabine<br><br>Maintenance: same + periodic vincristine + prednisone |
| Acute myeloid leukemia (AML)[8] | Induction: Cytarabine + either daunorubicin or idarubicin Post Induction: High-dose cytarabine ± other drugs such as etoposide Bone marrow transplant[3]. | Cytarabine + mitoxentrone High-dose cytarabine |
| Chronic lymphocytic leukemia (CLL) | Chlorambucil ± prednisone Fludarabin | Cladribine, cyclophosphamide, pentostatin, vincristine, Doxorubicin |
| Chronic myeloid leukemia (CML)[9] | | |
| Chronic phase | Bone marrow transplant[3] Interferon alfa Hydroxyurea | Busulfan |
| Accelerated[10] Blast crisis[11] | Bone marrow transplant[3] Lymphoid: Vincristine + prednisone + L-asparaginase + intrathecal methotrexate (± maintenance with methotrexate + 8-mercaptopurine) | Hydroxyures, busulfan Tretinoln[†] Amsecrine, [†]azacitidine Vincristine ± plicamycin |
| Hairy cell Leukemia | Pentostatin or cladribine | Interferon alfa, chlorambucil, fludarabin |
| Liver** | Doxorubicin Fluorouracil | Intrahepatic-arterial floxuridine or claplatin |
| Lung, small cell (cat cell) | Cisplatin + etoposide (PE) Cyclophosphamide + doxorubicin + vincristine (CAV) PE alternated with CAV Cyclophosphamide + etoposide + cisplatin (CEP)<br><br>Doxorubicin + cyclophosphamide + etoposide (ACE) | Ifosfamide with means + carboplatin + etoposide (ICE) Daily oral etoposide Etoposide + ifosfamide with means + claplatin (VIP Paclitaxel |
| Lung (non-small cell)** | Cisplatin + etoposide Cisplatin + Vinblastine ± mitomycin Cisplatin + vincristine | Cisplatin + fluorouracil + leucovorin Carboplatin + paclitaxel |
| Lymphomas | | |
| Hodgkin's[11] | Doxorubicin + bleomycin + vinblastine + dacarbazine (ABVD)<br><br>ABVD alternated with MOPP Mechlorethamine + vincristine + procarbazine (± prednisone) + doxorubicin + bleomycin + vinblastine (MOP[P]-ABV) | Mechlorethamine + vincristine + procarbazine + prednisone (MOPP) Chlorambusil + vinblastine + procarbazine + prednisone ± carmustine Etoposide + vinblastine + doxorubicin Bone marrow transplant[3] |

TABLE 1-continued

Drugs of Choice for Cancer Chemotherapy
The tables that follow list drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.

DRUGS OF CHOICE

| Cancer | Drugs of Choice | Some alternatives |
| --- | --- | --- |
| Non-Hodgkin's | | |
| Burkitt's lymphoma | Cyclophosphamide + vincristine + methotrexate<br>Cyclophosphamide + high-dose cytarabine ± methotrexate with leutovorin<br>Intrathecal methotrexate or cytarabine | Ifosfamide with means<br>Cyclophosphamide + doxorubicin + vincristine + prednisone (CHOP) |
| Diffuse large-cell lymphoma | Cyclophosphamide + doxorubicin + vincristine + prednisone (CHOP) | Dexamethasone sometimes substituted for prednisone<br>Other combination regimens, which may include methotrexate, etoposide, cytarabine, bleomycin, procarbazine, ifosfamide and mitoxantrone<br>Bone marrow transplant[3] |
| Follicular lymphoma | Cyclophosphamide or chlorambusil | Same ± vincristine and prednisone, ± etoposide<br>Interferon alfa, cladribine, fludarabin<br>Bone marrow transplant[3]<br>Cyclophosphamide + doxorubicin + vincristine + prednisone (CHOP) |
| Melanoma** | Interferon Alfa<br>Dacarbazine | Carmustine, lomustine, cisplatin<br>Dacarbazine + clapletin + carmustine + tamoxifen<br>Aldesleukin |
| Mycosis fungoides* | PUVA (psoralen + ultraviolet A)<br>Mechlorethamine (topical)<br>Interferon alfa<br>Electron beam radiotherapy<br>Methotrexate | Isotretinoin, topical carmustine, pentosistin, fludarabin, cladribine, photopheresis (extra-corporeal photochemitherapy), chemotherapy as in non-Hodgkin's lymphoma |
| Myloma* | Melphalan (or cyclophosphamide) + prednisone<br>Melphalan + carmustine + cyclophosphamide + prednisone + vincristine<br>Dexamethasone + doxorubicin + vincristine (VAD)<br>Vincristine + carmustine + doxorubicin + prednisone (VBAP) | Interferon alfa<br>Bone marrow transplant[3]<br>High-dose dexamethasone |
| Neuroblastoma* | Doxorubicin + cyclophosphamide + cisplatin + teniposide or etoposide<br>doxorubicin + cyclophosphamide<br>Claplatin + cyclophosphamide | Carboplatin, etoposide<br>Bone marrow transplant[3] |
| Osteogenic sarcoma[5] | Doxorubicin + cisplatin ± etoposide ± ifosfamide | Ifosfamide with means, etoposide, carboplatin, high-dose methotrexate with leucovorin<br>Cyclophosphamide + etoposide |
| Ovary | Cisplatin (or carboplatin) + paclitaxel<br>Cisplatin (or carboplatin) + cyclophosphamide (CP) ± doxorubicin (CAP) | Ifosfamide with means, paclitaxel, tamoxifen, melphalan, altretamine |
| Pancreatic** | Fluorouracil ± leucovorin | |
| Prostate | Leuprolide + flutamide | Estramustine + vinblastine, aminoglutethimide + hydrocortisone, estramustine + etoposide, diethylstilbestrol, nilutamide |

TABLE 1-continued

Drugs of Choice for Cancer Chemotherapy
The tables that follow list drugs used for treatment of cancer in the USA and
Canada and their major adverse effects. The Drugs of Choice listing based on the
opinions of Medical Letter consultants. Some drugs are listed for indications for which
they have not been approved by the U.S. Food and Drug Administration. Anti-cancer
drugs and their adverse effects follow. For purposes of the present invention, these lists
are meant to be exemplary and not exhaustive.
DRUGS OF CHOICE

| Cancer | Drugs of Choice | Some alternatives |
| --- | --- | --- |
| Renal** | Aldesleukin<br>Inteferon alfa | Vinblastine, floxuridine |
| Retinoblastoma[5]* | Doxorubicin + cyclophosphamide + cisplatin +<br>etoposide + vincristine | Carboplatin, etoposide,<br>Ifosfamide with means |
| Sarcomas, soft tissue, adult* | Doxorubicin + dacarbazine +<br>cyclophosphamide + Ifosfamide with means | Mitornyeln + doxorubicin +<br>cisplatin<br>Vincristine, etoposide |
| Testicular | Cisplatin + etoposide + bleomycin (PEB) | Vinblastine (or etoposide) +<br>Ifosfamide with means +<br>cisplatin (VIP)<br>Bone marrow transplant[3] |
| Wilms' tumor[5] | Dactinomycin + vincristine + doxorubicin +<br>cyclophosphamide | Ifosfamide with means,<br>etoposide, carboplatin |

*Chemotherapy has only moderate activity.
**Chemotherapy has only minor activity.
[1]Tamoxifen with or without chemotherapy is generally recommended for postmenopausal estrogen-receptor-positive, mode-positive patients and chemotherapy with or without tamoxifen for premenopausal mode-positive patients. Adjuvant treatment with chemotherapy and/or tamoxifen is recommended for mode-negative patients with larger tumors or other adverse prognostic indicators.
[2]Megastrol and other hormonal agents may be effective in some patients with tamoxifen fails.
[3]After high-dose chemotherapy (Medical Letter, 34: 79, 1982).
[4]For rectal cancer, postoperative adjuvant treatment with fluorouracil plus radiation, preceded and followed by treatment with fluorouracil alone.
[5]Drugs have major activity only when combined with surgical resection, radiotherapy or both.
[†]Available in the USA only for investigational use.
[6]High-risk patients (e.g., high counts, cytogenetic abnormalities, adults) may require additional drugs for induction, maintenance and "intensificiation" (use of additional drugs after achievement of remission). Additional drugs include cyclophosphamida, mitoxantrone and thloguanine. The results of one large controlled trial in the United Kingdom suggest that intensificiation may improve survival in all children with ALL (Chasselle et al, 1995).
[7]Patients with a poor prognosis initially or those who relapse after remission.
[8]Some patients with acute promyelocytic leukemia have had complete responses to tratinoin. Such treatment can cause a toxic syndrome characterized primarily by fever and respiratory distress (Warrell, Jr et al, 1993).
[9]Allogeneic HLA-identical sibling bone marrow transplantation can cure 40% to 70% of patients with CML in chronic phase, 18% to 28% of patients with accelerated phase CML, and <15% patients in blast crisis. Disease-free survival after bone marrow transplantations adversely influenced by age >50 years, duration of disease >3 years from diagnosis, and use of one-antigen-mismatched or matched-unrelated donor marrow. Interferon also may be curative in patients with chronic phase CML who achieve a complete cytogenetic response (about 10%); it is the treatment of choice for patents >80 years old with newly diagnosed chronic phase CML and for all patients who are not candidates for an allgensic bone marrow transplant. Chemotherapy alone is palliative.
[10]If a second chronic phase is achieved with any of these combinations, allogeneic bone marrow transplant should be considered. Bone marrow transplant in second chronic phase may be curative for 30% to 35% of patients with CML.
[11]Limited-stage Hodgkin's disease (stages 1 and 2) is curable by radiotherapy. Disseminated disease (stages 3b and 4) require chemotherapy. Some intermediate stages and selected clinical situations may benefit from both.
+ Available in the USA only for investigational use.

b. Cardiovascular Drugs

A "cardiovascular drug" is defined herein to refer to any therapeutic agent that can be applied in the treatment or prevention of a disease of the heart and/or blood vessels.

In certain embodiments, the cardiovascular drug is an agent that lowers the concentration of one of more blood lipids and/or lipoproteins, known herein as an "antihyperlipoproteinemic," which can be applied in the treatment of athersclerosis and thickenings or blockages of vascular tissues. Examples include an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof. Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simflbrate and theofibrate. Non-limiting examples of resins/bile acid sequesterants include cholestyramine (cholybar, questran), colestipol (colestid) and polidexide. Non-limiting examples of HMG CoA reductase inhibitors include lovastatin (mevacor), pravastatin (pravochol) or simvastatin (zocor). Non-limiting examples of nicotinic acid derivatives include nicotinate, acepimox, niceritrol, nicoclonate, nicomol and oxiniacic acid. Non-limiting examples of thyroid hormones and analogs thereof include etoroxate, thyropropic acid and thyroxine. Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

Non-limiting examples of an antiarteriosclerotic include pyridinol carbamate.

In certain embodiments, the cardiovascular drug is an agent that aids in the removal or prevention of blood clots. Non-limiting examples of antithrombotic and/or fibrinolytic agents include anticoagulants, anticoagulant antagonists, antiplatelet agents, thrombolytic agents, thrombolytic agent antagonists or combinations thereof. Examples of antithrombotic agents include aspirin and wafarin (coumadin. Examples of anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin. Non-limiting examples of antiplatelet agents include aspirin, a dextran, dipyridamole (persantin), heparin, sulfinpyranone (anturane) and ticlopidine (ticlid). Non-limiting examples of thrombolytic agents include tissue plaminogen activator (activase), plasmin, pro-urokinase, urokinase (abbokinase) streptokinase (streptase), anistreplase/APSAC (eminase).

In some embodiments, the cardiovascular drug is a blood coagulant. Non-limiting examples of a blood coagulation promoting agent include thrombolytic agent antagonists and anticoagulant antagonists. Non-limiting examples of anticoagulant antagonists include protamine and vitamin K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

The cardiovascular drug may be an antiarrythmic agent. Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents. Non-limiting examples of sodium channel blockers include Class IA, Class IB and Class IC antiarrhythmic agents. Non-limiting examples of Class IA antiarrythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor). Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol. Non-limiting examples of an agent that prolong repolarization, also known as a Class III antiarrhythmic agent, include amiodarone (cordarone) and sotalol (betapace). Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist. Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Other examples of cardiovascular drugs include antihypertensive agents. Non-limiting examples of antihypertensive agents include sympatholytic, alpha/beta blockers, alpha blockers, anti-angiotensin II agents, beta blockers, calcium channel blockers, vasodilators and miscellaneous antihypertensives. Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an alpha and beta adrenergic antagonist. Non-limiting examples of an alpha/beta blocker comprise labetalol (normodyne, trandate). Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan. Non-limiting examples of a sympatholytic include a centrally acting sympatholytic or a peripherally acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin). In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, troInitrate phosphate and visnadine. In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

Other examples of cardiovascular drugs include vasopressors. Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Other examples of cardiovascular drugs include agents that can be applied in the treatment or prevention of congestive heart failure. Non-limiting examples of agents for the treatment of congestive heart failure include anti-angiotension II agents, afterload-preload reduction treatment, diuretics and inotropic agents. Examples of afterload-preload reduction agents include hydralazine (apresoline) and isosorbide dinitrate (isordil, sorbitrate). Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea. Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol. In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor). Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

2. Disease Cell Cycle Targeting Compounds

Disease cell cycle targeting compounds refers to compounds that target agents that are upregulated in proliferating cells. Compounds used for this purpose can be used to measure various parameters in cells, such as tumor cell DNA content.

Many of these agents are nucleoside analogues. For example, pyrimidine nucleoside (e.g., 2'-fluoro-2'-deoxy-5-iodo-1-β-D-arabinofuranosyluracil [FIAU], 2'-fluoro-2'-deoxy-5-iodo-1-β-D-ribofuranosyl-uracil [FIRU], 2'-fluoro-2'-5-methyl-1-β-D-arabinofuranosyluracil [FMAU], 2'-fluoro-2'-deoxy-5-iodovinyl-1-β-D-ribofuranosyluracil [IVFRU]) and acycloguanosine: 9-[(2-hydroxy-1-(hydroxymethyl)ethoxy)methyl]guanine (GCV) and 9-[4-hydroxy-3-(hydroxy-methyl)butyl]guanine (PCV) (Tjuvajev et al., 2002; Gambhir et al., 1998; Gambhir et al., 1999) and other $^{18}$F-labeled acycloguanosine analogs, such as 8-fluoro-9-[(2-hydroxy-1-(hydroxymethyl)ethoxy)methyl]guanine (FGCV) (Gambhir et al., 1999; Namavari et al., 2000), 8-fluoro-9-[4-hydroxy-3-(hydroxymethyl)butyl]guanine (FPCV) (Gambhir et al., 2000; Iyer et al., 2001), 9-[3-fluoro-1-hydroxy-2-propoxy methyl]guanine (FHPG) (Alauddin et al., 1996; Alauddin et al., 1999), and 9-[4-fluoro-3-(hydroxymethyl)butyl]guanine (FHBG) (Alauddin and Conti, 1998; Yaghoubi et al., 2001) have been developed as reporter substrates for imaging wild-type and mutant (Gambhir et al., 2000) HSV1-tk expression. One or ordinary skill in the art would be familiar with these and other agents that are used for disease cell cycle targeting.

3. Angiogenesis Targeting Ligands

"Angiogenesis targeting ligands" refers to agents that can bind to neovascularization or revascularization of tissue. For example, the neovascularization of tumor cells or revascularization of myocardium tissue. Agents that are used for this purpose are known to those of ordinary skill in the art for use in performing various measurements, including measurement of the size of a tumor vascular bed and measurement of tumor volume. Some of these agents bind to the vascular wall. One of ordinary skill in the art would be familiar with the agents that are available for use for this purpose.

Throughout this application, "angiogenesis targeting" refers to the use of an agent to bind to neovascular tissue. Some examples of agents that are used for this purpose are known to those of ordinary skill in the art for use in performing various tumor measurements, including measurement of the size of a tumor vascular bed, and measurement of tumor volume. Some of these agents bind to the vascular wall. One of ordinary skill in the art would be familiar with the agents that are available for use for this purpose. A tumor angiogenesis targeting ligand is a ligand that is used for the purpose of tumor angiogenesis targeting as defined above. Examples of angiogenesis targeting ligands include COX-2 inhibitors, anti-EGF receptor ligands, herceptin, angiostatin, C225 and thalidomide. COX-2 inhibitors include, for example, celecoxib, rofecoxib, etoricoxib and analogs of these agents.

4. Tumor Apoptosis Targeting Ligands

"Tumor apoptosis targeting" refers to use of an agent to bind to a cell that is undergoing apoptosis or at risk of undergoing apoptosis. These agents are generally used to provide an indicator of the extent or risk of apoptosis, or programmed cell death, in a population of cells, such as a tumor and cardiac tissue. One of ordinary skill in the art would be familiar with agents that are used for this purpose. A "tumor apoptosis targeting ligand" is a ligand that is capable of performing "tumor apoptosis targeting" as defined in this paragraph. The targeting ligand of the present invention may include TRAIL (TNF-related apoptosis inducing ligand) monoclonal antibody. TRAIL is a member of the tumor necrosis factor ligand family that rapidly induces apoptosis in a variety of transformed cell lines. The targeting ligand of the present invention may also comprise a substrate of caspase-3, such as peptide or chelator that includes the 4 amino acid sequence aspartic acid-glutamic acid-valine-aspartic acid. caspase-3 substrate (for example, a peptide or chelator that includes the amino acid sequence aspartic acid-glutamic acid-valine-aspartic acid), and any member of the Bcl family. Examples of Bcl family members include, for example, Bax, Bcl-xL, Bid, Bad, Bak and Bcl-2. One of ordinary skill in the art would be familiar with the Bcl family, and their respective substrates.

Apoptosis suppressors are targets for drug discovery, with the idea of abrogating their cytoprotective functions and restoring apoptosis sensitivity to tumor cells (Reed, 2003).

5. Disease Receptor Targeting Ligands

In "disease receptor targeting," certain agents are exploited for their ability to bind to certain cellular receptors that are overexpressed in disease states, such as cancer, neurological diseases and cardiovascular diseases. Examples of such receptors which are targeted include estrogen receptors, androgen receptors, pituitary receptors, transferrin receptors and progesterone receptors. Examples of agents that can be applied in disease-receptor targeting include androgen, estrogen, somatostatin, progesterone, transferrin, luteinizing hormone and luteinizing hormone antibody.

The radiolabeled ligands, such as pentetreotide, octreotide, transferrin and pituitary peptide, bind to cell receptors, some of which are overexpressed on certain cells. Since these ligands are not immunogenic and are cleared quickly from the plasma, receptor imaging would seem to be more promising compared to antibody imaging.

The folate receptor is included herein as another example of a disease receptor. Folate receptors (FRs) are overexposed on many neoplastic cell types (e.g., lung, breast, ovarian, cervical, colorectal, nasopharyngeal, renal adenocarcinomas, malignant melanoma and ependymomas), but primarily expressed only several normal differentiated tissues (e.g., choroid plexus, placenta, thyroid and kidney) (Weitman et al., 1992a; Campbell et al., 1991; Weitman et al., 1992b; Holm et al., 1994; Ross et al., 1994; Franklin et al., 1994; Weitman et al., 1994). FRs have been used to deliver folate-conjugated protein toxins, drug/antisense oligonucleotides and liposomes into tumor cells overexpressing the folate receptors (Ginobbi et al., 1997; Leamon and Low, 1991; Leamon and Low, 1992; Leamon et al., 1993; Lee and Low, 1994). Furthermore, bispecific antibodies that contain anti-FR antibodies linked to anti-T cell receptor antibodies have been used to target T cells to FR-positive tumor cells and are currently in clinical trials for ovarian carcinomas (Canevari et al., 1993; Bolhuis et al., 1992; Patrick et al., 1997; Coney et al., 1994; Kranz et al., 1995).

Examples of folate receptor targeting ligands include folic acid and analogs of folic acid. Preferred folate receptor targeting ligands include folate, methotrexate and tomudex. Folic acid as well as antifolates such as methotrexate enter into cells via high affinity folate receptors (glycosylphosphatidylinositol-linked membrane folate-binding protein) in addition to classical reduced-folate carrier system (Westerhof et al., 1991; On et al., 1995; Hsueh and Dolnick, 1993).

6. Cardiac Ischemia Markers

In some embodiments, the targeting ligand is a cardiac ischemia marker. A cardiac ischemia marker is a ligand that is relatively selective for ischemic cardiac tissue. Non-limiting examples of cardiac ischemia markers include interleukin-6, tumor necrosis factor alpha, matrix metalloproteinase 9, myeloperoxidase, intercellular and vascular adhesion molecules, soluble CD40 ligand, placenta growth factor, high sensitivity C-reactive protein (hs-CRP), ischemia modified albumin (IMA), free fatty acids, and choline.

7. Viability Cardiac Tissue Markers

In some embodiments, the targeting ligand is a viability cardiac tissue marker. A viability cardiac tissue marker refers to a ligand that is relatively selective for viable cardiac tissue compared to nonviable cardiac tissue. Non-limiting examples of cardiac viability tissue markers include those selected from the group consisting of phospholipase C, myosin light-chain phosphatase, nitric oxide, prostacyclin, endothelin, thromboxane, L-arginine and L-citrulline.

8. Congestive Heart Failure Markers

In some embodiments, the targeting ligand is a congestive heart failure marker. A congestive heart failure marker is a ligand that is relatively selective for cardiac tissue of a heart in congestive heart failure compared to normal healthy heart tissue. Non-limiting examples of congestive heart failure markers include those selected from the group consisting of interleukin-1, cardiotrophin-1, insulin-like growth factor, epidermal growth factor, tyrosine kinase receptor and angiotensin II.

9. Rest/Stress Cardiac Tissue Markers

In some embodiments, the targeting ligand is a rest/stress cardiac tissue marker. A rest/stress cardiac tissue marker is a ligand that is relatively selective for cardiac tissue that is stressed compared to non-stressed (at rest) cardiac tissue, or vice versa. Non-limiting examples of rest/stress cardiac tissue markers include those selected from the group consisting of mitogen-activated protein kinase, cyclic adenosine monophosphate, phospholipase C, phosphatidylinositol bisphosphate, isositol trisphosphate, diacylglycerol and tyrosine kinases.

10. Drug Assessment

Certain drug-based ligands can be applied in measuring the pharmacological response of a subject to a drug. A wide range of parameters can be measured in determining the response of a subject to administration of a drug. One of ordinary skill in the art would be familiar with the types of responses that can be measured. These responses depend in part upon various factors, including the particular drug that is being evaluated, the particular disease or condition for which the subject is being treated, and characteristics of the subject. Examples of drug-based ligands include carnitine, puromycin, verapamil, digoxin, prazosin, quinidine, disopyramide, theophylline, protease inhibitors nidepidine, diltiazem, flecamide, amiodarone, sotalol, adenosine, dopamine dobutamine, inaminone, milrinone, spironolactone, prazosin, aspirin and warfarin.

11. Antimicrobials

Any antimicrobial is contemplated for inclusion as a targeting ligand. Preferred antimicrobials include ampicillin, amoxicillin, penicillin, clindamycin, gentamycin, kanamycin, neomycin, natamycin, nafcillin, rifampin, tetracycline, vancomycin, bleomycin, doxycyclin, amikacin, netilmicin, streptomycin, tobramycin, loracarbef, ertapenem, imipenem, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, azithromycin, clarithromycin, dirithromycin, erythromycin, roxithromycin, troleandomycin, aztreonam, azlocillin, carbenicillin, cloxacillin, dicloxacillin, flucloxacillin, mezlocillin, piperacillin, ticarcillin, bacitracin, colistin, polymyxin b, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole, demeclocycline, minocycline, oxytetracycline, arsphenamine, chloramphenicol, ethambutol, fosfomycin, furazolidone, isoniazid, linezolid, metronidazole, mupirocin, nitrofurantoin, platensimycin, pyrazinamide, quinupristin, dalfopristin, spectinomycin, and telithromycin.

Antifungals include natamycin, rimocidin, filipin, nystatin, amphotericin B, miconazole, ketoconazole, clotrimazole, econazole, bifonazole, butocanazole, finticonazole, isoconazole, oxiconazole, sertaconazole, sulconazole, tioconazole, fluconazole, itraconazole, ravuconazole, posaconazole, vorconazole, terconazole, terbinafine, amorolfine, naftifine, butenafine, anidulafungin, caspofungin, micafungin, ciclopirox, flucytosine, griseofulvin, gentian violet, haloprogin, tolnaftate, undecyclenic acid, amantadine, polymyxin, acyclovir and ganciclovir for fungi. One of ordinary skill in the art would be familiar with the various agents that are considered to be antimicrobials.

12. Agents that Mimic Glucose

Agents that mimic glucose are also contemplated for inclusion as targeting ligands. Such agents can also be considered "glucose analogs" or "glucose derivatives."

Glucose is utilized by living organisms through the glycolysis pathway. Compounds such as neomycin, kanamycin, gentamycin, amikacin, tobramycin, netilmicin, ribostamycin, sisomicin, micromicin, lividomycin, dibekacin, isepamicin, and astromicin belong to a group called aminoglycosides.

In terms of structure, agents that mimic glucose typically have a glucose ring structure. Exceptions exist, however, such as puromycin, which has a pentose ring structure, but which can still be considered an agent that mimics glucose.

In terms of function, aminoglycosides are used as antibiotics that block the glycolysis pathway by their property of being structurally similar to glucose and thus, they are functionally considered as agents that mimic glucose. When these aminoglycosides are used in imaging studies, there are no detectable pharmacological effects.

The word "mimic", as defined by the American Heritage Dictionary fourth edition, means "to resemble closely or simulate." Aminoglycosides are functionally utilized through the glycolytic pathway by virtue of their structural similarity to glucose and block the glycolysis pathway. Hence, aminoglycosides are considered to mimic or simulate glucose in structural and functional manner.

Non-limiting examples of chemical structures with their PubChem Database (NCBI) identifier CID number are as follows: Amikacin CID 37768; Aminoglycoside CID 191574; Astromicin CID 65345; Deoxy-glucose CID 439268; D-glucosamine CID 441477; Dibekacin CID 3021; Gentamicin CID 3467; Glucose CID 5793; Isepamicin CID 456297; Kanamycin CID 5460349; Lividomycin CID 72394; Micromicin CID 107677; Neomycin CID 504578; Netilmycin CID 441306; Puromycin CID 439530; Ribostamycin CID 33042; Sisomicin CID 36119; and Tobramycin CID 36294.

References which describe the glycolysis blocking by aminoglycosides include, for example, Tachibana et al., 1976; Borodina et al., 2005; Murakami et al., 1996; Hoelscher et al., 2000; Yang et al., 2004; Michalik et al., 1989; Murakami et al., 1997; Diamond et al., 1978; Hostetler and Hall, 1982; Benveniste and Davies, 1973; Hu, 1998; Yanai et al., 2006; Myszka et al., 2003; Nakae and Nakae, 1982; Ozmen et al., 2005; and Tod et al., 2000.

Preferred agents that mimic glucose, or sugars, include neomycin, kanamycin, gentamycin, paromycin, amikacin, tobramycin, netilmicin, ribostamycin, sisomicin, micromicin, lividomycin, dibekacin, isepamicin, astromicin, and aminoglycosides glucose and glucosamine.

13. Hypoxia Targeting Ligands

In some embodiments of the present invention, the targeting ligand is a tumor hypoxia targeting ligand. For example, tumor cells are more sensitive to conventional radiation in the presence of oxygen than in its absence; even a small percentage of hypoxic cells within a tumor could limit the response to radiation (Hall, 1988; Bush et al., 1978; Gray et al., 1958). Hypoxic radioresistance has been demonstrated in many animal tumors but only in few tumor types in humans (Dische, 1991; Gatenby et al., 1988; Nordsmark et al., 1996). The occurrence of hypoxia in human tumors, in most cases, has been inferred from histology findings and from animal tumor studies. In vivo demonstration of hypoxia requires tissue measurements with oxygen electrodes and the invasiveness of these techniques has limited their clinical application.

Misonidazole, an example of a tumor hypoxia targeting ligand, is a hypoxic cell sensitizer, and labeling MISO with different radioisotopes (e.g., $^{18}$F, $^{123}$I, $^{99m}$Tc) may be useful for differentiating a hypoxic but metabolically active tumor from a well-oxygenated active tumor by PET or planar scintigraphy. [$^{18}$F]Fluoromisonidazole (FMISO) has been used with PET to evaluate tumors hypoxia. Recent studies have shown that PET, with its ability to monitor cell oxygen content through [$^{18}$F]FMISO, has a high potential to predict tumor response to radiation (Koh et al., 1992; Valk et al., 1992; Martin et al., 1989; Rasey et al., 1989; Rasey et al., 1990; Yang et al., 1995). PET gives higher resolution without collimation, however, the cost of using PET isotopes in a clinical setting is prohibitive.

14. Antisense Molecules

Antisense molecules interact with complementary strands of nucleic acids, modifying expression of genes.

Some regions within a double strand of DNA code for genes, which are usually instructions specifying the order of amino acids in a protein along with regulatory sequences, splicing sites, noncoding introns and other complicating details. For a cell to use this information, one strand of the DNA serves as a template for the synthesis of a complementary strand of RNA. The template DNA strand is called the antisense strand and the RNA is said to be sense (the complement of antisense). Because the DNA is double-stranded, the strand complementary to the antisense strand is also called sense and has the same base sequence as the mRNA (though T bases in DNA are substituted with U bases in RNA). For example:

DNA strand 1: sense strand
DNA strand 2: antisense strand (copied to)→RNA strand (sense).

Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense. Double stranded RNA acts as enzyme-dependent antisense through the RNAi/siRNA pathway, involving target mRNA recognition through sense-antisense strand pairing followed by target mRNA degradation by the RNA-induced silencing complex (RISC). Steric blocking antisense (RNase-H independent antisense) interferes with gene expression or other mRNA-dependent cellular processes by binding to a target sequence of mRNA and getting in the way of other processes. Steric blocking antisense includes 2'-O alkyl (usually in chimeras with RNase-H dependent antisense), peptide nucleic acid (PNA), locked nucleic acid (LNA) and Morpholino antisense. Cells can produce antisense RNA molecules naturally, which interact with complementary mRNA molecules and inhibit their expression.

Antisense nucleic acid molecules have been used experimentally to bind to mRNA and prevent expression of specific genes. Antisense therapies are also in development; the FDA has approved a phosphorothioate antisense oligo, fomivirsen (Vitravene), for human therapeutic use.

15. Imaging Moieties

In certain embodiments of the compositions of the present invention, the targeting ligand is an imaging moiety. As defined herein, an "imaging moiety" is a part of a molecule that is a agent or compound that can be administered to a subject, contacted with a tissue, or applied to a cell for the purpose of facilitating visualization of particular characteristics or aspects of the subject, tissue, or cell through the use of an imaging modality. Imaging modalities are discussed in greater detail below. Any imaging agent known to those of ordinary skill in the art is contemplated as an imaging moiety of the present invention. Thus, for example, in certain embodiments of compositions of the present invention, the compositions can be applied in multimodality imaging techniques. Dual imaging and multimodality imaging are discussed in greater detail in the specification below.

In certain embodiments, the imaging moiety is a contrast media. Examples include CT contrast media, MRI contrast media, optical contrast media, ultrasound contrast media, or any other contrast media to be used in any other form of imaging modality known to those of ordinary skill in the art. Examples include diatrizoate (a CT contrast agent), a gadolinium chelate (an MRI contrast agent) and sodium fluorescein (an optical contrast media). Additional examples of contrast media are discussed in greater detail in the specification below. One of ordinary skill in the art would be familiar with the wide range of types of imaging agents that can be employed as imaging moieties in the chelators of the present invention.

E. METHODS OF SYNTHESIS

1. Source of Reagents for the Compositions of the Present Invention

Reagents for preparation of the compositions of the present invention can be obtained from any source. A wide range of sources are known to those of ordinary skill in the art. For example, the reagents can be obtained from commercial sources such as Sigma-Aldrich Chemical Company (Milwaukee, Wis.), from chemical synthesis, or from natural sources. For example, one vendor of radionuclides is Cambridge Isotope Laboratories (Andover, Mass.). The reagents may be isolated and purified using any technique known to those of ordinary skill in the art, as described herein. The free unbound metal ions can be removed with, for example, ion-exchange resin or by adding a transchelator (e.g., glucoheptonate, gluconate, glucarate, or acetylacetonate).

2. Use of an Intermediate Product as the Active Pharmaceutical Ingredient (API)

Disulfide formation and nucleophilic attack of the anomeric center in the glucosamine moiety of certain compounds of the present invention can be problematic. For example, these unwanted reactions may occur at the thiol groups and/or the amino groups in EC-glucosamine (EC-G): these are the major side reactions that may cause the instability of EC-G. Furthermore, the typically low yield of the deprotection step with Na/NH$_3$ to get the primary product of EC-G may yield low purity (see FIGS. 1 and 13). Accordingly, it may be desirable to utilize intermediates of syntheses of the present invention as active pharmaceutical ingredients (APIs). For example, EC-G analogs such as those shown below, which are intermediate products in certain preparations may be used as APIs. These analogs, in certain embodiments, may yield high purity in the scale up process.

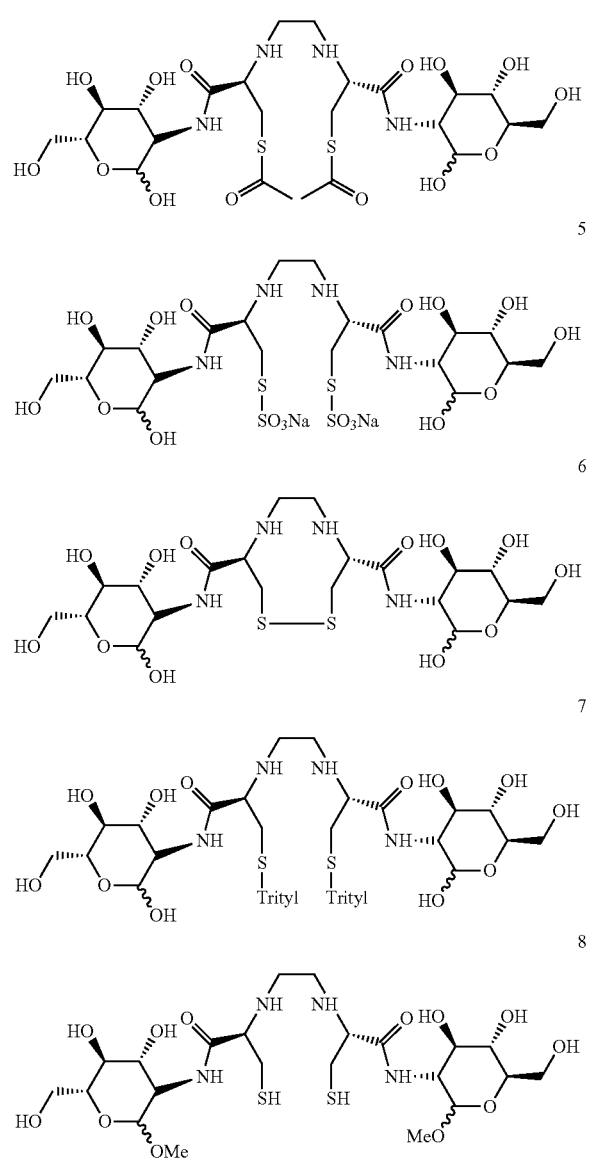

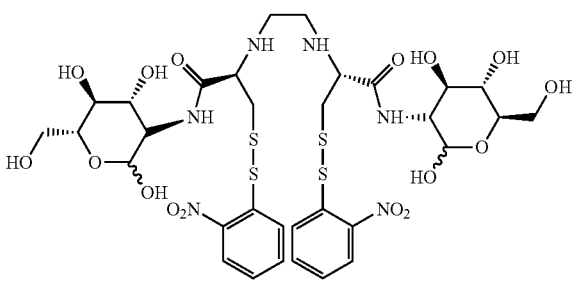

3. Purification Procedures and Determinations of Purity

As mentioned above, persons of ordinary skill in the art will be familiar with methods of purifying compounds of the present invention. As used herein, "purification" refers to any measurable increase in purity relative to the purity of the material before purification. Purification of every compound of the present invention is generally possible, including the purification of intermediates as well as purification of the final products. The purification step is not always included in the general methodologies explained below, but one of ordinary skill in the art will understand that compounds can generally be purified at any step. Examples of purification methods include gel filtration, size exclusion chromatography (also called gel filtration chromatography, gel permeation chromatography or molecular exclusion), dialysis, distillation, recrystallization, sublimation, derivatization, electrophoresis, silica gel column chromatography and high-performance liquid chromatography (HPLC), including normal-phase HPLC and reverse-phase HPLC. In certain embodiments, size exclusion chromatography and/or dialysis are specifically excluded as forms of purification of compounds of the present invention. Purification of compounds via silica gel column chromatography or HPLC, for example, offer the benefit of yielding desired compounds in very high purity, often higher than when compounds are purified via other methods. Radiochemical purity of compounds of the present invention can also be determined. Methods of determining radiochemical purity are well-known in the art and include chromatographic methods in conjunction with radioactivity detection methods (e.g., autoradiography analyses). Examples of comparisons of purity of compounds made via organic and wet methodologies and purified by varying methods are provided below.

Methods of determining the purity of compounds are well known to those of skill in the art and include, in non-limiting examples, autoradiography, mass spectroscopy, melting point determination, ultra violet analysis, colorimetric analysis, (HPLC), thin-layer chromatography and nuclear magnetic resonance (NMR) analysis (including, but not limited to, 1H and 13C NMR). In some embodiments, a colorimetric method could be used to titrate the purity of a chelator or chelator-targeting ligand conjugate. For instance, generation of a thiol-benzyl adduct (that is, a thiol functional group protected by a benzyl group) or the performance of an oxidation reaction by using iodine could be used to determine the purity of chelator or chelator-targeting ligand conjugate. In one embodiment, the purity of an unknown compound may be determined by comparing it to a compound of known purity: this comparison may be in the form of a ratio whose measurement describes the purity of the unknown. Software available on varying instruments (e.g., spectrophotometers, HPLCs, NMRs) can aid one of skill in the art in making these determinations, as well as other means known to those of skill in the art.

The following non-limiting parameters may be used, in certain embodiments, to determine the purity of compounds of the present invention:

Column: Primesep100, 4.6×150 mm, 5 µm, ambient temperature

Mobile phase (A): $H_2O$ with 0.025% TFA

Mobile phase (B): acetonitrile with 0.025% TFA

Isocratic run: A/B (50/50) at 1.0 ml/min

Detection: ELSD, SEDEX75, 50 C, 4.5 bar

In certain embodiments of the present invention, purification of a compound does not remove all impurities. In some embodiments, such impurities can be identified.

4. Obtaining a Chelator

Methods of preparing and obtaining chelators are well known to those of skill in the art. For example, chelators may be obtained from commercial sources, chemical synthesis, or natural sources.

In one embodiment, the chelator may comprises ethylenedicysteine (EC). The preparation of ethylenedicysteine (EC) is described in U.S. Pat. No. 6,692,724. Briefly, EC may be prepared in a two-step synthesis according to the previously described methods (Ratner and Clarke, 1937; Blondeau et al., 1967; each incorporated herein by reference). The precursor, L-thiazolidine-4-carboxylic acid, was synthesized and then EC was then prepared. It is often also important to include an antioxidant in the composition to prevent oxidation of the ethylenedicysteine. The preferred antioxidant for use in conjunction with the present invention is vitamin C (ascorbic acid). However, it is contemplated that other antioxidants, such as tocopherol, pyridoxine, thiamine, or rutin may also be useful.

Chelators may also comprise amino acids joined together by spacers. Such a spacer may comprise, as described above, an alkyl spacer such as ethylene.

Amide bonds may also join one or more amino acids together to form a chelator. Examples of synthetic methods for the preparation of such chelators include solid-phase synthesis and solution-phase synthesis. Such methods are described, for example, in Bodansky, 1993 and Grant, 1992.

5. Organic Synthesis of Chelator-Targeting Ligand Conjugates

In a preferred embodiment, the present invention further provides a method of organically synthesizing chelator-targeting ligand conjugates. The method includes obtaining, for example, a chelator such as ethylenedicysteine (EC) as described above and admixing the EC with a thiol protecting group in an organic medium in order to protect both free thiols, resulting in an S—S'-bis-protected-EC, which is then admixed with an amino protecting group in an organic/aqueous medium in order to protect both free amines, resulting in an S—S'-bis-protected-N,N'-bis-protected-EC. Thiol groups are more reactive than nitrogen groups; thus, thiol groups are typically protected first. As described above, persons of skill in the art will be familiar with the proper ordering of the installation of protecting groups depending on the types of functional groups present on the chelator. This protected EC is then conjugated to a targeting ligand of any type described herein via any mode of conjugation described herein followed by removal of the thiol and amino protecting groups, which results in a chelator-targeting ligand conjugate.

In certain embodiments, conjugation between a chelator and a targeting ligand takes place in one step. In particular embodiments, the conjugation comprises a covalent attachment of a chelator to a targeting ligand, wherein the covalent attachment occurs in one step. As mentioned, such one-step procedures are preferable as they minimize time, reagents, waste and loss of product.

Chelator-targeting ligand conjugates synthesized by this method may next be chelated to a metal ion of any type described herein. Such methods of chelation are well known to those of ordinary skill in the art and are described herein. Examples of methods of chelation of metal ions to chelator-targeting ligand conjugates are described, for example, in U.S. Pat. No. 6,692,724. Methods described herein where a metal ion is chelated to a chelator may also serve as examples of how to chelate a metal ion to a chelator-targeting ligand conjugate.

Benefits of synthesizing chelator-targeting ligand conjugates via methods of the present invention using organic synthesis include, for example, obtaining conjugates of high purity relative to conjugates obtained via aqueous synthesis, and the efficient synthesis and purification of small-molecule compounds (e.g., 1000 g/mol or less). These benefits allow for conjugates that can be utilized in imaging, diagnostic, and/or therapeutic experiments and/or clinical trials.

6. Organic Synthesis of Chelator-Targeting Ligand Conjugates Chelated to a Metal Ion In another preferred embodiment, the present invention further provides a method of organically synthesizing chelator-targeting ligand conjugates chelated to a metal ion for imaging, diagnostic, or therapeutic use. The method includes, for example, first obtaining a chelator, such as EC. EC may then admixed with a metal ion, which may be a radionuclide or any other metal ion as described herein, in an organic medium in order to chelate to the EC via an $N_2S_2$ chelate. See, e.g., FIG. 2. Other methods of chelation are described herein (e.g., chelates of any combination of O, N and S) and chelation may occur by any method described herein. In non-limiting examples, metals such as technetium, indium, rhenium, gallium, copper, holmium, platinum, gadolinium, lutecium, yttrium, cobalt, calcium and arsenic can be chelated with a chelator such as EC. The EC chelated to a metal ion ("chelated EC") is then admixed with a targeting ligand, optionally protected with one or more protecting groups, in the presence of an organic medium in order to generate a chelator-targeting ligand conjugate chelated to a metal ion. The mode of conjugation may be via any mode described herein and may take place in one step or in more than one step.

Benefits of synthesizing metal ion-labeled chelator-targeting ligand conjugates via methods of the present invention using organic synthesis include, for example, obtaining conjugates of high purity relative to conjugates obtained via aqueous synthesis, and the efficient synthesis and purification of small-molecule compounds (e.g., 1000 g/mol or less). These benefits allow for conjugates that can be utilized in imaging, diagnostic, and/or therapeutic experiments and/or clinical trials.

7. Aqueous Synthesis of Chelator-Targeting Ligand Conjugates

The present invention further provides a method of synthesizing chelator-targeting ligand conjugates in an aqueous medium. Chelator-targeting ligand conjugates were prepared, in general, as a means of comparing the relative purity of such or similar products when synthesized in organic mediums. The method includes, for example, first obtaining a chelator, such as EC. EC is then dissolved in a basic aqueous solution and coupling agents of any type described herein are added. The targeting ligand is then added to this solution to generate the chelator-targeting ligand conjugate.

8. Aqueous Synthesis of Chelator-Targeting Ligand Conjugates Chelated to a Metal Ion The present invention further provides a method of synthesizing, in an aqueous medium, chelator-targeting ligand conjugates chelated to a metal ion. Like the aqueous synthesis mentioned above, chelator-targeting ligands conjugates chelated to a metal ion were prepared as a means of comparing the relative purity of such or similar products when synthesized in organic mediums. The method commences, in one embodiment, with obtaining a chelator chelated to a metal ion as described above ("Organic Synthesis of Chelator-Targeting Ligand Conjugates Chelated to a Metal Ion"). This chelator chelated to a metal ion may be, for example, chelated EC as described above. Chelation may occur by any method described herein. Chelated EC may be dissolved in a basic aqueous solution and coupling agents, as described herein, are added along with a targeting ligand of any type described herein in order to generate a chelator-targeting ligand conjugate chelated to a metal ion.

9. Conjugation of a Chelator with a Targeting Ligand

The present invention contemplates methods for conjugating a targeting ligand to a chelator (optionally chelated to a metal ion). The targeting ligand may be of any type described herein. One of ordinary skill in the art will be familiar with the means of conjugating targeting ligands to various functional groups. Most commonly, as between the chelator and the targeting ligand, one acts as the nucleophile and one acts as the electrophile such that conjugation takes place via a covalent bond. Non-limiting examples of such covalent bonds include an amide bond, an ester bond, a thioester bond and a carbon-carbon bond. In preferred embodiments, the conjugation takes place via an amide or ester bond. In some embodiments, the conjugation takes place at one or more functional groups of the chelator selected from the group consisting of carboxylic acid, amine and thiol. When acting as electrophiles, chelators and targeting ligands may comprise functional groups such as halogens and sulfonyls which act as leaving groups during conjugation. Targeting ligands may also comprise nucleophilic groups, such as —NH2, which may participate in conjugation with an electrophilic chelator.

Coupling agents, as used herein, are reagents used to facilitate the coupling of a chelator to a targeting ligand. Such agents are well known to those of ordinary skill in the art and may be employed in certain embodiments of methods of the present invention. Examples of coupling agents include, but are not limited to, sulfo-N-hydroxysuccinimide (sulfo-NHS), dimethylaminopyridine (DMAP), diazabicyclo[5.4.0]undec-7-ene (DBU), 1-ethyl-3-(3-dimethylaminopropyl)carbodiimide (EDAC) and dicyclohexylcarbodiimide (DCC). Other carbodiimides are also envisioned as coupling agents. Coupling agents are discussed, for example, in Bodansky, 1993 and Grant, 1992. These coupling agents may be used singly or in combination with each other or other agents to facilitate conjugation. Once the targeting ligand is conjugated using a coupling agent, urea is typically formed. The urea by-product may be removed by filtration. The conjugated product may then be purified by, for example, silica gel column chromatography or HPLC.

In general, the ligands for use in conjunction with the present invention will possess functional groups that are able to conjugate to one or more functional groups of a chelator, such as EC. For example, a targeting ligand may possess a halogenated position that will react with a free amine of a chelator to form the conjugate. If functional groups are not available, or if an optimal functional group is not available, a desired ligand may still be conjugated to a chelator, such as EC, by adding a linker, such as ethylenediamine, amino propanol, diethylenetriamine, aspartic acid, polyaspartic acid, glutamic acid, polyglutamic acid, cysteine, glycine or lysine. For example, U.S. Pat. No. 6,737,247 discloses several linkers which may be used with the present invention and is hereby incorporated by reference in its entirety without disclaimer. U.S. Pat. No. 5,605,672 discloses several "preferred backbones" which may be used as linkers in the present invention and is hereby incorporated by reference in its entirety. In certain embodiments, the chelator may be conjugated to a linker, and the linker is conjugated to the targeting ligand. In other embodiments more than one linker may be used; for example, a chelator may be conjugated to a linker, and the linker is conjugated to a second linker, wherein the second linker is conjugated to the targeting ligand. In certain embodiments, two, three, four, or more linkers that are conjugated together may be used to conjugate a chelator and targeting ligand. However, it is generally preferable to only use a single linker to conjugate a chelator and a targeting ligand.

Some chelators, such as EC, are water soluble. In some embodiments, the chelator-targeting ligand conjugate chelated to a metal ion of the invention is water soluble. Many of the targeting ligands used in conjunction with the present invention will be water soluble, or will form a water soluble compound when conjugated to the chelator. If the targeting ligand is not water soluble, however, a linker which will increase the solubility of the ligand may be used. Linkers may attach to, for example, an aliphatic or aromatic alcohol, amine, peptide or to a carboxylic acid. Linkers may be, for example, either poly amino acids (peptides) or amino acids such as glutamic acid, aspartic acid or lysine. Table 2 illustrates preferred linkers for specific drug functional groups.

Benefits of synthesizing chelator-targeting ligand conjugates optionally chelated to one or more valent metal ions via methods of the present invention using organic synthesis include, for example, obtaining conjugates of high purity relative to conjugates obtained via aqueous synthesis, and the efficient synthesis and purification of small-molecule compounds (e.g., 1000 g/mol or less). These benefits allow for conjugates that can be utilized in imaging, diagnostic, and/or therapeutic experiments and/or clinical trials.

TABLE 2

| Linkers | | |
| --- | --- | --- |
| Drug Functional Group | Linker | Example |
| Aliphatic or phenolic-OH | EC-poly(glutamic acid) (MW 750-15,000) or EC poly(aspartic acid) (MW 2000-15,000) or bromo ethylacetate or EC-glutamic acid or EC-aspartic acid. | estradiol, topotecan, paclitaxel, raloxifen etoposide |
| Aliphatic or aromatic-NH$_2$ or peptide | EC-poly(glutamic acid) (MW 750-15,000) or EC-poly(aspartic acid) (MW 2000-15,000) or EC-glutamic acid (mono- or diester) or EC-aspartic acid. | doxorubicin, mitomycin C, endostatin, annexin V, LHRH, octreotide, VIP |
| Carboxylic acid or peptide | Ethylene diamine, lysine | methotrexate, folic acid |

10. Chelation of a Metal Ion

The present invention further contemplates methods for the chelation (also called coordination) of one or more metal ions to a chelator or a chelator-targeting ligand conjugate.

Such chelation steps may take place in organic media. In other embodiments, chelation takes place in aqueous media. In certain embodiments, the chelator and the targeting ligand may each contribute to the chelation of the metal ion. In preferred embodiments, the metal ion is chelated only to the chelator. The chelated metal ion may be bound via, for example, an ionic bond, a covalent bond, or a coordinate covalent bond (also called a dative bond). Methods of such coordination are well known to those of ordinary skill in the art. In one embodiment, coordination may occur by admixing a metal ion into a solution containing a chelator. In another embodiment, coordination may occur by admixing a metal ion into a solution containing a chelator-targeting ligand conjugate. In one embodiment, chelation occurs to the chelator, with or without a targeting ligand, via an $N_2S_2$ chelate formed by the chelator, such as ethylenedicysteine (EC). The chelator and the targeting ligand may each be protected by one or more protecting groups before or after chelation with the metal ion.

Chelation may occur at any atom or functional group of a chelator or targeting ligand that is available for chelation. The chelation may occur, for example, at one or more N, S, O or P atoms. Non-limiting examples of chelation groups include $NS_2$, $N_2S$, $S_4$, $N_2S_2$, $N_3S$ and $NS_3$, and $O_4$. In preferred embodiments, a metal ion is chelated to three or four atoms. In some embodiments, the chelation occurs among one or more thiol, amine or carboxylic acid functional groups. The chelation, in particular embodiments, may be to a carboxyl moiety of glutamate, aspartate, an analog of glutamate, or an analog of aspartate. These embodiments may include multiple metal ions chelated to poly(glutamate) or poly(aspartate) chelators. In some embodiments, chelation of the metal ion is to a targeting ligand, such as to carboxyl groups of a tissue-specific ligand. In preferred embodiments, the chelation is between one or more thiol groups and one or more amine groups of the chelator.

In some non-limiting examples, the metal ion may be technetium, indium, rhenium, gallium, copper, holmium, platinum, gadolinium, lutecium, yttrium, cobalt, calcium, arsenic, or any isotope thereof. Any metal ion described herein may be chelated to a compound of the present invention.

11. Reducing Agents

For purposes of the present invention, when the metal ion is technetium it is preferred that the Tc be in the +4 oxidation state. The preferred reducing agent for use this purpose is stannous ion in the form of stannous chloride ($SnCl_2$) to reduce the Tc to its +4 oxidation state. However, it is contemplated that other reducing agents, such as dithionate ion or ferrous ion may be useful in conjunction with the present invention. It is also contemplated that the reducing agent may be a solid phase reducing agent. The amount of reducing agent can be important as it is necessary to avoid the formation of a colloid. It is preferable, for example, to use from about 10 to about 100 μg $SnCl_2$ per about 100 to about 300 mCi of Tc pertechnetate. The most preferred amount is about 0.1 mg $SnCl_2$ per about 200 mCi of Tc pertechnetate and about 2 mL saline. This typically produces enough Tc-EC-targeting ligand conjugate for use in 5 patients.

F. EXAMPLES OF IMAGING MODALITIES

1. Gamma Camera Imaging

A variety of nuclear medicine techniques for imaging are known to those of ordinary skill in the art. Any of these techniques can be applied in the context of the imaging methods of the present invention to measure a signal from the reporter. For example, gamma camera imaging is contemplated as a method of imaging that can be utilized for measuring a signal derived from the reporter. One of ordinary skill in the art would be familiar with techniques for application of gamma camera imaging (see, e.g., Kundra et al., 2002, herein specifically incorporated by reference). In one embodiment, measuring a signal can involve use of gamma-camera imaging of a 111-In-octreotide-SSRT2A reporter system.

2. PET and SPECT

Radionuclide imaging modalities (positron emission tomography (PET); single photon emission computed tomography (SPECT)) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits low-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}C$, $^{13}N$, $^{15}O$, $^{18}F$, $^{82}Rb$, $^{62}Cu$, and $^{68}Ga$. SPECT radiopharmaceuticals are commonly labeled with positron emitters such as $^{99m}Tc$, $^{201}Tl$, and $^{67}Ga$. Regarding brain imaging, PET and SPECT radiopharmaceuticals are classified according to blood-brain-barrier permeability (BBB), cerebral perfusion and metabolism receptor-binding, and antigen-antibody binding (Saha et al., 1994). The blood-brain-barrier SPECT agents, such as $^{99m}TcO4$-DTPA, $^{201}Tl$, and [$^{67}Ga$]citrate are excluded by normal brain cells, but enter into tumor cells because of altered BBB. SPECT perfusion agents such as [$^{123}I$]IMP, [$^{99m}Tc$]HMPAO, [$^{99m}Tc$]ECD are lipophilic agents, and therefore diffuse into the normal brain. Important receptor-binding SPECT radiopharmaceuticals include [$^{123}I$]QNE, [$^{123}I$]IBZM, and [$^{123}I$]iomazenil. These tracers bind to specific receptors, and are of importance in the evaluation of receptor-related diseases.

3. Computerized Tomography (CT)

Computerized tomography (CT) is contemplated as an imaging modality in the context of the present invention. By taking a series of X-rays, sometimes more than a thousand, from various angles and then combining them with a computer, CT made it possible to build up a three-dimensional image of any part of the body. A computer is programmed to display two-dimensional slices from any angle and at any depth.

In CT, intravenous injection of a radiopaque contrast agent can assist in the identification and delineation of soft tissue masses when initial CT scans are not diagnostic. Similarly, contrast agents aid in assessing the vascularity of a soft tissue or bone lesion. For example, the use of contrast agents may aid the delineation of the relationship of a tumor and adjacent vascular structures.

CT contrast agents include, for example, iodinated contrast media. Examples of these agents include iothalamate, iohexyl, diatrizoate, iopamidol, ethiodol and iopanoate. Gadolinium agents have also been reported to be of use as a CT contrast agent (see, e.g., Henson et al., 2004). For example, gadopentate agents has been used as a CT contrast agent (discussed in Strunk and Schild, 2004).

4. Magnetic Resonance Imaging (MRI)

Magnetic resonance imaging (MRI) is an imaging modality that is newer than CT that uses a high-strength magnet and radio-frequency signals to produce images. The most abundant molecular species in biological tissues is water. It is the quantum mechanical "spin" of the water proton nuclei that ultimately gives rise to the signal in imaging experiments. In MRI, the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. By collecting and analyzing these signals, it is possible to compute a three-dimensional image which, like a CT image, is normally displayed in two-dimensional slices.

Contrast agents used in MR imaging differ from those used in other imaging techniques. Their purpose is to aid in distinguishing between tissue components with identical signal characteristics and to shorten the relaxation times (which will produce a stronger signal on T1-weighted spin-echo MR images and a less intense signal on T2-weighted images). Examples of MRI contrast agents include gadolinium chelates, manganese chelates, chromium chelates, and iron particles.

Both CT and MRI provide anatomical information that aid in distinguishing tissue boundaries and vascular structure. Compared to CT, the disadvantages of MRI include lower patient tolerance, contraindications in pacemakers and certain other implanted metallic devices, and artifacts related to multiple causes, not the least of which is motion (Alberico et al., 2004). CT, on the other hand, is fast, well tolerated, and readily available but has lower contrast resolution than MRI and requires iodinated contrast and ionizing radiation (Alberico et al., 2004). A disadvantage of both CT and MRI is that neither imaging modality provides functional information at the cellular level. For example, neither modality provides information regarding cellular viability.

5. Optical Imaging

Optical imaging is another imaging modality that has gained widespread acceptance in particular areas of medicine. Examples include optical labelling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erythrosin, Texas red, a derivative of Texas red, malachite green, nanogold sulfosuccinimidyl ester, cascade blue, a coumarin derivative, a naphthalene, a pyridyloxazole derivative, cascade yellow dye, or dapoxyl dye.

6. Ultrasound

Another biomedical imaging modality that has gained widespread acceptance is ultrasound. Ultrasound imaging has been used noninvasively to provide realtime cross-sectional and even three-dimensional images of soft tissue structures and blood flow information in the body. High-frequency sound waves and a computer to create images of blood vessels, tissues and organs.

Ultrasound imaging of blood flow can be limited by a number of factors such as size and depth of the blood vessel. Ultrasonic contrast agents, a relatively recent development, include perfluorine and perfluorine analogs, which are designed to overcome these limitations by helping to enhance grey-scale images and Doppler signals.

7. Procedure for Dual Imaging

Certain embodiments of the present invention pertain to methods of imaging a site within a subject using two imaging modalities that involve measuring a first signal and a second signal from the imaging moiety-chelator-metal ion complex. The first signal is derived from the metal ion and the second signal is derived from the imaging moiety. As set forth above, any imaging modality known to those of ordinary skill in the art can be applied in these embodiments of the present imaging methods.

The imaging modalities are performed at any time during or after administration of the composition comprising the diagnostically effective amount of the composition of the present invention. For example, the imaging studies may be performed during administration of the dual imaging composition of the present invention, or at any time thereafter. In some embodiments, the first imaging modality is performed beginning concurrently with the administration of the dual imaging agent, or about 1 sec, 1 hour, 1 day, or any longer period of time following administration of the dual imaging agent, or at any time in between any of these stated times.

The second imaging modality may be performed concurrently with the first imaging modality, or at any time following the first imaging modality. For example, the second imaging modality may be performed about 1 sec, about 1 hour, about 1 day, or any longer period of time following completion of the first imaging modality, or at any time in between any of these stated times. In certain embodiments of the present invention, the first and second imaging modalities are performed concurrently such that they begin at the same time following administration of the agent. One of ordinary skill in the art would be familiar with performance of the various imaging modalities contemplated by the present invention.

In some embodiments of the present methods of dual imaging, the same imaging device is used to perform a first imaging modality and a second imaging modality. In other embodiments, a different imaging device is used to perform the second imaging modality. One of ordinary skill in the art would be familiar with the imaging devices that are available for performance of a first imaging modality and a second imaging modality, and the skilled artisan would be familiar with use of these devices to generate images.

G. RADIOLABELED AGENTS

As set forth above, certain embodiments of the compositions of the present invention include a metal ion chelated to a chelator as set forth above. In some embodiments, the metal ion is a radionuclide. Radiolabeled agents, compounds, and compositions provided by the present invention are provided having a suitable amount of radioactivity. For example, in forming $^{99m}$Tc radioactive complexes, it is generally preferred to form radioactive complexes in solutions containing radioactivity at concentrations of from about 0.01 millicurie (mCi) to about 300 mCi per mL.

Radiolabeled imaging agents provided by the present invention can be used for visualizing sites in a mammalian body. In accordance with this invention, the imaging agents are administered by any method known to those of ordinary skill in the art. For example, administration may be in a single unit injectable dose. Any of the common carriers known to those with skill in the art, such as sterile saline solution or plasma, may be utilized after radiolabeling for preparing the compounds of the present invention for injection. Generally, a unit dose to be administered has a radioactivity of about 0.01 mCi to about 300 mCi, preferably 10 mCi to about 200 mCi. The solution to be injected at unit dosage is from about 0.01 mL to about 10 mL.

After intravenous administration of a diagnostically effective amount of a composition of the present invention, imaging can be performed. Imaging of a site within a subject, such as an organ or tumor can take place, if desired, in hours or even longer, after the radiolabeled reagent is introduced into a patient. In most instances, a sufficient amount of the administered dose will accumulate in the area to be imaged within about 0.1 of an hour. As set forth above, imaging may be performed using any method known to those of ordinary skill in the art. Examples include PET, SPECT, and gamma scintigraphy. In gamma scintigraphy, the radiolabel is a gamma-radiation emitting radionuclide and the radiotracer is located using a gamma-radiation detecting camera. The imaged site is detectable because the radiotracer is chosen either to localize at a pathological site (termed positive contrast) or, alternatively, the radiotracer is chosen specifically not to localize at such pathological sites (termed negative contrast).

H. KITS

Certain embodiments of the present invention are generally concerned with kits for preparing an imaging or diagnostic agent. For example, in some embodiments the kit includes one or more sealed containers that contain a predetermined quantity of a chelator-targeting ligand conjugate. In some embodiments, the kit further includes a sealed container containing a metal ion. For example, the metal ion may be a radionuclide or a cold metal ion.

A kit of the present invention may include a sealed vial containing a predetermined quantity of a chelator of the present invention and a sufficient amount of reducing agent to label the compound with a metal ion. In some embodiments of the present invention, the kit includes a metal ion that is a radionuclide. In certain further embodiments, the radionuclide is $^{99m}$Tc. In further embodiments of the present invention, the chelator is conjugated to a targeting ligand that can be any of those targeting ligands discussed elsewhere in this application.

The kit may also contain conventional pharmaceutical adjunct materials such as, for example, pharmaceutically acceptable salts to adjust the osmotic pressure, buffers, preservatives and the like.

In certain embodiments, an antioxidant is included in the composition to prevent oxidation of the chelator moiety. In certain embodiments, the antioxidant is vitamin C (ascorbic acid). However, it is contemplated that any other antioxidant known to those of ordinary skill in the art, such as tocopherol, pyridoxine, thiamine, or rutin, may also be used. The components of the kit may be in liquid, frozen, or dry form. In a preferred embodiment, kit components are provided in lyophilized form.

The cold (that is, non-radioactivity containing) instant kit is considered to be a commercial product. The cold instant kit could serve a radiodiagnostic purpose by adding pertechnetate to vial with API and bulking agents (agents which have not been tested yet). The technology is known as the "shake and shoot" method to those of skill in the art. The preparation time of radiopharmaceuticals would be less than 15 min. The same kit could also encompass chelators or chelator-targeting ligand conjugates that could be chelated with different metals for different imaging applications. For instance, copper-61 (3.3 hrs half life) for PET; gadolinium for MRI. The cold kit itself could be used for prodrug purposes to treat disease. For example, the kit could be applied in tissue-specific targeted imaging and therapy.

I. HYPERPROLIFERATIVE DISEASE

Certain aspects of the present invention pertain to compositions wherein a therapeutic moiety is conjugated to a chelator of the present invention. When a metal ion is chelated to a chelator or to both a chelator and its conjugated targeting ligand, the composition of the present invention may, in certain embodiments, be useful in dual imaging and therapy. In certain particular embodiments, the therapeutic moiety is a moiety that is an agent known or suspected to be of benefit in the treatment or prevention of hyperproliferative disease in a subject. The subject may be an animal, such as a mammal. In certain particular embodiments, the subject is a human.

In other embodiments of the present invention, the metal ion is a therapeutic metal ion (e.g., Re-188, Re-187, Re-186, Ho-166, Y-90, Sr-89, and Sm-153), and the chelator-metal ion chelate is an agent that is a therapeutic agent (rather than an imaging agent) that can be applied in the treatment or prevention of a hyperproliferative disease.

A hyperproliferative disease is herein defined as any disease associated with abnormal cell growth or abnormal cell turnover. For example, the hyperproliferative disease may be cancer. The term "cancer" as used herein is defined as an uncontrolled and progressive growth of cells in a tissue. A skilled artisan is aware other synonymous terms exist, such as neoplasm or malignancy or tumor. Any type of cancer is contemplated for treatment by the methods of the present invention. For example, the cancer may be breast cancer, lung cancer, ovarian cancer, brain cancer, liver cancer, cervical cancer, colon cancer, renal cancer, skin cancer, head and neck cancer, bone cancer, esophageal cancer, bladder cancer, uterine cancer, stomach cancer, pancreatic cancer, testicular cancer, lymphoma, or leukemia. In other embodiments of the present invention, the cancer is metastatic cancer.

J. DUAL CHEMOTHERAPY AND RADIATION THERAPY ("RADIOCHEMOTHERAPY")

In certain embodiments of the present invention, the compositions of the present invention are suitable for dual chemotherapy and radiation therapy (radio chemotherapy). For example, the chelator as set forth herein may be chelated to a metal ion that is a therapeutic metal ion, as well as a targeting ligand that is a therapeutic moiety (such as an anti-cancer moiety). As another example, a therapeutic metal ion may be chelated to both a chelator and its targeting ligand conjugate.

For example, the metal ion may be a beta-emitter. As herein defined, a beta emitter is any agent that emits beta energy of any range. Examples of beta emitters include Re-188, Re-187, Re-186, Ho-166, Y-90, and Sn-153. One of ordinary skill in the art would be familiar with these agents for use in the treatment of hyperproliferative disease, such as cancer.

One of ordinary skill in the art would be familiar with the design of chemotherapeutic protocols and radiation therapy protocols that can applied in the administration of the compounds of the present invention. As set forth below, these agents may be used in combination with other therapeutic modalities directed at treatment of a hyperproliferative disease, such as cancer. Furthermore, one of ordinary skill in the art would be familiar with selecting an appropriate dose for administration to the subject. The protocol may involve a single dose, or multiple doses. The patient would be monitored for toxicity and response to treatment using protocols familiar to those of ordinary skill in the art.

K. PHARMACEUTICAL PREPARATIONS

Pharmaceutical compositions of the present invention comprise a therapeutically or diagnostically effective amount of a composition of the present invention. The phrases "pharmaceutical or pharmacologically acceptable" or "therapeutically effective" or "diagnostically effective" refers to molecular entities and compositions that do not produce an adverse, allergic or other untoward reaction when administered to an animal, such as, for example, a human, as appropriate. The preparation of therapeutically effective or diagnostically effective compositions will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by the FDA Office of Biological Standards.

As used herein, "a composition comprising a therapeutically effective amount" or "a composition comprising a diagnostically effective amount" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. Except insofar as any conventional carrier is incompatible with the active ingredient, its use in the present compositions is contemplated.

The compositions of the present invention may comprise different types of carriers depending on whether it is to be administered in solid, liquid or aerosol form, and whether it need to be sterile for such routes of administration as injection. The compositions of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art.

The actual required amount of a composition of the present invention administered to a patient can be determined by physical and physiological factors such as body weight, severity of condition, the tissue to be imaged, the type of disease being treated, previous or concurrent imaging or therapeutic interventions, idiopathy of the patient, and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of the chelator-metal ion chelate. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight to about 1000 mg/kg/body weight or any amount within this range, or any amount greater than 1000 mg/kg/body weight per administration.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The compositions of the present invention may be formulated in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions may be prepared using techniques such as filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO (dimethylsulfoxide) as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

L. COMBINATIONAL THERAPY

Certain aspects of the present invention pertain to compositions comprising a chelator that is conjugated to a targeting ligand that is a therapeutic moiety. In other embodiments, the chelator includes an amino acid sequence that is a therapeutic amino acid sequence.

These compositions can be applied in the treatment of diseases, such as cancer and cardiovascular disease, along with another agent or therapy method. Treatment with these compositions of the present invention may precede or follow the other therapy method by intervals ranging from minutes to weeks. In embodiments where another agent is administered, one would generally ensure that a significant period of time did not expire between the time of each delivery, such that the agents would still be able to exert an advantageously combined effect on the cell. For example, it is contemplated that one may administer two, three, three or more doses of one agent substantially simultaneously (i.e., within less than about a minute) with the compositions of the present invention. In other aspects, a therapeutic agent or method may be administered within about 1 minute to about 48 hours or more prior to and/or after administering a therapeutic amount of a composition of the present invention, or prior to and/or after any amount of time not set forth herein. In certain other embodiments, a composition of the present invention may be administered within of from about 1 day to about 21 days prior to and/or after administering another therapeutic modality, such as surgery or gene therapy. In some situations, it may be desirable to extend the time period for treatment significantly, however, where several weeks (e.g., about 1 to 8 weeks or more) lapse between the respective administrations.

Various combinations may be employed, as demonstrated below, wherein a conjugate of the present invention is designated "A" and the secondary agent, which can be any other therapeutic agent or method, is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the compositions of the present invention to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the described agent. These therapies include but are not limited to additional pharmacotherapy (such as chemotherapy for cancer), additional radiotherapy, immunotherapy, gene therapy and surgery.

1. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4. Genes

In yet another embodiment, the secondary treatment is a gene therapy in which a therapeutic composition is administered before, after, or at the same time as the therapeutic agents of the present invention. Delivery of a therapeutic amount of a composition of the present invention in conjunction with a vector encoding a gene product will have a combined anti-hyperproliferative effect on target tissues.

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

M. OTHER EMBODIMENTS OF THE PRESENT INVENTION

In one aspect, the present invention generally pertains to a method of synthesizing a chelator, such as EC, comprising at least three functional groups, the method comprising obtaining a chelator and either:
  (a) protecting at least one first functional group of the chelator with a first protecting agent to generate a firstly protected chelator; or
  (b) chelating the chelator to a metal ion to generate a metal ion-labeled chelator.

Any method of synthesis as described herein, such as this, may take place in an organic medium, as described herein. The method may further comprise at least one purification step, as described herein. Chelators, functional groups, metal ions and modes of chelation and conjugation that may be used in the methods of the present invention are familiar to those of ordinary skill in the art and are described herein. The chelator may further comprise a spacer as described herein, such as ethylene. Such chelators are useful intermediates for the preparation of chelator-targeting ligand conjugates.

In some embodiments, the method comprises protecting at least one first functional group of the chelator with a first protecting agent to generate a firstly protected chelator. In certain embodiments, the first functional group is a thiol functional group. In certain embodiments, the first protecting agent is a thiol protecting agent. In further embodiments, the thiol protecting agent is selected from a group consisting of an alkyl halide, a benzyl halide, a benzoyl halide, a sulfonyl halide, a triphenylmethyl halide, a methoxytriphenylmethyl halide and cysteine.

The method may, in some embodiments, comprise protecting a second functional group with a second protecting agent to generate a secondly protected chelator. In certain embodiments, the first functional group comprises at least one thiol functional group and the second functional group comprises at least one amine functional group. In some embodiments, a thiol functional group is first protected with a thiol protecting agent and then an amine functional group is protected with an amine protecting agent. In further embodiments, an amine protecting agent is selected from the group consisting of benzylchloroformate, p-nitro-chlorobenzylformate, ethylchloroformate, di-tert-butyl-dicarbonate, triphenylmethyl chloride and methoxytriphenylmethyl chloride. An example of a chelator that may be prepared comprises ethylenedicysteine, wherein the two thiol groups of ethylenedicysteine are protected with two equivalents of a thiol protecting agent followed by protection of the two amine groups of ethylenedicysteine with two equivalents of an amine protecting agent. Since thiol groups are more reactive than amine groups, thiol groups will typically be protected before amine groups are protected.

In other embodiments, the method further comprises removing one or more protecting groups from any composition described herein comprising one or more protecting groups. The protecting groups may be removed, for example, from the chelator moiety, the targeting ligand moiety, or both moieties in one or more steps before or after a chelator-targeting ligand conjugate is chelated to a metal ion, as described herein. Protecting groups are described in more detail herein, including their installation and removal.

Any composition of the present invention may be purified via any method known to those of skill in the art. Methods of purification are described in more detail herein. In some embodiments, the firstly protected chelator is between about 90% and about 99.9% pure. In some embodiments, the secondly protected chelator is between about 90% and about 99.9% pure.

In some embodiments, methods of the present invention further comprise conjugation of a chelator to a targeting ligand, wherein the targeting ligand and/or the chelator comprises at least one functional group to form a chelator-targeting ligand conjugate. In some embodiments, a functional group of the targeting ligand is protected by at least one protecting agent prior to conjugation to the chelator. In some embodiments, at least one functional group is a carboxylic acid functional group. In some embodiments, the functional groups of the chelator and the targeting ligand together form a chelate. Chelation of the metal ion to the chelator can be by any method known to those of ordinary skill in the art.

A chelator-targeting ligand conjugate of the present invention may further comprise a linker between the chelator and the targeting ligand, as described herein. As mentioned, the targeting ligand may of any type known to those of skill in the art, and such ligands are discussed in more detail herein.

Other general aspects of the present invention contemplate a method of synthesizing a metal ion labeled-chelator-targeting ligand conjugate, comprising:
  (a) obtaining a protected chelator comprising at least three functional groups protected by at least one protecting agent;
  (b) conjugating the protected chelator to a targeting ligand to generate a chelator-targeting ligand conjugate;
  (c) removing at least one protecting group from the chelator-targeting ligand conjugate;
  (d) chelating a metal ion to the chelator of the chelator-targeting ligand conjugate; and
  (e) removing any remaining protecting groups.

The chelator, protecting agents, functional groups, mode of conjugation, targeting ligand, method of removing a protecting group, mode of chelation and metal ion may be that of any type described herein. The method may take place in an organic medium, as described herein. The method may comprise one or more purification steps, as described herein. In some embodiments, at least one functional group of the targeting ligand is protected by at least one protecting agent prior to conjugation. In preferred embodiments, three or four atoms of the chelator are available for chelation.

Other general aspects of the present invention contemplate a method of synthesizing a metal ion labeled-chelator-targeting ligand conjugate comprising:
(a) obtaining a chelator comprising at least three functional groups;
(b) chelating a metal ion to the chelator to generate a metal ion labeled-chelator;
(c) conjugating the metal ion labeled-chelator to a targeting ligand.

The chelator, functional groups, mode of conjugation, targeting ligand, mode of chelation and metal ion may be that of any type described herein. The method may take place in an organic medium, as described herein. The method may comprise on or more purification steps, as described herein. In some embodiments, at least one functional group of the targeting ligand is protected by at least one protecting agent prior to conjugation. The method may further comprise the removal of all protecting groups from the metal ion labeled-chelator-targeting ligand conjugate. The method also contemplates, in certain embodiments, at least one functional group of the targeting ligand being protected by at least one protecting agent prior to conjugation.

The present invention also contemplates kits for preparing an imaging agent, a chemotherapeutic agent, or a radio/chemotherapeutic agent, comprising one or more sealed containers, and a predetermined quantity of any composition as described herein in one or more of the sealed containers. The present invention also contemplates, in some embodiments, an imaging, chemotherapeutic, or radio/chemotherapeutic agent, comprising any composition as described herein.

In some embodiments, the present invention contemplates a method of imaging or treating a subject, comprising administering to the subject a pharmaceutically effective amount of any composition as described herein. The subject may be a mammal, such as a human.

N. METHODS OF DIAGNOSIS, TREATMENT, OR IMAGING IN A SUBJECT WITH KNOWN OR SUSPECTED HEART DISEASE

Embodiments of the present invention also generally pertain to methods of diagnosis, treatment, or imaging in a subject with known or suspected heart disease. The subject can be any subject, such as a mammal or avian species. The mammal, for example, may be a dog, cat, rat, mouse, or human. In preferred embodiments, the subject is a human with known or suspected cardiovascular disease.

The cardiovascular disease can be any disease of the heart or of a blood vessel. The blood vessel may be a coronary vessel, or may be a vessel other than a coronary vessel. The vessel may be an artery, vein, arteriole, venule, or capillary.

Examples of cardiovascular diseases include diseases of the heart, such as myocardial infarction, myocardial ischemia, angina pectoris, congestive heart failure, cardiomyopathy (congenital or acquired), arrhythmia, or valvular heart disease. In particular embodiments, the subject is known or suspected to have myocardial ischemia.

The subject, for example, may be a patient who presents to a clinic with signs or symptoms suggestive of myocardial ischemia or myocardial infarction. Imaging of the heart of the subject to diagnose disease may involve administering to the subject a pharmaceutically effective amount of a metal ion labeled chelator-targeting ligand conjugate synthesized using any of the methods set forth herein. Imaging can be performed using any imaging modality known to those of ordinary skill in the art. In particular embodiments, imaging involves use radionuclide-based imaging technology, such as PET or SPECT. In particular embodiments, the metal ion-labeled radionuclide-targeting ligand conjugate is 99m-Tc-EC-glucosamine. Glucosamine is actively taken up by viable myocardial tissue. Areas of ischemic myocardium would take up less or no conjugate. Severity of ischemia can be visually assessed or graded depending on magnitude of the signal that is measured using any method known to those of ordinary skill in the art. In some embodiments, imaging using any of the conjugates set forth herein is performed before, during, or after imaging of the heart using a second imaging modality. For example, the second imaging modality may be thallium scinigraphy.

Myocardial Perfusion SPECT (MPS) consist of a combination of a stress modality (exercise or pharmacologic) with rest and stress administration and imaging of radiopharmaceuticals. Thallium has excellent physiologic properties for myocardial perfusion imaging. Being highly extracted during the first pass through the coronary circulation, a linear relationship between blood flow to viable myocardium and thallium uptake has been shown during exercise; however, at very high levels of flow, a "roll-off" in uptake occurs. As an unbound potassium analogue, thallium redistributes over time. Its initial distribution is proportional to regional myocardial perfusion and at equilibrium, the distribution of thallium is proportional to the regional potassium pool, reflecting viable myocardium. The mechanisms of thallium redistribution are differential washout rates between hypoperfused but viable myocardium and normal zones and wash-in to initially hypoperfused zones. The washout rate of thallium is the concentration gradient between the myocardial cell and the blood. There is slower blood clearance of thallium following resting or low-level exercise injection. Diffuse slow washout rates, mimicking diffuse ischemia, may be observed in normal patients who do not achieve adequate levels of stress. Hyperinsulinemic states slow redistribution, leading to an underestimation of viable myocardium; thus fasting is recommended prior to and for 4 hrs following thallium injection. This is why if EC-G is used as an viable agent in combination with thallium it will target the precise area of interest which would be the viable area (Angello et al., 1987; Gutman et al., 1983; Pohost et al., 1977).

Imaging using any of the metal ion-labeled chelator-targeting ligand conjugates of the present invention may also be performed in conjunction with other diagnostic methods, such as measurement of cardiac isozymes, or cardiac catheterization. The imaging may be performed at various intervals following onset of symptoms, or can be performed to assess for changes in myocardial perfusion over time.

O. EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

The following figures, chemical structures and synthetic details provide certain compounds of the present invention.

Example 1

Non-Limiting Example of an Organic Synthesis of N,N-Ethylenedicysteine-Glucosamine (EC-G). See FIG. 1

Step 1: Synthesis of S,S'-Bis-benzyl-N,N'-ethylenedicysteine (Bz-EC)

Cysteine-HCl (30 g) was dissolved in water (100 mL). To this, 37% formaldehyde (22.3 mL) was added and the reaction mixture was stirred overnight at room temperature. Pyridine (25 mL) was then added and a precipitate formed. The crystals were separated and washed with ethanol (50 mL), then filtered with a Buchner funnel. The crystals were triturated with petroleum ether (150 mL), again filtered and dried. The precursor, L-thiazolidine-4-carboxylic acid (m.p. 195° C., reported 196-197° C.) weighed 23.408 g. The precursor (22 g) was dissolved in liquid ammonia (200 mL) and refluxed. Sodium metal was added until a persistent blue color appeared for 15 min. Ammonium chloride was added to the blue solution, the solvents were evaporated to dryness. The residue was dissolved in water (200 mL) and the pH was adjusted to 2 with concentrated HCl. A precipitate was formed, filtered and washed with water (500 mL). The solid was dried in a calcium chloride dessicator. EC was then prepared 10.7 g (m.p. 237° C., reported 251-253° C.). The structure of EC was confirmed by H-1 and C-13 NMR. EC (2.684 g, 10 mmol) was dissolved in 1N NaOH (40 mL). Benzyl chloride (5.063 g, 40 mmol) was dissolved in dioxane (30 mL) and stirred. The reaction was stirred for 30 min. The pH of the solution was adjusted to 2 with concentrated HCl. The precipitate was filtered and washed with water and recrystallized from trifluoroacetic acid, yielding 79.0% (3.5454 g), m.p. 227-229° C. (dec.) (reported 229-230° C.). The structure of Bz-EC was confirmed by H-1 and C-13 NMR.

Step 2: Synthesis of S,S'-Bis-benzyl-N,N'-bis-CBZ ethylenedicysteine (Cbz-Bz-EC)

Bz-EC (2.243 g, 5 mmol) was dissolved in sodium carbonate (1.20 g, 11.2 mmol) solution and the pH was adjusted to 10 using 1N NaOH. The final aqueous volume was 30 mL. Benzyl chloroformate (233 mL, 16.5 mmol) was dissolved in dioxane (0.75 mL) and stirred. The pH was adjusted to 10 by adding solid $Na_2CO_3$. The reaction mixture was stirred for 2 hours and extracted with diethyl ether to remove the excess benzyl chloroformate (CBZ). The pH of the aqueous layer was adjusted to 2 with 1N HCl and extracted with ethyl acetate. The organic layer was dried over magnesium sulfate and the solvent was evaporated. The residue was chromatographed on a silica gel column column eluted with $CH_2Cl_2$:acetic acid (99:1) to $CH_2Cl_2$:methanol: acetic acid (94:5:1) to yield the desired product 87.2% (3.127 g). The structure of Cbz-Bz-EC was confirmed by H-1 and C-13 NMR.

Step 3: Synthesis of S,S'-Bis-benzyl-N,N'-bis-CBZ ethylenedicysteine-glucosamine (tetra acetate) Conjugate (Cbz-Bz-EC-G-4-Ac)

To a stirred flask of dichloromethane (22 mL), Cbz-Bz-EC (2.1467 g, 3 mmol) was added. This was followed by dicyclohexylcarbodiimide (DCC) (2.476 g, 12 mmol) and dimethylaminopyridine (1.466 g, 12 mmol). Tetraacetylated glucosamine hydrochloride (2.533 g, 6.6 mmol) (4-Ac-G-HCl) (Oakwood Products Inc., West Columbia, S.C.) was added to the mixture and stirred until completely dissolved. The structure of 4-Ac-G-HCl was confirmed by H-1 and C-13 NMR. The reaction was stirred at room temperature overnight. Water (0 5 mL) was added and the solid was filtered. The filtrate was dried over magnesium sulfate and the solvent was evaporated. The product was purified by silica gel column chromatography using dichloromethane: methanol:acetic acid (9.9:0:0.1) to 56.4:3:0.6 as a mobile phase. The product was isolated 66.4% yield (2.7382 g). H-1 and C-13 NMR of Cbz-Bz-EC-G-4-Ac provided confirmation as well as mass spectrometry.

Step 4: Synthesis of N,N'-ethylenedicysteine-glucosamine (EC-G)

Cbz-Bz-EC-G-4-Ac (687.7 mg, 0.5 mmol) was dissolved in liquid ammonia (20 mL) and pieces of sodium (223 mg, 10 mmol) were added. After adding all of the sodium, the reaction mixture sustained a dark blue color for 20 minutes. Ammonium chloride (641.9 mg, 12 mmol) was added slowly and the dark blue color solution turned colorless. The liquid ammonia was removed by nitrogen. The residual solid was dissolved in water and dialyzed overnight using MW<500. The crude product weighed 206.7 mg (yield: 70%). H-1 and C-13 NMR of the crude EC-G bis-acetylated compound were obtained along with mass spectra. The molecular ion was 861 which contains the matrix 187 and parent ion 674 (EC-G bis-acetylated). The major ion (100%) was 656 which was from the loss of water. EC-G bis-acetylated compound (200 mg) was further purified by dissolving in sodium carbonate and stirring for 2 hours. The product, EC-G, was then lyophilized, yielding a weight of 70 mg. H-1 NMR and C-13 NMR of EC-G were then obtained. C-13 NMR of EC-G showed 16 major carbon peaks. The mass spectra of EC-G was difficult to obtain due to its hydrophilicity and its tendency to be retained on the mass spectrometry column. However, EC-G bis-acetylated compound is less hydrophilic than EC-G; thus, mass spectra of EC-G bis-acetylated could be obtained. Mass spectra of EC-G showed that there was small impurity from EC-G bis-acetylated compound resulting from incomplete hydrolysis procedure. H-1 and C-13 NMR of EC-G were close to the predicted values of EC-G. Although 10 carbon peaks are expected for the symmetric structure of EC-G, glucosamine has 12 carbons instead of 6 carbons, suggesting that glucosamine has two configurations. H-1 NMR experimental values appeared to have a somewhat different profile than the predicted values; however, C-13 NMR experimental values of glucosamine were close to the predicted values of glucosamine. Thus, EC-G appears to have two configurations.

Example 2

Figure 2:
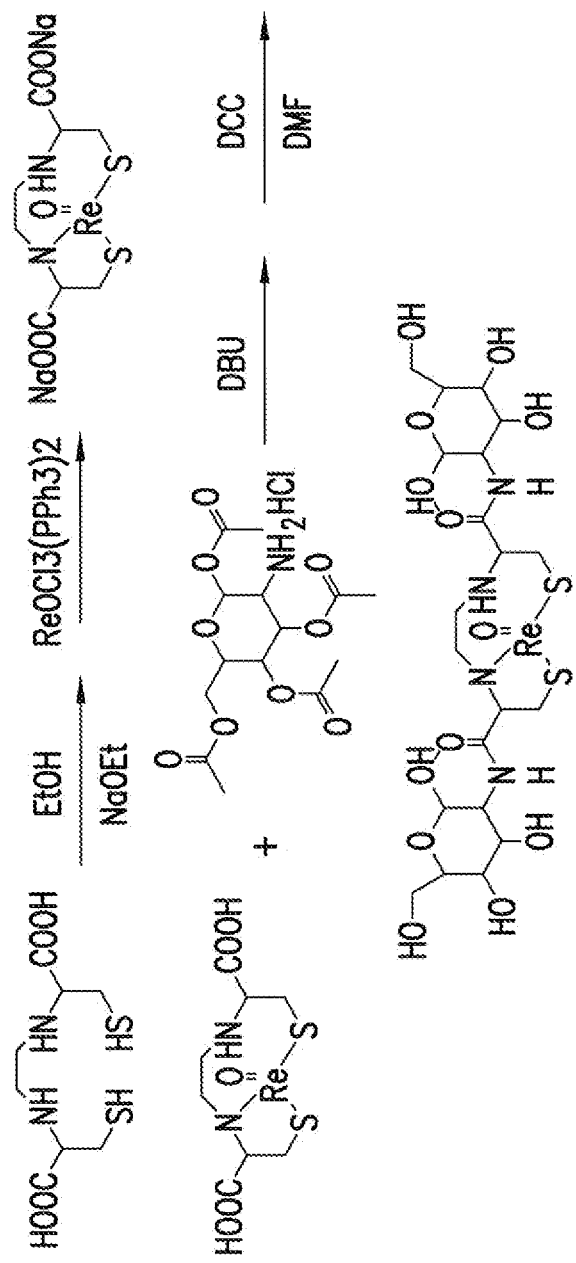
FIG. 2. Non-limiting example of an organic synthesis of rhenium-ethylenedicysteine-glucosamine (Re-EC-G).

Non-Limiting Example of an Organic Synthesis of $^{187}$Re-EC-G Using Re-EC and Protected Glucosamine See FIG. 2

$^{187}$Re-EC-G was used as a reference standard for $^{99m}$Tc-EC due to the similarity in structure and lipophilicity. Synthesis of cold Re-EC-G is shown in FIG. 2. To a stirred ethanol solution, small metal sodium chips (144.8 mg, 6.3 mmol) were added slowly into 10 mL of ethanol in a 50 mL bottle under nitrogen. After the sodium metal dissolved, EC (536.8 mg, 2.0 mmol) was added. The reaction mixture was stirred for 1 hour at room temperature in order to form EC-Na salt. Triphenylphosphine rhenium chloride (ReOCl$_3$(PPh$_3$)$_2$, 1.8329 g, 2.2 mmol) was added. The olive green color of ReOCl$_3$(PPh$_3$)$_2$ changed to a forest green color. The reaction mixture was stirred for 1 hour and then refluxed for 30 min. The reaction mixture was then filtered and the filtrate was evaporated to dryness yielding a gray-purple powder Re-EC (818.4 mg, 80% yield). The structure of Re-EC was confirmed by H-1 and C-13 NMR and mass spectrometry. Re has two isomeric molecular weights which are 185 and 187. Therefore, it distinctively shows two parent ions with 40:60 ratios.

To a stirred dimethylformamide (4 mL) solvent, Re-EC (116.9 mg, 0.25 mmol) was added followed by 1,8-diazabicyclo[5.4.0]undec-7-ene (DBU) (150 mL, 1.0 mmol). Next, dicyclohexylcarbodiimide (DCC) (123.8 mg, 0.6 mmol) was added. The reaction mixture was stirred for 1 hour. Tetraacetylated glucosamine (4-Ac-G-HCl) (184.9 mg, 0.5 mmol) was added and then the reaction was stirred at room temperature overnight. Water (1 mL) was added and the reaction stirred for additional 1 hour at room temperature. The reaction mixture was evaporated under reduced pressure. Water (5 mL) was added, followed by chloroform (5 mL). The water layer was separated and lyophilized to yield a crude dark-brown solid. The solid was purified by column chromatography using Sephadex G-50 to yield cold Re-EC-G (128.4 mg, 65% yield). The structure of cold Re-EC-G was confirmed by H-1 and C-13 NMR and mass spectrometry. Again, the Re-complex distinctively shows two parent ions with 40:60 ratios.

Elemental analysis of cold Re-EC-G showed $C_{20}H_{35}N_4O_{13}ReS_2$ (C, H, N) with the calculated value C, 30.41; H, 4.47; N, 7.09. found value C, 30.04; H, 4.93; N, 6.09. H-1 and C-13 NMR of cold Re-EC-G was similar to the predicted NMR spectrometry. EC-G (5 mg) was labeled with $^{99m}$Tc (pertechnetate) (1 mCi) in the presence of tin(II) chloride (0.1 mg). HPLC analysis showed that cold Re-EC-G had a similar retention time to that of $^{99m}$Tc-EC-G.

Example 3

Synthesis of EC-G Using EC and Glucosamine in an Aqueous Reaction

EC (107 mg, 0.4 mmol) was dissolved in NaHCO$_3$ (1N, 12 mL). To this colorless solution, sulfo-N-hydroxysuccinimide (sulfo-NHS, 173.7 mg, 0.8 mmol) and 1-ethyl-3-(3-dimethylaminopropyl) carbodiimide-HCl (EDAC) (Aldrich Chemical Co, Milwaukee, Wis.) (153.4 mg, 0 8 mmol) were added. D-Glucosamine hydrochloride salt (Sigma Chemical Co., St Louis, Mo.) (345 mg, 1.6 mmol) was then added. A pH of 8 was measured. The mixture was stirred at room temperature for 16 hours and then dialyzed for 24 hours using Spectra/POR molecular porous membrane with cut-off at 500 (Spectrum Medical Industries Inc., Houston, Tex.). After dialysis, the product was filtered by a 0 45 μm Nylon-filter and then freeze-dried using a lyophilizer (Labconco, Kansas City, Mo.). The crude product weighed 300-400 mg. H-1 NMR of EC-G showed similar patterns; however, it appears that the mixture is not as pure when compared to the organic EC-G. Elemental analysis showed EC-G purity was 63-77% using different reaction ratios between EC and glucosamine. Prep-HPLC (7.8×300 mm C-18 column, Waters) (flow rate: 0.5 mL/min, 100% water, UV 235 nm) was used to purify the crude product, 180-240 mg (yield 60%). H-1 and C-13 NMR of EC-G after prep-HPLC showed additional peaks suggesting impurities from mono EC-G or EC-glucosamine, sulfo-NHS and EDAC. Prep-HPLC purification of the raw EC-G yielded some incremental improvement to the chemical purity; however, when the raw EC-G is labeled with $^{99m}$Tc in the presence of tin(II) chloride, a greater than 95% radiochemical purity of $^{99m}$Tc-EC-G can be achieved using gluconate as a transchelator (as shown in radio-TLC and HPLC analysis).

Example 4

Figure 4:
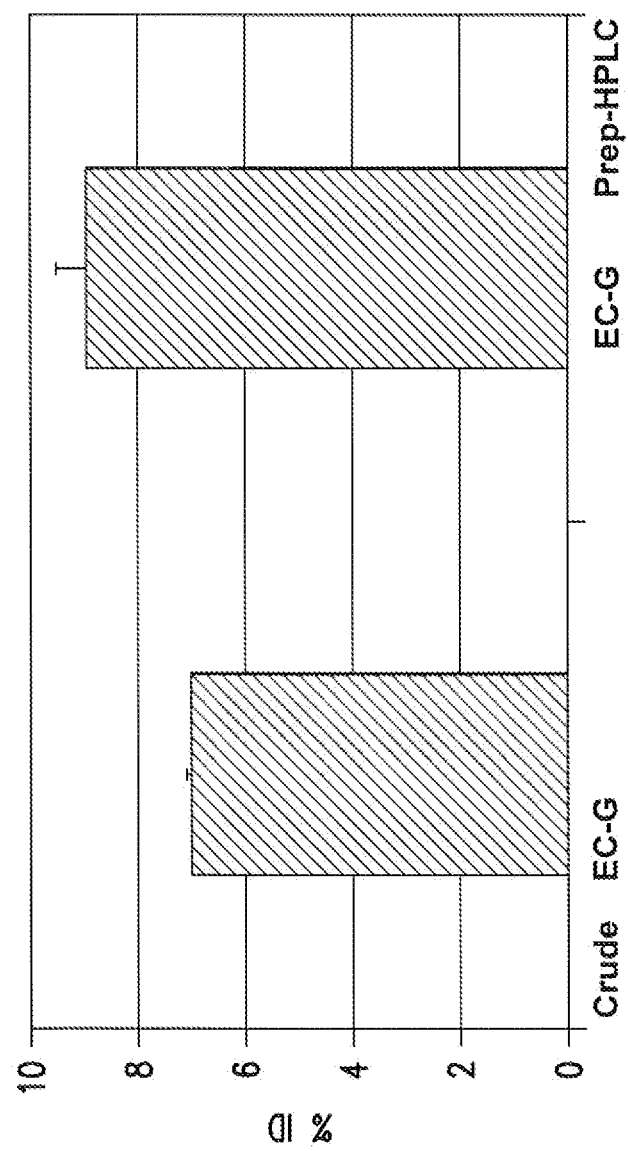
FIG. 4. Comparison of cellular uptake of Ec-G in crude form or prep HPLC-purified form.
Figure 5:
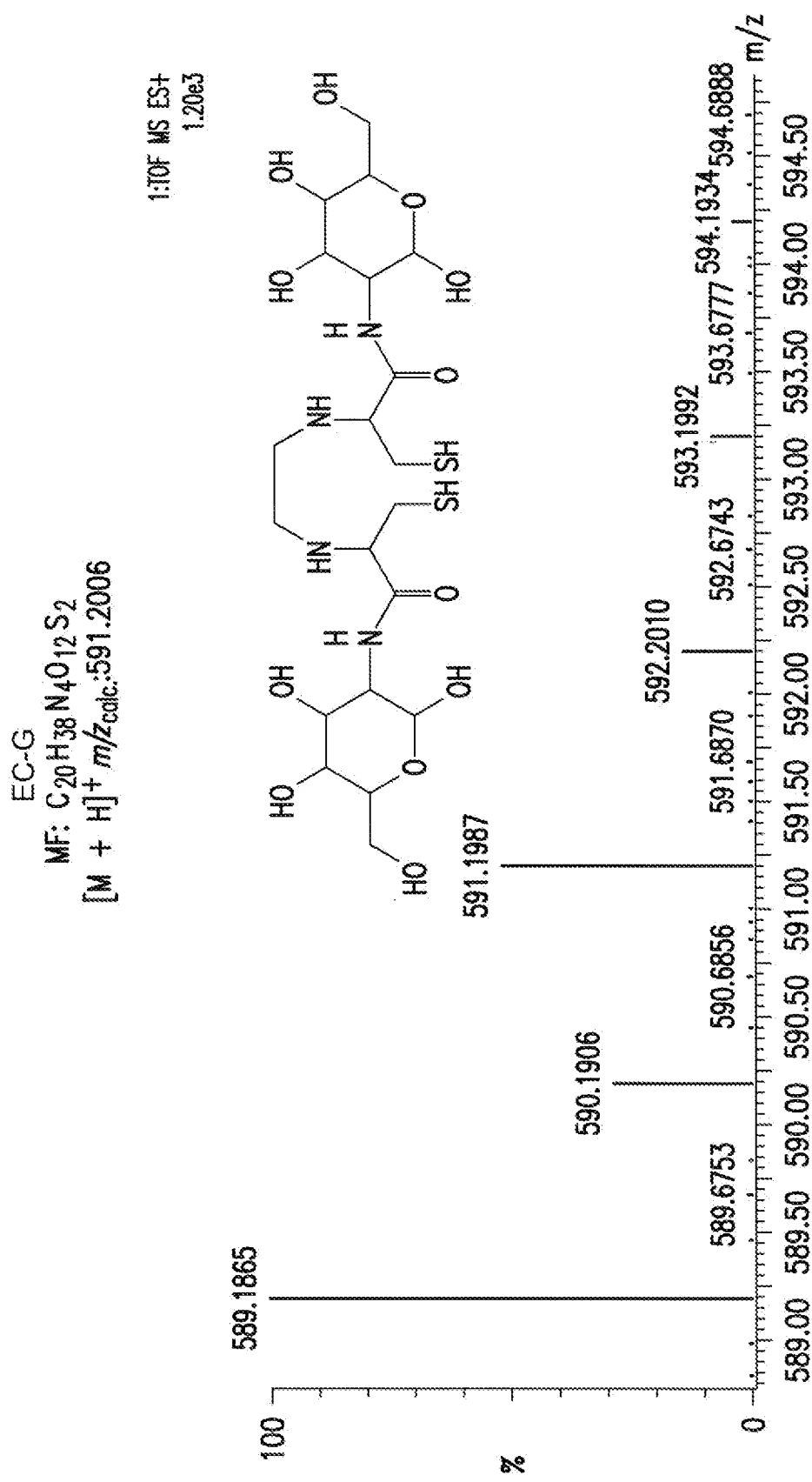
FIG. 5. Mass spectrometry of EC-G.

Cellular Uptake Study Comparing Products Synthesized Via the Aqueous Method and the Organic Method To further validate EC-G biological activity, in vitro cell culture assays were performed. Briefly, the cellular uptake was determined in tumor cells (50,000 cells/well) incubated with $^{99m}$Tc-EC-G (2 μCi/well) at various time intervals. The cellular uptake assay showed no marked difference between raw (unpurified) EC-G and prep-HPLC purified EC-G (FIG. 4) In vitro stability studies were determined either using cell culture or dissolving EC-G in water. There was a 10-15% decrease in cellular uptake using $^{99m}$Tc-EC-G after 2-4 weeks. The useful life of EC-G in water appears to be 17.26 days. In vivo imaging studies showed no marked difference between EC-G synthesized from aqueous and organic reactions.

Example 5

Synthesis of Cold Re-EC-G Using Re-EC and Glucosamine in an Aqueous Reaction

Re-EC (255.8 mg, 0.5 mmol) (from Example 2) was dissolved in NaOH (1N, 4.5 mL). Added to this dark-purple color solution were sulfo-NHS (217.1 mg, 1 mmol) and D-glucosamine hydrochloride salt (Sigma Chemical Co., St. Louis, Mo.) (431.3 mg, 2 mmol). 1-Ethyl-3-(3-dimethylaminopropyl)carbodiimide-HCl (EDAC) (Aldrich Chemical Co., Milwaukee, Wis.) (191.7 mg, 1 mmol) was then added. The pH measured greater than 8. The mixture was stirred at room temperature for 16 hours. The mixture was dialyzed for 24 hours using Spectra/POR molecular porous membrane with cut-off at 500 (Spectrum Medical Industries Inc., Houston, Tex.). After dialysis, the product was filtered and then freeze-dried using a lyophilizer (Labconco, Kansas City, Mo.). The crude product weighed 276 mg. H-1 NMR of aqueous Re-EC-G showed a similar pattern; however, there appears to be some evidence of impurities when compared to the organic Re-EC-G compound. HPLC analysis of the organic cold Re-EC-G compound showed one peak at 272 nm; however, aqueous cold Re-EC-G had two peaks. One of the peaks in the aqueous cold Re-EC-G corresponds to the organic cold Re-EC-G compound (peaks 12.216 and 12.375, respectively). The remaining peaks were sulfo-NHS and other minor impurities.

Example 6

Quantitative Analysis of Glucosamine (Active Pharmaceutical Ingredient)

D-Glucosamine was derivatized for colorimetric assays. Briefly, to a solution of D-glucosamine hydrochloride (25 g, 0.12 mol) in a freshly prepared aqueous solution of 1N NaOH (120 mL) under stirring was added p-anisaldehyde (17 mL, 0.14 mol). After 30 min., crystallization began and the mixture was refrigerated overnight. The precipitated product was then filtered and washed with cold water (60 mL), followed by a mixture of EtOH-Et$_2$O (1:1) to give 2-deoxy-2-[p-methoxybenzylidene(amino)]-D-glucopyranose (D-glucosamine-anisaldehyde, 32.9408 g, 110.8 mmol, 95.5% yield) m.p. 165-166° C. H-1 NMR confirmed the structure.

Raw EC-G (50 mg) was hydrolyzed using 1N NaOH. Anisaldehyde was added to the reaction solution. After 2 hours, the reaction mixture was extracted with chloroform. The chloroform layer, which contained unreacted anisaldehyde, was evaporated under nitrogen. The reacted anisaldehyde weight was used to determine the amount of glucosamine in the D-glucosamine-anisaldehyde adduct.

Example 7

Quantitative Analysis of EC in EC-G

Raw EC-G (50 mg) was hydrolyzed using 1N NaOH. Benzyl chloride was dissolved in dioxane (30 mL) and then added in to the stirred mixture. The reaction was stirred for 2 hours and then extracted with chloroform. The chloroform layer, which contained unreacted benzyl chloride, was evaporated under nitrogen. The reacted benzyl chloride weight was used to determine the amount of EC in EC-G (Table 3).

Example 8

Quantitative Analysis of Sulfo-NHS and EDAC in EC-G

A standard curve of sulfo-NHS was generated at UV 272 nm. Raw EC-G was dissolved in water. From the standard curve, the amount of sulfo-NHS in EC-G was determined at UV 272 nm. The amount of 1-ethyl-3-(3-dimethylaminopropyl) carbodiimide-HCl (EDAC) was calculated by subtracting EC, glucosamine and sulfo-NHS from total EC-G weight shown in Table 3.

Example 9

Quantitative Analysis of Glucose Phosphorylation Assay

An in vitro hexokinase assay was used to assess the glucose phosphorylation process of EC-G. Using a kit (Sigma Chemical Company, MO), fluorodeoxyglucose (FDG, 1.0 mg), EC-G (1.0 mg), D-glucosamine (G, 1.0 mg) and D-glucose (2.5 mg) were dissolved in 1 mL (EC-G, G) or 2.5 mL (D-glucose) of water. From there, 200 μL was removed and diluted in 2.5 mL of water. A 100 μL aliquot was then removed and combined in solution with 900 μL of Infinity™ Glucose Reagent and incubated at 37° C. for three min. The phosphorylated glucose and NADH were then assayed at a wavelength of 340 nm. The peaks of FDG (340 and 347 nm), glucose (301 and 342 nm), EC-G (303 and 342 nm) and G (302 and 342 nm) were obtained.

Example 10

Chemical Identity Assay of Glucosamine (Active Pharmaceutical Ingredient) in EC-G (Synthesized from the Aqueous Reaction)

A colorimetric assay was used to determine the amount of glucosamine. A solution of copper sulfate (6.93 g in 100 mL water) and sodium potassium tartrate (34.6 g in 100 mL water containing 10 g NaOH) was prepared. EC-G (25 mg) and glucosamine (standard) were added with basic copper tartrate solution until no visualization of copper oxide red precipitate existed. The amount of glucosamine in EC-G was 8.7 mg (35% w/w) determined from titration volume (Table 3).

Alternatively, as described in Example 5, D-glucosamine hydrochloride (25 g, 0.12 mol) was added to a freshly prepared aqueous solution of 1N NaOH (120 mL) under stirring and then p-anisaldehyde (17 mL, 0.14 mol) was added to the mixture. After 30 min., the crystallization began and the mixture was refrigerated overnight. The precipitated product was filtered and washed with cold water (60 mL), followed by a mixture of EtOH-Et$_2$O (1:1) to yield 2-deoxy-2-[p-methoxybenzylidene(amino)]-D-glucopyranose (D-glucosamine-anisaldehyde, 32.9408 g, 110.8 mmol, 95.5% yield) m.p. 165-166° C. Raw EC-G (50 mg) was hydrolyzed using 1N NaOH. Anisaldehyde was added to the reaction solution. After 30 min., the crystallization began and the mixture was refrigerated overnight. The precipitated product was filtered and washed with cold water and the melting point was determined to be 165-166° C. (containing 18 mg glucosamine).

TABLE 3

Qualitative Analysis of Glucosamine and EC in EC-G (synthesized from the aqueous reaction)

Theoretical Value

| Compound | Molecular Weight | Percentage (weight/weight) (100%) | (65%) |
|---|---|---|---|
| EC-G | 591 | | |
| EC | 268 | | |
| Glucosamine (G) | 179 | | |
| EC in EC-G | | 39% (234/591) | 25% |
| G in EC-G | | 60% (356/591) | 39% |

Experimental Value

| Compound | Percentage (weight/weight) | Method |
|---|---|---|
| EC in EC-G | 30% | colorimetric |
| G in EC-G | 35% | colorimetric |
| Sulfo-NHS in EC-G | 34% | UV (268 nm) |
| EDAC | 1% | calculation |

Example 11

Chemical Identity Assay of Ethylenedicysteine (Chelator) in EC-G (Synthesized from the Aqueous Reaction)

Two methods were used to determine the purity of EC-G. In the first method, a colorimetric assay was used to determine the amount of EC. A solution of iodine (0.1 mol/L) (13 g along with 36 g KI in 1000 mL water) was prepared and EC-G (25.2 mg) and EC (25 mg) (standard) were added to the iodine solution. In the standard EC, a pale white solid was precipitated, but no precipitate was noted in the EC-G. A titration method was used (yellowish color (persists more than 5 min.)) to determine the amount of EC in the EC-G. Each 1 mL of iodine solution that was used equals 13.4 mg of EC. The amount of EC in the EC-G was 7.6 mg (30.2% w/w).

In the second method, measurement the melting point of a thiol-EC-G adduct was performed. Example 1 outlined the synthesis of S,S'-Bis-benzyl-N,N'-ethylenedicysteine (Bz-EC). Briefly, EC (2.684 g, 10 mmol) was dissolved in 1N NaOH (40 mL). Benzyl chloride (5.063 g, 40 mmol) was dissolved in dioxane (30 mL) and added to a stirred mixture. After 30 min., the pH of the solution was adjusted to 2 with concentrated HCl. The precipitate was filtered and washed with water and recrystallized from trifluoroacetic acid. The yield was 79.0% (3.5454 g), m.p. 227-229° C. (dec.) (reported 229-230° C.). Raw EC-G (50 mg) was then hydrolyzed using 1N NaOH, and benzyl chloride (40 mg) was added. The reaction mixture was stirred for 30 min. The pH of the solution was adjusted to 2 with concentrated HCl. The precipitate was filtered and washed with water to give EC-benzyl adduct, m.p. 227-229° C. (containing EC 16 mg).

Example 12

Chemical Identity Assay of Sulfo-N-Hydroxysuccinimide (Sulfo-NHS) in EC-G (Synthesized from the Aqueous Reaction)

The assay for N-hydroxysulfosuccinimide (sulfo-NHS) was determined by UV (268 nm). A standard curve of sulfo-NHS was produced at UV 268 nm. Under this UV absorbance, poor absorbance was observed for EC-G and EDAC. Raw EC-G (50 µg/mL) was dissolved in water and the absorbance was measured at 268 nm. The estimated sulfo-NHS was 35±5% (w/w).

Example 13

Radiochemical Purity and Identity Assay

Figure 3:
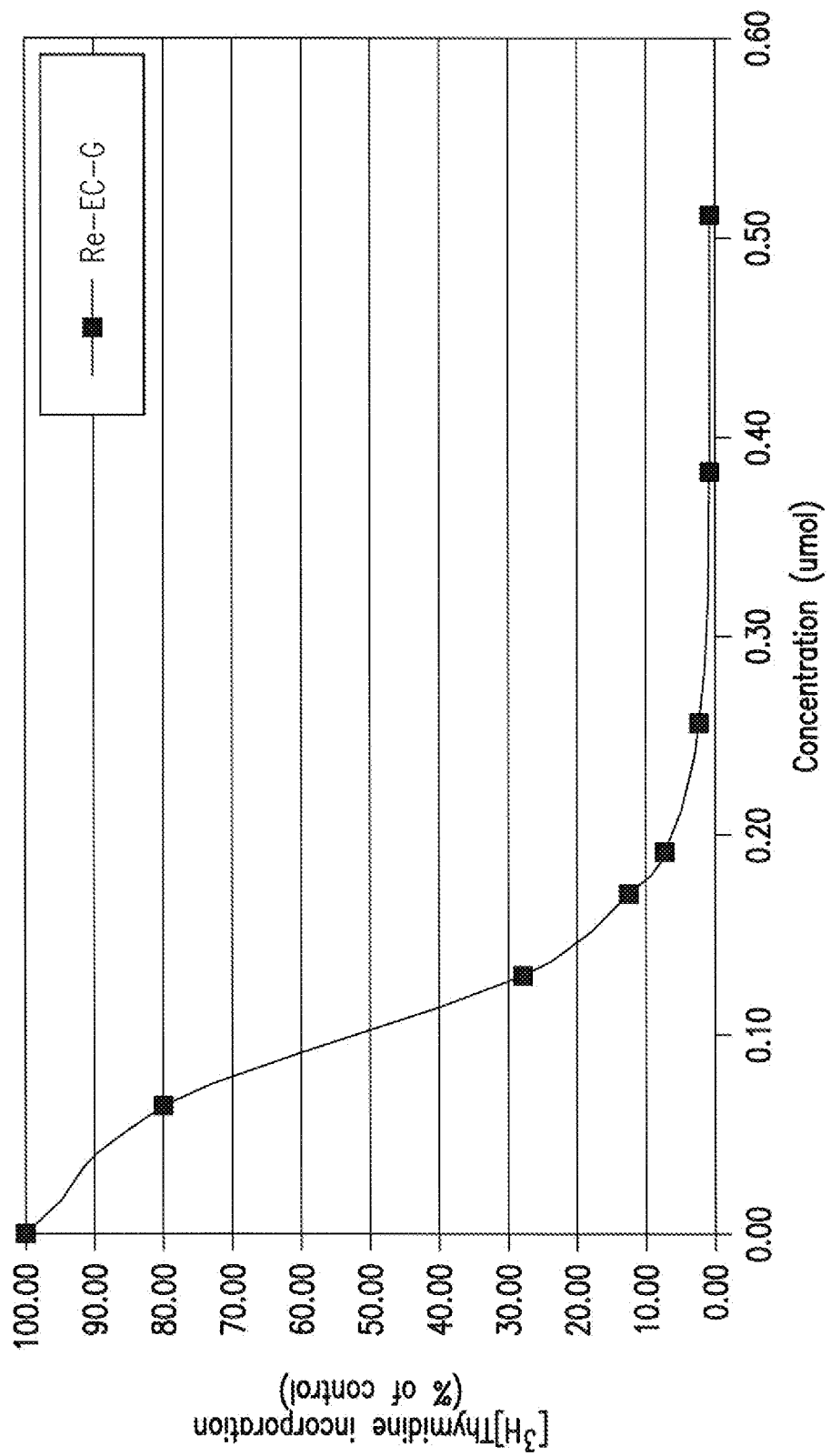
FIG. 3. [$^3$H]Thymidine incorporation assay using Re-EC-G and a lymphoma cell line.

Thin-layered chromatography (TLC) and high performance liquid chromatography (HPLC) were used to determine radiochemical identity. For the TLC assay, both aqueous and organic synthesized EC-G were labeled with $^{99m}$Tc and spotted on a TLC strip impregnated with silica gel column (ITLC-SG) and scanned using a radio-TLC scanner. The retention factor (Rf) values of $^{99m}$Tc-EC-G (from the aqueous synthesis) and the reference standard ($^{99m}$Tc-EC-G from the organic synthesis) were 0.8 (determined by ammonium acetate (1M):methanol; 4:1) or saline. For the HPLC assay, the chemical purity of the organic and aqueous synthesized EC-G were 95.64% and 90.52%, respectively. EC-G synthesized from the organic reaction was more pure than EC-G synthesized from the aqueous reaction. Both the organic and aqueous synthesized EC-G were labeled with $^{99m}$Tc and loaded (20 µL, 1 mg/mL EC-G) on a C-18 reverse phase column (Waters, semi-prep, 7.8×300 mm). The retention time (Rt) values of $^{99m}$Tc-EC-G and cold Re-EC-G (the reference standard from the organic synthesis) were between 11.7-13.5 min. (determined by 100% water @ 0.5 mL/min, UV at 210 nm). Both the organic and aqueous synthesized $^{99m}$Tc-EC-G were detected by UV wavelength (210 nm) and the matched radioactive detector findings were within the above stated ranges. In vitro cell culture assays showed that Re-EC-G produced a dose response curve (FIG. 3) and was effective against human lymphoma cells.

Summary:
- The radiochemical purity of the $^{99m}$Tc-EC-G measured by HPLC and TLC is greater than 95% for the aqueous synthesized EC-G, which closely approximates the radiochemical purity for the organic synthesized EC-G.
- The chemical purity of the unlabeled aqueous EC-G measured by colorimetric and elemental analysis falls in the range of 60-70%. All impurities contained in the EC-G compound (whether the aqueous or organic synthesis) have been clearly identified through colorimetric assays and UV spectrometry as glucosamine (35%), EC (30%), sulfo-NHS (34%) and EDAC (1%) on a w/w basis.
- When measured by HPLC at UV 210 nm, the chemical purity of the unlabeled aqueous EC-G compares very favorably to the unlabeled organic EC-G at 90.52% vs. 95.64%, respectively.
- Retention time of the aqueous $^{99m}$Tc-EC-G is in the range of cold Re-EC-G measured by HPLC at 272 nm.
- NMR ($^1$H, $^{13}$C) of aqueous EC-G is in the range of cold Re-EC-G.
- Unlabeled organic EC-G, labeled organic EC-G and cold Re-EC-G are used as reference standards.
- Biologic assays (in vitro uptake and in vivo imaging) showed no marked difference between aqueous and organic synthesized EC-G.

Example 14

Figure 6A:
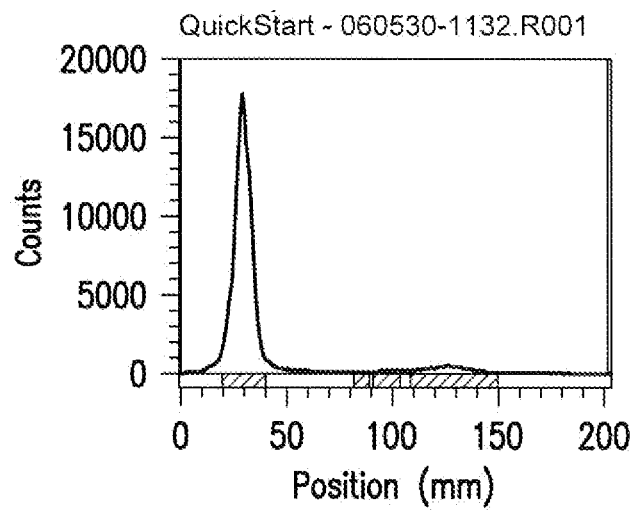
FIG. 6. Radio-TLC (thin layer chromatography) of $^{68}$Ga-EC-G. (a) $^{68}$Ga-EC-G, synthesized via organic means; (b) $^{68}$Ga-EC-G, synthesized via aqueous means; (c) free $^{68}$Ga.
Figure 6B:
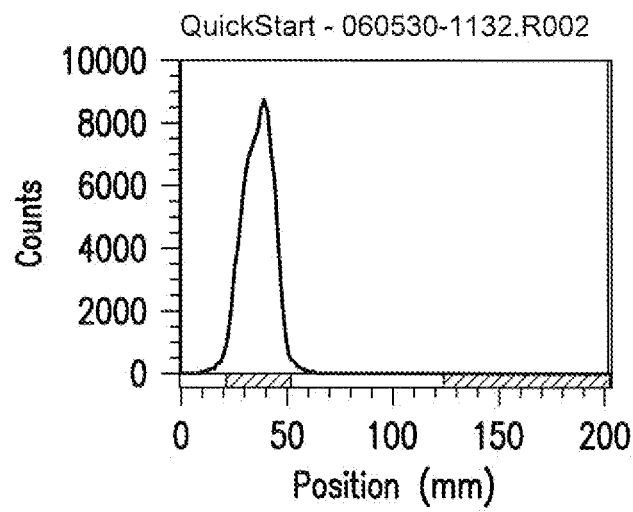
Figure 6C:
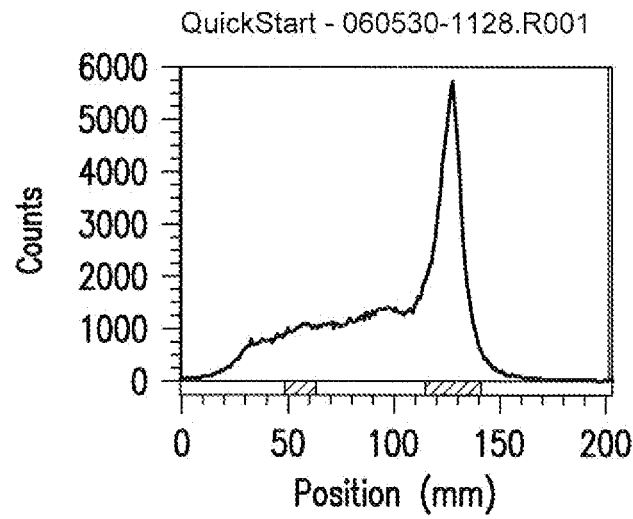
Figure 7A:
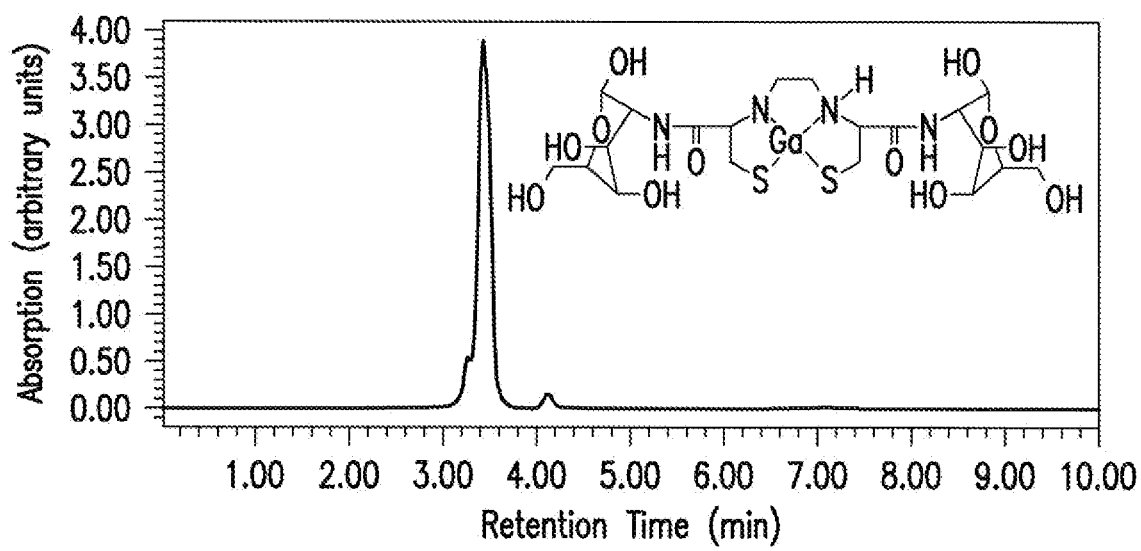
FIG. 7. Analytic radio-HPLC of $^{68}$Ga-EC-G. (a) UV detection; (b) NaI detection.
Figure 7B:
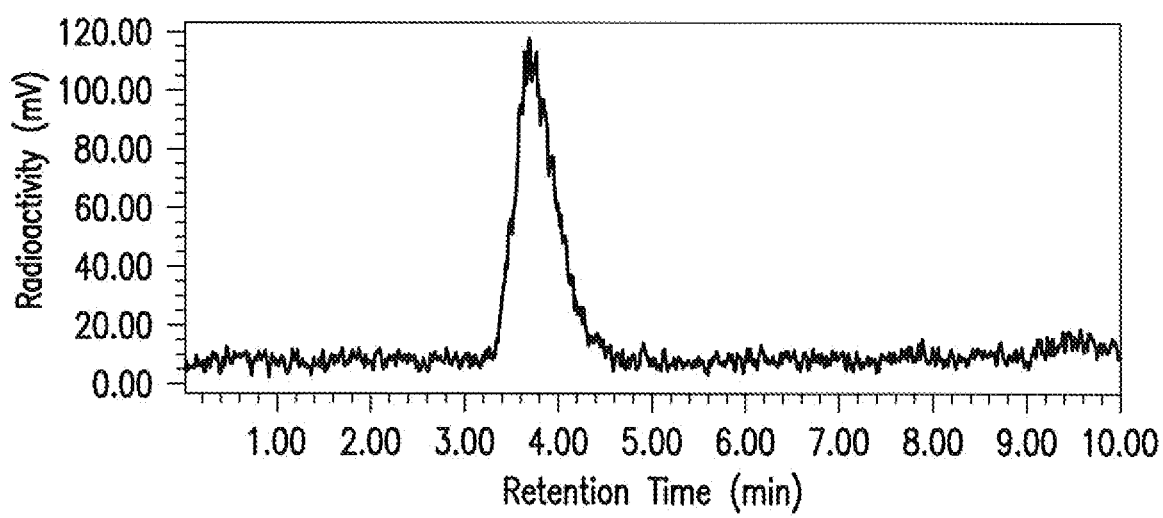

Purity Analysis of $^{68}$Ga-EC-G $^{68}$Ga-EC-G synthesized by both organic and aqueous means were analyzed via radio-TLC. FIG. 6 shows the improved purity of the organic product (a) over the aqueous product (b). FIG. 7 represents purification performed on a C-18 column (Puresil, 4.6×150 mm, Waters, Milford, Mass.) and eluted with water using a flow rate of 0.5 ml/min. Detection was performed via UV and NaI.

Example 15

Stability Analysis of $^{68}$Ga-EC-G

FIG. 8 depicts the results of a study of the stability of $^{68}$Ga-EC-G in dog serum as shown by radio-TLC. 100 µL $^{68}$Ga-EC-G (0.7 mg/0.7 ml, pH 7.5, 865 µCi) were added to 100 µL dog serum and incubated for 0, 30, 60 and 120 minutes. Next, 200 µL MeOH were added to each sample and vortexed before elution using a system comprising pyridine:EtOH:water=1:2:4; Whatman #1 paper. (a) $^{68}$Ga-EC-G (0.7 mg/0.7 ml, pH 7.5, 865 µCi); (b) 100 µL $^{68}$Ga-EC-G in 100 µL dog serum, time=0; (c) time=30 min.; (d) time=60 min.; (e) time=120 min.; (f) $^{68}$Ga-EC-BSA.

Figure 9:
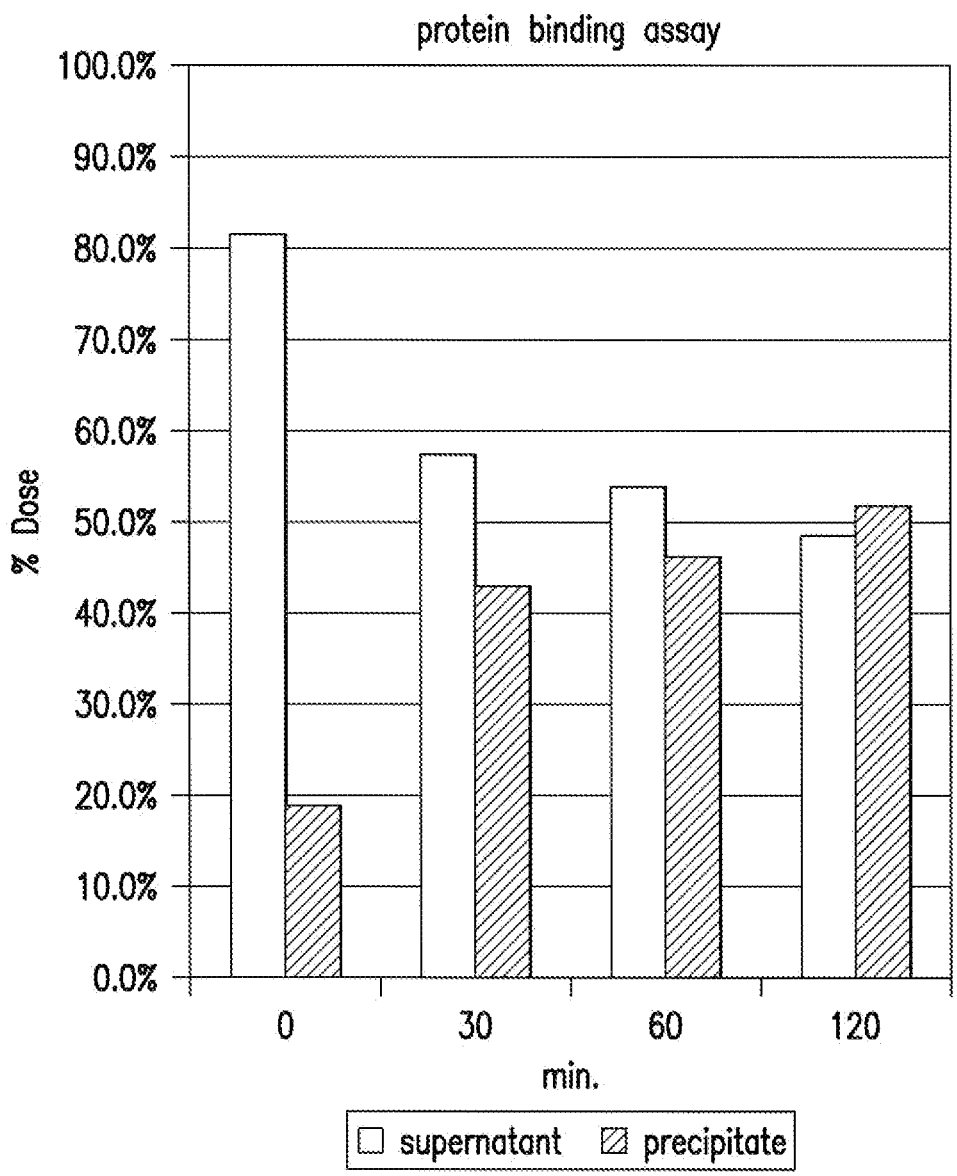
FIG. 9. Stability of $^{68}$Ga-EC-G in dog serum as analyzed in a protein binding assay.

FIG. 9 depicts the results of a study of the stability of $^{68}$Ga-EC-G in dog serum as analyzed in a protein binding assay. A control sample was incubated with $^{68}$Ga-EC-bovine serum albumin (BSA) in dog serum. 100 µL $^{68}$Ga-EC-G (0.7 mg/0.7 ml, pH 7.5, 865 µCi) were added to 100 µL dog serum and incubated for 0, 30, 60 and 120 minutes, the activity counted, then 200 µL MeOH was added and the sample vortexed, centrifuged for 1 minute, and then supernatant and precipitate were each counted. The counts determined in the precipitate are indicative of the degree of binding between $^{68}$Ga-EC-G and proteins in the dog serum.

The protein binding rate increased from 18.6% to 51.5% after 2 hrs, suggesting the targeting potential of $^{68}$Ga-EC-G.

Example 16

In Vitro Update Study of $^{68}$Ga-Labeled Compounds in Breast Cancer Cell Line 13762

Figure 10:
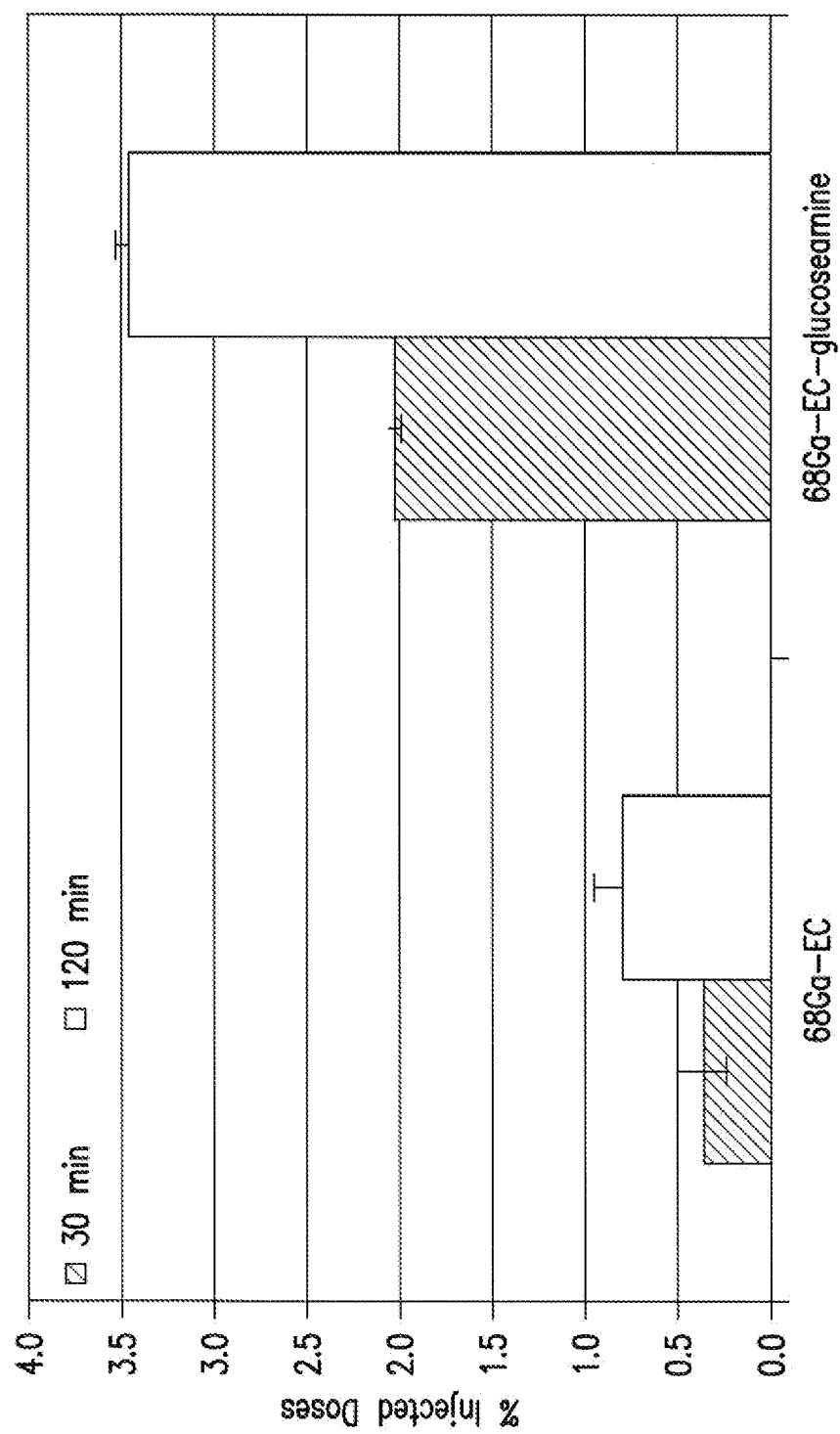
FIG. 10. In vitro uptake study of $^{68}$Ga-labeled compounds in breast cancer cell line 13762.

FIG. 10 depicts results from an in vitro uptake study of $^{68}$Ga-labeled compounds in breast cancer cell line 13762. Cellular uptake of $^{68}$Ga-EC and $^{68}$Ga-EC-G in 13762 cells (1 µCi/50,000 cells per well). Cellular uptake of $^{68}$Ga-EC-G was significantly (p<0.01) higher than control $^{68}$Ga-EC at 0.5-2 hrs.

Example 17

Imaging of Cardiovascular Disease

Figure 11:
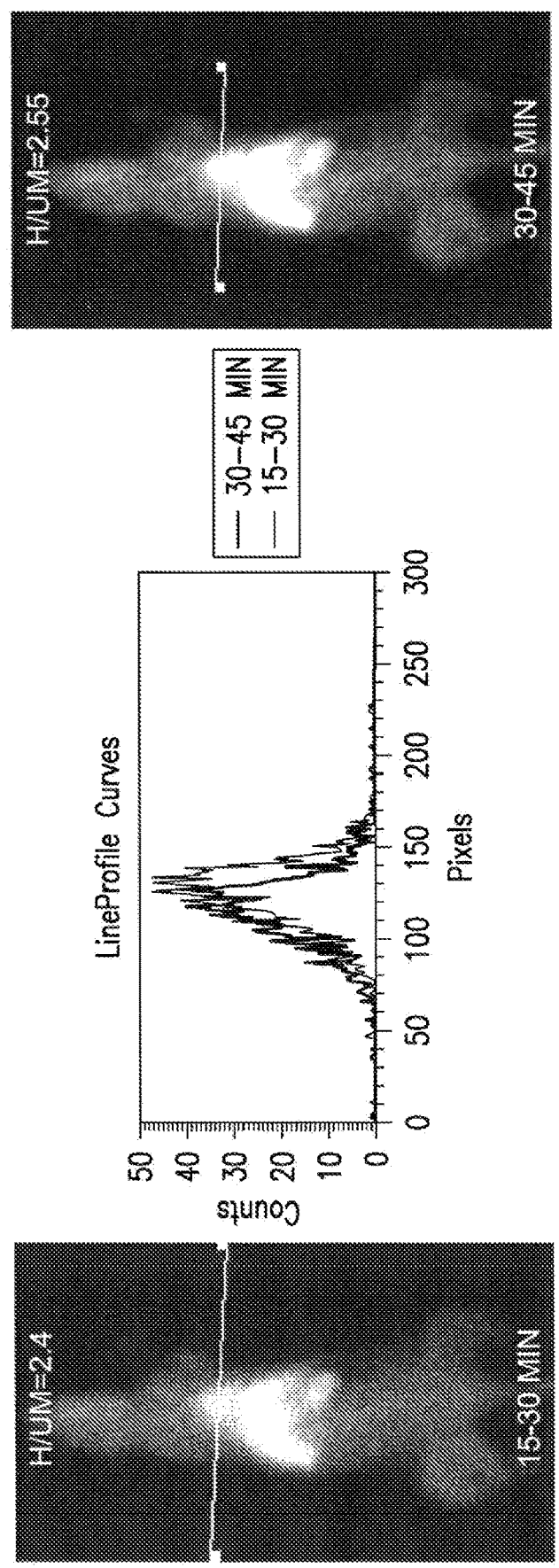
FIG. 11. Planar images of the $^{99m}$Tc-EC-ESMOLOL derivative (300 µCi/rat) in breast tumor-bearing rats. H/UM=heart/upper mediastinum count density (counts/pixel) ratios at 15-45 minutes.
Figure 12:
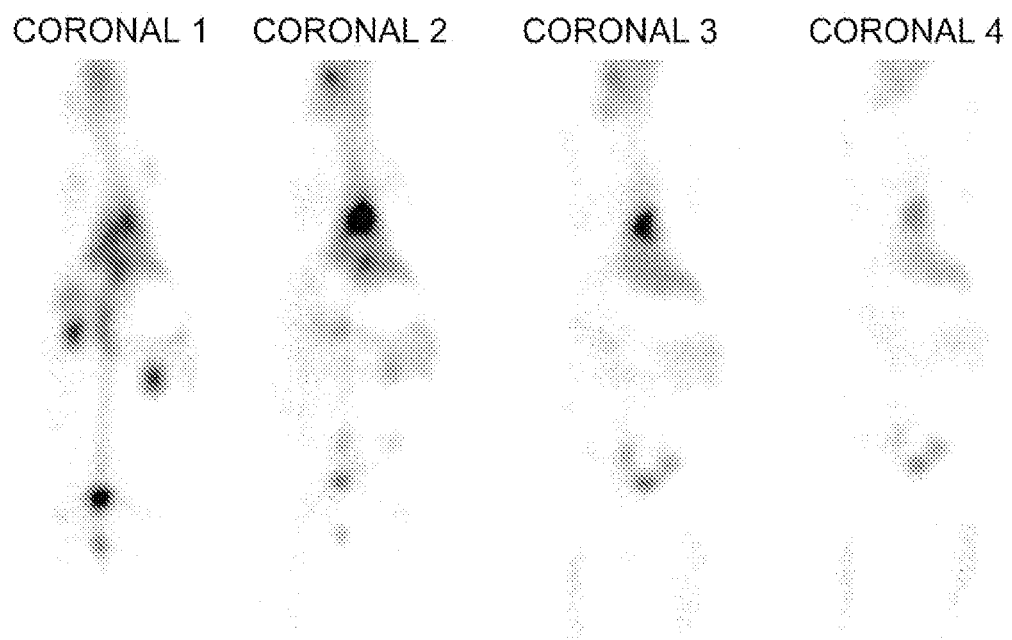
FIG. 12. $^{68}$Ga-EC-TML PET imaging in a New Zealand white rabbit.

FIG. 11 shows planar scintigraphy images of a $^{99m}$Tc-EC-ESMOLOL derivative (300 µCi/rat) in breast tumor-bearing rats. The numbers are heart/upper mediastinum (H/UM) count density (count/pixel) ratios at 15-45 minutes. The line profile in FIG. 11 shows a high cardiac region count/pixels ratio in comparison to laterally located tissues. These results demonstrate that $^{99m}$Tc-EC-ESMOLOL is surprisingly effective at imaging the cardiac region. FIG. 12 shows $^{68}$Ga-EC-TML PET imaging results in a New Zealand white rabbit. A rabbit was administered $^{68}$Ga-EC-trimethyl lysine (EC-TML). PET coronal images were acquired at 45 minutes after injection of 0.66 mCi of $^{68}$Ga-EC-TML (dorsal to ventral order). High uptake in the heart was noticed, suggesting EC-TML was involved in fatty acid metabolism.

Example 18

Figure 13:
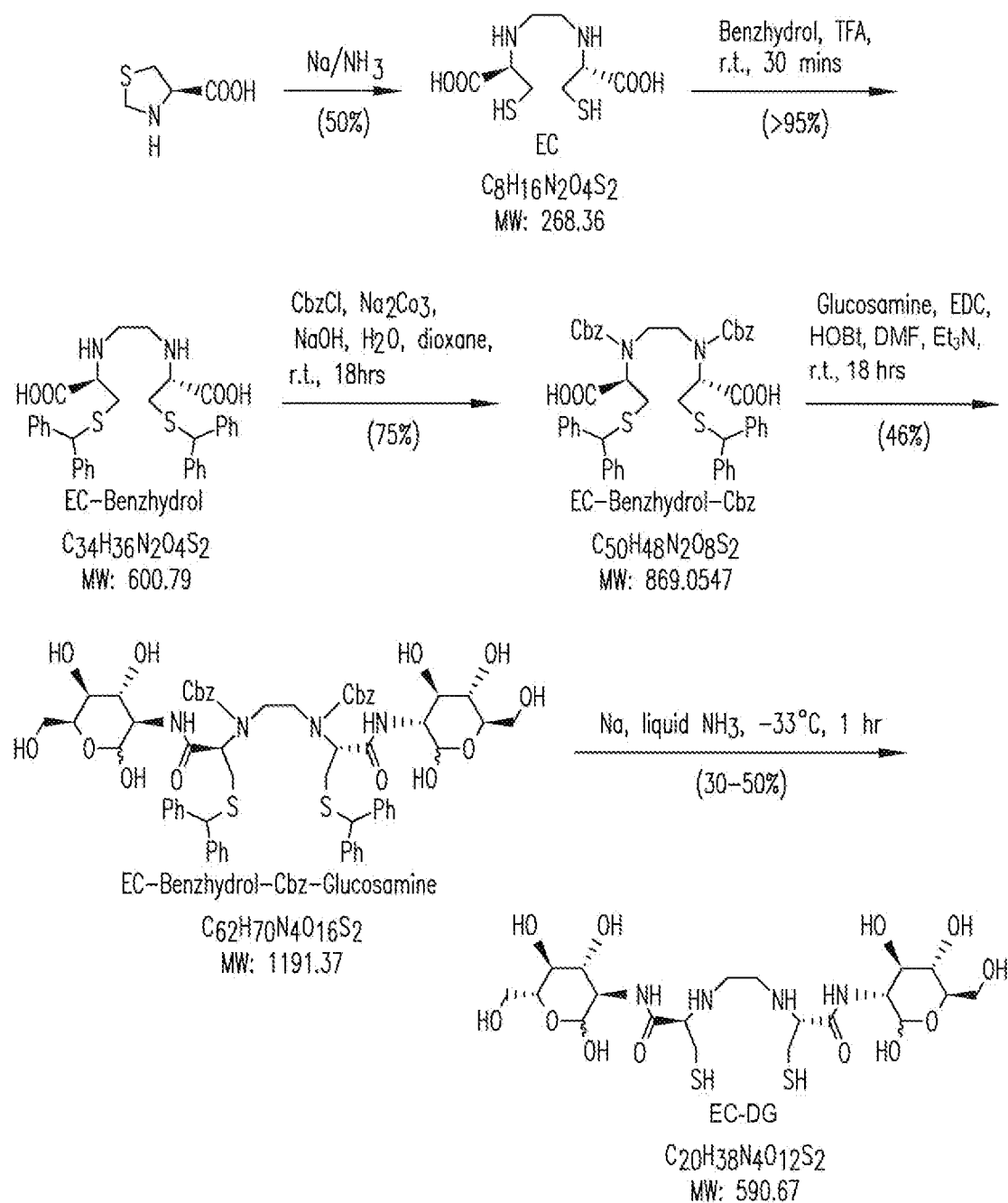
FIG. 13. Non-limiting example of an organic synthesis of ethylenedicysteine-glucosamine (EC-G).

Non-Limiting Example of Organic Synthesis of EC-G Via an EC-Benzhydrol-Cbz-Glucosamine Intermediate (see FIG. 13)

EC-Benzhydrol-Cbz-Glucosamine can be dissolved in ethyl acetate and precipitated out by adding MTBE or n-Hexane. This was envisioned as a method of obtaining pure a penultimate species in a method of obtaining EC-G. The purity (HPLC) of EC-Benzhydrol-Cbz-Glucosamine before this trituration treatment was about 64%. After trituration, the purity was about 68% (MTBE) or 65%-80% (n-Hexane). Another envisioned method for purifying the product is through use of a biotage cartridge, as since the silica gel in these cartridges is more active than flash grade silica gel.

Other purification techniques and procedures were also attempted using different solvent systems as an alternative to chromatography, the results of which are shown in Table 4 below. Precipitation was attempted in different solvent systems. The EC-Benzhydrol-Cbz was dissolved in a selected solvent (A), and slowly charged to a larger volume of co-solvent (B). However, the results did not indicate this approach would be as effective as other methods, as the purity changes were negligible. Triturations were also attempted using the selected solvent systems in various ratios for precipitation. The results for the triturations also suggest the material is not pure enough for certain applications. Column chromatography was also attempted, and the conditions were modified from the previous week (15:1 silica:crude, loaded dry on silica). This method did allow for moderate clean up of the material (from 55 A % to 75 A %).

TABLE 4

EC-Benzyhydrol-Cbz Purification by Precipitation and Trituration

| Solvent A | Solvent B | Precipitation Result | Trituration Result |
|---|---|---|---|
| Ethyl Acetate | Hexane | Sticky solid | Oil |
| Methanol | Water | Sticky oil | Oil |
| DCM | Hexane | Sticky oil | Oil |
| Ethanol | Water | Sticky oil | Oil |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,605,672
U.S. Pat. No. 6,692,724
U.S. Pat. No. 6,737,247
U.S. patent application Ser. No. 09/599,152
U.S. patent application Ser. No. 10/627,763
U.S. patent application Ser. No. 10/672,142
U.S. patent application Ser. No. 10/703,405
U.S. patent application Ser. No. 10/732,919
Alauddin and Conti, *Nucl. Med. Biol.*, 25(3):175-180, 1998.
Alauddin et al., *Nucl. Med. Biol.*, 23:787-792, 1996.
Alauddin et al., *Nucl. Med. Biol.*, 26:371-376, 1999.
Alberico et al., *Surg. Oncol. Clin. N. Am.*, 13(1):13-35, 2004.
Angello et al., *Am. J. Cardiol.*, 60:528-533, 1987.
Benveniste and Davies, *Proc. Natl. Acad. Sci. USA*, 70(8):2276-2280, 1973.
Blondeau et al., *Can. J. Chem.*, 45:49-52, 1967.
Bodansky, In: *Peptide Chemistry*, 2$^{nd}$ ed., Springer-Verlag, New York, 1993.
Bolhuis et al., *Int. J. Cancer Suppl.*, 7:78-81, 1992.
Borodina et al., *Appl. Environ. Microb.*, 71(5):2294-302, 2005.
Bush et al., *Br. J. Cancer Suppl.*, 37(3):302-306, 1978.
Campbell et al., *Cancer Res.*, 51(19):5329-5338 1991.
Canevari et al., *Hybridoma*, 12(5):501-507, 1993.
Chasselle et al., *Lancet*, 34B:143, 1995.
Coney et al., *Cancer Res.*, 54(9):2448-2455, 1994.
Diamond et al., *J. Biol. Chem.* 253(3):866-871, 1978.
Dische, *Int. J. Radiat. Oncol. Biol. Phys.*, 20(1):147-152, 1991.
Franklin et al., *Int. J. Cancer Suppl.*, 8:89-95, 1994.
Gambhir et al., *J. Nucl. Med.*, 39(11):2003-2011, 1998.
Gambhir et al., *Proc. Natl. Acad. Sci. USA*, 96(5):2333-2338, 1999.

Gambhir et al., *Proc. Natl. Acad. Sci. USA*, 97:2785-2790, 2000.
Gatenby et al., *Int. J. Radiat. Oncol. Biol. Phys.*, 14(5):831-838, 1988.
Ginobbi et al., *Anti-cancer Res.*, 17(1A):29-35, 1997.
Grant, In: *Synthetic Peptides*, Freeman & Co., New York, 1992.
Gray et al., *Nature*, 182(4640):952-953, 1958. Greene and Wuts, In: *Protective Groups in Organic Synthesis*, John Wiley & Sons, New York, 1999.
Gutman et al., *Am. Heart J.*, 106: 989-995, 1983.
Hall et al., *Radiat. Res.*, 114(3):415-424, 1988.
Henson et al., *AJNR Am. J. Neuroradiol.*, 25(6):969-972, 2004.
Hoelscher et al., *Spine*, 25(15):1871-7, 2000.
Holm, et al., *APMIS*, 102(11):828-836, 1994.
Hostetler and Hall, *PNAS*, 79:1663-1667, 1982.
Hsueh and Dolnick, *Biochem. Pharmacol.*, 45(12):2537-2545, 1993.
Hu, *Proc. Natl. Acad. Sci. USA*, 95; 9791-95, 1998.
Iyer et al., *J. Nucl. Med.*, 42(1):96-105, 2001.
Koh et al., *Int. J. Radiat. Oncol. Biol. Phys.*, 22:199-212, 1992.
Kranz et al., *Proc. Natl. Acad. Sci. USA*, 92(20):9057-61, 1995.
Kundra et al., *J. Nucl. Med.*, 43(3):406-412, 2002.
Leamon and Low, *Biochem. J.*, 291 (Pt 3):855-60, 1993.
Leamon and Low, *J. Biol. Chem.*, 267(35):24966-71, 1992.
Leamon and Low, *Proc. Natl. Acad. Sci. USA*, 88(13):5572-76, 1991.
Lee and Low, *J. Biol. Chem.*, 269(5):3198-3204, 1994.
Martin et al., *J. Nucl. Med.*, 30:194-201, 1989.
Medical Letter, 34:78, 1992.
Michalik et al., *Pharmacol Res.* 21(4):405-414, 1989.
Murakami et al., *J Orthop Res.*, 14(5):742-8, 1996.
Murakami et al., *Bone*, 21(5):411-418, 1997.
Myszka et al., *Carb. Res.*, 338:133-141, 2003.
Nakae and Nakae, *Antimicrobial Agents and Chemo.*, October; 22(4):554-59, 1982.
Namavari et al., *Nucl. Med. Biol.*, 27(2):157-62, 2000.
Nordsmark et al., *Radiother. Oncol.*, 41(1):31-39, 1996.
Orr et al., *J. Natl. Cancer Inst.*, 87(4):299-303, 1995.
Ozmen et al., *Drug Chem. Toxicol.*, 28(4):433-45, 2005.
Patrick et al., *J. Neurooncol.*, 32(2):111-23, 1997.
Pohost et al., *Circulation*, 55:294-302, 1977.
Rasey et al., *Int. J. Radiat. Oncol. Biol. Phys.*, 17(5):985-91, 1989.
Rasey et al., *Radiother. Oncol.*, 17(2):167-73, 1990.
Remington's Pharmaceutical Sciences, 18th Ed. Mack Printing Company, 1289-1329, 1990.
Ross et al., *Cancer*, 73(9):2432-43, 1994.
Saha et al., *Semin. Nucl. Med.*, 24(4):324-49, 1994.
Strunk and Schild, *Eur. Radiol.*, 14(6):1055-1062, 2004.
Tachibana et al., *Biochem. Pharmacol.*, 25(20):2297-301, 1976.
Tod et al., *Clin Pharmacokinet.*, March; 38(3):205-223, 2000.
Tjuvajev et al., *J. Nucl. Med.*, 43(8):1072-1083, 2002.
Valk et al., *J. Nucl. Med.*, 33(12):2133-2137, 1992.
Verbruggen et al., *J. Nucl. Med.*, 33:551-557, 1992.
Warrell, Jr et al., *N. Engl. J. Med.*, 329(3):177-189, 1993.
Weitman et al., *Cancer Res.*, 52(12):3396-3401, 1992b.
Weitman et al., *Cancer Res.*, 52(23):6708-6711, 1992a.
Weitman et al., *J Neurooncol.*, 21(2):107-112, 1994.
Westerhof et al., *Cancer Res.*, 51(20):5507-5513, 1991.
Yaghoubi et al., *J. Nucl. Med.*, 42:1225-1234, 2001.
Yanai et al., *Proc. Natl. Acad. Sci. USA*, 103(25):9661-9666, 2006.
Yang et al., *Diabetes*, 53:67-73, 2004.

What is claimed is:

1. A method of imaging the heart of a subject with a cardiovascular disease comprising:
   (a) obtaining a metal ion-labeled-chelator targeting ligand conjugate, the conjugate being between about 90% and about 99.9% pure as measured by HPLC using ELSD detection, wherein the conjugate has been previously prepared by a synthetic method comprising:
      (1) conjugating, in an organic medium, a protected ethylenedicysteine of the following formula:

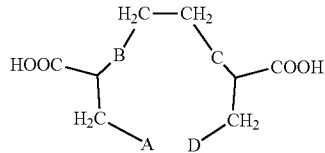

to a glucosamine, wherein:
      A and D are each a protected thiol;
      B and C are each a protected tertiary amine;
      and the conjugation is via an amide bond formed between a —COOH group of the protected ethylenedicysteine and the amino group of the glucosamine to form a protected ethylenedicysteine glucosamine;
      (2) removing each protecting group, in one or more steps, from the protected ethylenedicysteine glucosamine to form ethylenedicysteine glucosamine (EC-G); and
      (3) chelating a metal ion to the EC-G to form a metal ion labeled-chelator-targeting ligand conjugate;
   (b) administering to the subject a pharmaceutically or diagnostically effective amount of the conjugate; and
   (c) imaging the heart of the subject to detect a signal from the metal ion of the conjugate.

2. The method of claim 1, further comprising performing one or more additional diagnostic or imaging procedures to evaluate the subject for a cardiovascular disease.

3. The method of claim 1, wherein the cardiovascular disease is a myocardial infarction, congestive heart failure, cardiomyopathy, valvular heart disease, an arrhythmia, congenital heart disease, angina pectoris, noncardiac circulatory congestion, systolic heart failure, heart failure with normal systolic function, or right-sided heart failure.

4. The method of claim 3, wherein the cardiovascular disease is a myocardial infarction, myocardial ischemia, or angina pectoris.

5. The method of claim 1, wherein the metal ion labeled-chelatortargeting ligand conjugate is $^{99m}$Tc-EC glucosamine, $^{188}$Re-EC-glucosamine, or $^{187}$Re-EC-glucosamine.

6. The method of claim 1, wherein the organic medium comprises a polar solvent.

7. The method of claim 1, wherein the organic medium comprises dimethylformamide, dimethylsulfoxide, dioxane, methanol, ethanol, hexane, methylene chloride, acetonitrile, tetrahydrofuran, or a mixture thereof.

8. The method of claim 1, wherein the synthetic method further comprising at least one purification step, wherein the purification step is silica gel column chromatography, HPLC, or a combination thereof.

9. The method of claim 1, wherein the protected ethylenedicysteine glucosamine is EC-Benzhydrol-Cbz-Glucosamine.

10. The method of claim 1, wherein the metal ion is a radionuclide.

11. The method of claim 1, wherein the subject is a human.

12. The method of claim 1, wherein the signal is detected using a technique selected from the group consisting of PET, PET/CT, CT, SPECT, SPECT/CT, MRI, and optical imaging.

* * * * *

UNITED STATES PATENT AND TRADEMARK OFFICE
CERTIFICATE OF CORRECTION

PATENT NO. : 10,814,013 B2
APPLICATION NO. : 13/562879
DATED : October 27, 2020
INVENTOR(S) : Yang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 207 days.

Signed and Sealed this
Thirteenth Day of December, 2022

Katherine Kelly Vidal
*Director of the United States Patent and Trademark Office*